(12) United States Patent
Anand et al.

(10) Patent No.: US 8,053,638 B2
(45) Date of Patent: Nov. 8, 2011

(54) METHOD FOR AGROBACTERIUM-MEDIATED TRANSFORMATION OF PLANTS

(75) Inventors: Ajith Anand, Ardmore, OK (US); Kirankumar Mysore, Ardmore, OK (US)

(73) Assignee: The Samuel Roberts Noble Foundation, Ardmore, OK (US)

( * ) Notice: Subject to any disclaimer, the term of this patent is extended or adjusted under 35 U.S.C. 154(b) by 753 days.

(21) Appl. No.: 11/835,237

(22) Filed: Aug. 7, 2007

(65) Prior Publication Data

US 2009/0271896 A1 Oct. 29, 2009

Related U.S. Application Data

(60) Provisional application No. 60/836,461, filed on Aug. 7, 2006.

(51) Int. Cl.
*C12N 15/84* (2006.01)
*C12N 5/04* (2006.01)
*C12N 5/10* (2006.01)
*A01H 5/00* (2006.01)
*A01H 5/10* (2006.01)

(52) U.S. Cl. ........ 800/294; 435/419; 435/424; 435/425; 435/426; 435/469

(58) Field of Classification Search .................. None
See application file for complete search history.

(56) References Cited

U.S. PATENT DOCUMENTS

| | | | | |
|---|---|---|---|---|
| 7,288,695 | B2 * | 10/2007 | Allen et al. ................... | 800/298 |
| 7,659,447 | B2 * | 2/2010 | Tzfira et al. ................... | 800/294 |
| 2003/0233676 | A1 | 12/2003 | Tzfira et al. ................... | 800/294 |

OTHER PUBLICATIONS

Tzfira et al. Molecular Plant Pathology 1(4): 201-212 (2000).*
GenBank Accession No. 42567929 (*Arabidopsis* locus NM_121828; At5g18230) available Feb. 23, 2005.*
Anand et al., "Current advances in *Agrobacterium*-plant interaction and their implications in agricultural biotechnology," In: Advances in Plant Physiology, Hemantaranjan (Ed.), Scientific Publishers, Jodhpur, India, 8:221-242, 2005.
Anand et al., "Identification and characterization of VirE2-interacting protein 2 (VIP2) required for genetic transformation of plants by *Agrobacterium*," 12th International Congress on Molecular Plant-Microbe Interactions, Poster Session 10, Dec. 2005.
Anand et al., "VIP2- a VirE2 interacting protein is required for *agrobacterium* T-DNA integration in plants," *Plant Cell*, 19:1695-1708, 2007.
Anand et al., "VIP2- and VirE2 interacting protein 2 is required for genetic transformation of plants by *Agrobacterium tumefaciens*," Indiana University, Bloomington, Indiana, Jul. 31-Aug. 2, 2005, Abstract.
Anand et al., "VIP2- and VirE2 interacting protein 2 is required for genetic transformation of plants by *Agrobacterium tumefaciens*," Indiana University, Bloomington, Indiana, Jul. 31-Aug. 2, 2005, Presentation materials.
Ballas et al., "Nuclear localization signal binding protein from arabidopsis mediates nuclear import of *Agrobacterium* VirD2 protein," *Proc. Natl. Acad. Sci.*, 94:10723-10728, 1997.
Cascales et al., "Definition of a bacterial type IV secretion pathway for a DNA substrate," *Science*, 304:1170-1173, 2004.
Christie, "Type IV secretion: the *Agrobacterium* VirB/D4 and related conjugation systems," *Biochim Biophys Acta*, 1694(1-3):219-234, 2004.
Collart et al., "CDC39, an essential nuclear protein that negatively regulates transcription and differentially affects the constitutive and inducible HIS3 promoter," *EMBO J.*, 12(1):177-186, 1993.
Collart et al., "NOT1(CDC39), NOT2(CDC36), NOT3, and NOT4 encode a global-negative regulator of transcription that differentially affects TATA-element utilization," *Genes Dev.*, 8:525-537, 1994.
Collart et al., "The eukaryotic Ccr4-not complex: a regulatory platform integrating mRNA metabolism with cellular signaling pathways," *Prog Nucleic Acid Res Mol Biol.*, 77:289-322, 2004.
Collart, "Global control of gene expression in yeast by the Ccr4-Not complex," *Gene*, 313-1-16, 2003.
Frolov et al., "Regena (Rga), a drosophila homolog of the global negative transcriptional regulator CDC36 (NOT2) from yeast, modifies gene expression and suppresses position effect variegation," *Genetics*, 148:317-330, 1998.
Gelvin, "*Agrobacterium*-mediated plant transformation: the biology behind the "gene-jockeying" tool," *Microbiology and Molecular Biology Reviews*, 67(1):16-37, 2003.
GenBank Accession No. AF225983, dated Jul. 19, 2001.
GenBank Accession No. AF295433, dated Jan. 2, 2001.
GenBank Accession No. AK117230, dated Feb. 14, 2004.
GenBank Accession No. BG130671, dated Jan. 31, 2001.
GenBank Accession No. DQ000202, dated Jul. 2, 2007.
GenBank Accession No. NM_125363, dated May 22, 2008.
GenPept Accession No. NP_563795, dated May 22, 2008.
GenPept Accession No. NP_568361, dated May 22, 2008.
Guralnick et al., "Transport of DNA into the nuclei of *Xenopus* oocytes by a modified VirE2 protein of *Agrobacterium*," *The Plant Cell*, 8:363-373, 1996.
Li et al., "Involvement of KU80 in T-DNA integration in plant cells," *PNAS*, 102(52):19231-19236, 2005.
Liu et al., "The NOT proteins are part of the CCR4 transcriptional complex and affect gene expression both positively and negatively," *EMBO J.*, 17:1096-1106, 1998.
Mysore et al., "An arabidopsis histone H2A mutant is deficient in *Agrobacterium* T-DNA integration," *PNAS*, 97:948-953, 2000.
Oberholzer et al., "Characterization of NOT5 that encodes a new component of the Not protein complex," *Gene*, 207:61-69, 1998.
Tian et al., "High-throughput fluorescent tagging of full-length arabidopsis gene products in planta," *Plant Physiol.*, 135:25-38, 2004.
Tzfira et al., "*Agrobacterium*-mediated genetic transformation of plants: biology and biotechnology," *Curr. Opin. In Biotechnol.*, 17:147-154, 2006.

(Continued)

*Primary Examiner* — David T Fox
(74) *Attorney, Agent, or Firm* — SNR Denton US LLP

(57) ABSTRACT

The invention provides methods and compositions for enhancing the efficiency of *Agrobacterium*-mediated transformation of host cells such as plant cells. Plant expression constructs comprising a gene encoding a VIP2 or VIP2-like polypeptide are provided, as well as methods for utilizing such constructs to enhance *Agrobacterium*-mediated transformation efficiency.

17 Claims, 20 Drawing Sheets

OTHER PUBLICATIONS

Tzfira et al., "Increasing plant susceptibility to *Agrobacterium* infection by overexpression of the arabidopsis nuclear protein VIP1," *Proc. Natl. Acad. Sci.*, 99(16)10435-10440, 2002.

Tzfira et al., "VIP1, an arabidopsis protein that interacts with *Agrobacterium* VirE2, is involved in VirE2 nuclear import and *Agrobacterium* infectivity," *The EMBO J.*, 20(13):3596-3607, 2001.

UniProtKB/TrEMBL Q8GZ37, dated Jul. 22, 2008.

UniProtKB/TrEMBL Q9FPW4, dated Jul. 22, 2008.

Vergunst et al., "Recognition of the *Agrobacterium tumefaciens* VirE2 translocation signal by the VirB/D4 transport system does not require VirE1," *Plant Physiology*, 133:978-988, 2003.

Vergunst et al., "VirB/D4-dependent protein translocation from *Agrobacterium* into plant cells," *Science*, 290(5493):979-982, 2000.

Walter et al., "Visualization of protein interactions in living plant cells using biomolecular fluorescence complementation," *The Plant J.*, 40:428-438, 2004.

Wang et al., "Genomewide comparative analysis of alternative splicing in plants," *PNAS*, 103:7175-7180, 2006.

\* cited by examiner

```
N. benthamiana VIP2  ---------------------------------------------------MQGTL
   Arabidopsis VIP2  ---------------------------------------------------MQGTL
   Arabidopsis NOT2  ------------------------------------------------------
            Rice NOT2 MSGLLNSNLNNSASNLQDSTGRPFTGSFSQQSGSVPGGFHHSGLHNNHGSLNMPNMPGSF
            Mouse NOT2 ----------------------------------------------MVRTDGHTLSE
            Human NOT2 ----------------------------------------------MVRTDGHTLSE N. benthamiana VIP2  TSRNTAINNVPSSGVQQSGNNLSGGRFVPNNLPSALSQIPQGNSHGHSGMTSRGGTSVVG
   Arabidopsis VIP2  TSRNSSMNSIPSAGVQQPNGSFSSGRFASKNLPVNLSQLSHGSSHGHSGIPSRGL-NVVG
   Arabidopsis NOT2  ------------------------------------MSHGSSHGHSSGLTNRGG------
            Rice NOT2 SQRNAAMSGLPSSGVQQPGGSMP-GRFASNNLPVGMSQIPHGHSGVGSRGLNVGG------
            Mouse NOT2 KRNYQ------------------------------------MLASPSTSG----------
            Human NOT2 KRNYQVTNSMPGASRKKFVESSVDSDYHDENMYYSQSSMFPHRSEKDMLASPSTSG-----

N. benthamiana VIP2  NPGYSSNTNGVGGSIPGILPTPAAIGNRSSVPGLGVSPILGNAGPRMTNSVGSNIVGGGST
   Arabidopsis VIP2  NPGFSSNANGVGGSIPGILSTSAGLSNRNSVPGMGISQLLGNSGPRITNSMGNNMVGLGNL
   Arabidopsis NOT2  ----------------------------LGVSPILGNVGSRMTSSMGNMVGLGTM
            Rice NOT2 -GPAFSSSLNIGGTIQGLSSNLGAGGSRNSVPGMSVSPSLGNLGPRITGSVSNIVGGGSSI
            Mouse NOT2 ----------------QLSQFGASLYGQQSALGLPMRGMSNGTPQLNRSLSQ
            Human NOT2 ----------------QLSQFGASLYGQQSALGLPMRGMSNGTPQLNRSLSQ N. benthamiana VIP2  GRSISSGAGLSVPGLASRLNMNANSGSGNLNVQGPNRLMSGVLQQASPQVLSMLGNSYPA
   Arabidopsis VIP2  GBNISSG-GLSIPGLSSRLNLAANSGSGLN-VQGQNRMMGGVLPQGS-QVMSMLGNSYHP
   Arabidopsis NOT2  GRTLSSGGKGLSIPSLGSBINLAVRSGSGNI---GQNRNMMGGVLPQGSPQVLSMLGNSYPS
            Rice NOT2 GBNISSG-GLSVPSIASRMNLSGRVGSGGINVQGSGRMMNGILQQGSPQMLNMMGSLYPT
            Mouse NOT2 GTQLPSHVTPTTGVPTMSLRTPPSPSRGILPMNPRNMMNHSQVGQGI-VIPSRTNSMSSS
            Human NOT2 GTQLPSHVTPTTGVPTMSLRTPPSPSRGILPMNPRNMMNHSQVGQGI-GIPSRTNSMSSS N. benthamiana VIP2  GGS-LSQSHVQAIGNFNSMGLINDVNSNGGSRSDIN-DFYQLSSRPSSAGGPQGQLSSLR
   Arabidopsis VIP2  GGGPLSQNHVQSVNR-----MMLSDHPNDSSLYDINNDFQLTSRPGSAGGTQSHLGSLR
   Arabidopsis NOT2  AGG-LSQSHVQAMNSLSSMGLLNDMNSHDTSPSDINNDFQLTSRPSSAGG-SQGQLGSRL
            Rice NOT2 SGGSLSQNQIQGGNN--SLGSMSMLHDASDGAPYDMS-DFYQLTGRPSSAGGPQGSQYSSIR
            Mouse NOT2 GLGSPNRSSPSIICMPKQQPSSQDPPFTVRSMSGFGMSRNQAFGMSRSLSSNIFNGTDGSEN
            Human NOT2 GLGSPNRSSPSIICMPKQQPSRQFFTVRSMSGFGMSRNQAFGMSRSLSSNIFNGTDGSEN N. benthamiana VIP2  KQGL--SPIVQQNQEFSIQREDFFALPGFKGGNADYAMDFHQREQLHDNTLSMKQQDRFS
   Arabidopsis VIP2  KQSLG-VFLVQQNQEFSIQSEDFPALPGYKGGNSEYPMDLRQKEQLHDSAMSMNHSQKFS
   Arabidopsis NOT2  KQSLGISPIVQQNQEFSIQNEDFFALPGYKGSSADYPMDLHHREQLHENSVLMMQSQQLS
            Rice NOT2 KQGVGVNTIVQQNQEFSIQREDFFALPGYKGNTTDYAMELHHREQLHDN-VFVMQAQQYP
            Mouse NOT2 VTGLDLSDFPALADSNRREGSGNPYPLINPLAGRAPYVGMVTKPANEQSQDFSIHNEDFP
            Human NOT2 VTGLDLSDFPALADSNRREGSGNPYPLINPLAGRAPYVGMVTKPANEQSQDFSIHNEDFP
```

FIG. 2 (continued)

```
N. benthamiana VIP2  MGRSAGFNLGGTYSSNRPQQQLQHAPSVSSGGVSFSNINNQDLLSLHGSDVFQSSHSSYQ
  Arabidopsis VIP2  MGRSGGFNLGATYSSHRPQQQPQHTSS---------------------------------
  Arabidopsis NOT2  MGRSGGFNLGSAYTSHRPQQQQHAQAVSSSGVS---------------LHGSDIPSSSHPPYH
         Rice NOT2  MSRSVGFNLGSNYPPERQQHQQQANSV---------------------------------
        Mouse NOT2  ALPGSSYKDPTSSNDDSKSNLSTSGKT---------------------------------
        Human NOT2  ALPGSSYKDPTSSNDLSKSNLNTSGKT---------------------------------

N. benthamiana VIP2  QQGGGPPGIGLRPLNSSGTVSGIGSYDQLIQQYQQHQGQSQFRLQQMGTLGQPFRQQSLK
  Arabidopsis VIP2  ---TGSLQGLGLRPLSSPNAVSSIGY-DQLIQQYQQHQQNQSQFPVQQMSSINQ-FRDSEMK
  Arabidopsis NOT2  SQTSGAPGIGLRSMNSANSITQMGYDQQLIQQYQHQQNSAQYRLQQMSAASQPFRQVGLK
         Rice NOT2  -QNAGPPNIGLRPLNSPNQTSSLGSYFQLIQQYQQPQAQNPFRLQQVSSATQSYRPQSLF
        Mouse NOT2  ----------------------------TSSTDGPKFPGDKSSTTQNNNQQKEGIQVLPDGRVT
        Human NOT2  ----------------------------TSSTDGPKFPGDKSSTTQNNNQQKEGIQVLPDGRVT N. benthamiana VIP2  SMQS-QVAPDFFGMLGLLSVIRM--SDPDLTSLALGIDLTYLGLNLSSAEMLYKTFSSPW
  Arabidopsis VIP2  STQS---EASPFCLLGLLDVLSR--SNPELTSLALGIDLTYLGLDLSSTGNLYKTFASSW
  Arabidopsis NOT2  SMQSTQSNPPRPGLLGLLSVIKM--SDPDLTSLALGIDLPYLGLNLSSTERLEKTPSSPW
         Rice NOT2  SIQGGQTFSPPYGIMGLLGVIRM--NDVDLSSLALGIDLTYLGLNLSSPDNLYKTPGSPW
        Mouse NOT2  NIPQ-GMVTDQFGMIGLLTFIRAAETDPGMVHLALSDLPTTLGLNLSSPEMLYPKFASPW
        Human NOT2  NIPQ-GMVTDQFGMIGLLTFIRAAETDPGMVHLALSDLPTTLGLNLSSPEMLYPKFASPW N. benthamiana VIP2  SNEPAK-GDPEPTVFQCYYAKQ--PPPLNQAYFSKFQLDTLFYIFYSMPKDEAQLYAANE
  Arabidopsis VIP2  TNEPAK-SEVEPTVPNCYYATE--PPPLTRASFKRFSYELLFYTFYSMPKDEAQLYAADE
  Arabidopsis NOT2  SNEPSK-VDPEPSVFQCYYAKN--PPPLHQGLFAKLLVETLFYVFYSMPKDEAQLYAANE
         Rice NOT2  SNEPAK-GEPEFHTFACYSAEQ--PPPLQPIHFQKFQTPTLFYIFYSMPRDEAQLCAASE
        Mouse NOT2  ASSPKRPQDIDFHVPSEYLTNIHIRDKLAAIKLGRYGEDLLFYLYMNGGDVLQLLAAVE
        Human NOT2  ASSPKRPQDIDFHVPSEYLTNIHIRDKLAAIKLGRYGEDLLFYLYMNGGDVLQLLAAVE N. benthamiana VIP2  LYNRSWFYRREHRLWFMRVANMEPLVKTNAYERGSYICFDPNTWETIHRDNPVLHCEMLE
  Arabidopsis VIP2  LYERSWFYRKELKVWFFRVG--EPLVRAATYERSTYEYLDPNSFKTVRSEHPVIKYELME
  Arabidopsis NOT2  LYNRSWFYRREHRLWFIRIG--EPLVKTNAYERGSYECFDPNSFEIVQRENPVLYYEMLE
         Rice NOT2  LYTRSWFYRRSVRVWSLTRIPNVEPLVRTPRYERGSYQCFDPNSWETIRRDNPVLHYDQIE
        Mouse NOT2  LFNRDWRYRREERVWITRAPGMEPTMKTNTYERSTYYPFDCLNWRKVASE-PHLEYDKLE
        Human NOT2  LFNRDWRYRREERVWITRAPGMEPTMKTNTYERGTYYPFDCLNWRKVASE-PHLEYDKLE N. benthamiana VIP2  KRPVLPQH---------
  Arabidopsis VIP2  KRPSLLQL---------
  Arabidopsis NOT2  KRPSISQDSQH------
         Rice NOT2  KKPAIPSSQNVR-----
        Mouse NOT2  ERPHLPSTFNYNPAQQAF
        Human NOT2  ERPHLPSTFNYNPAQQAF
```

FIG. 7
A
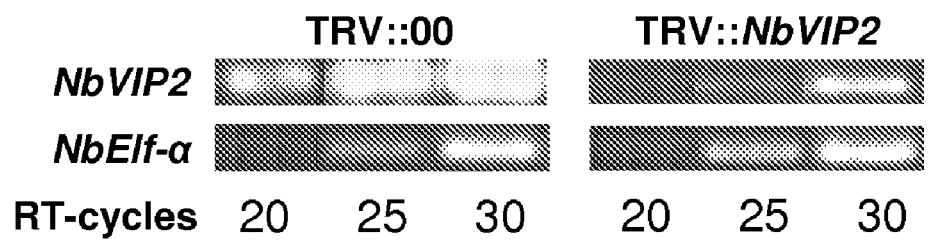
B
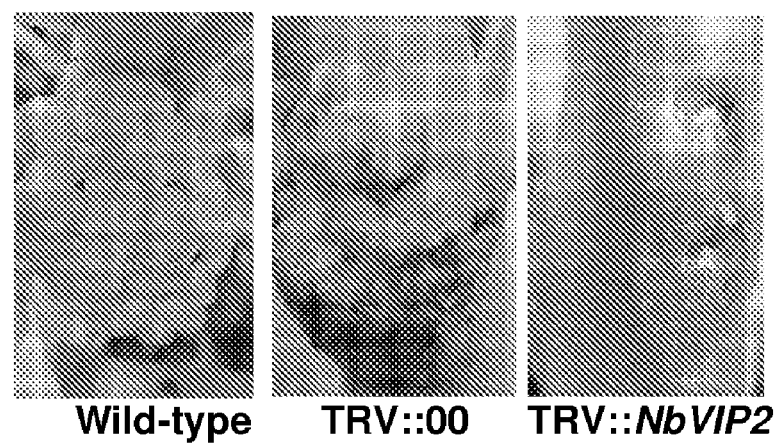

FIG. 13
A
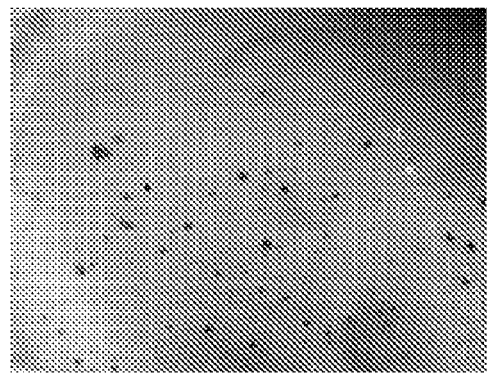
TRV::00
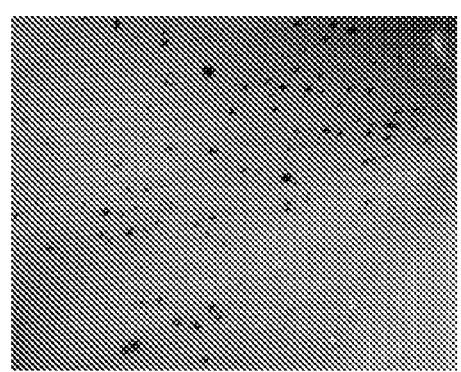
TRV::*NbVIP2*
B
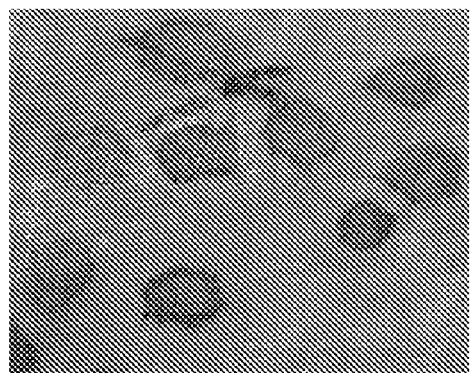
TRV::00
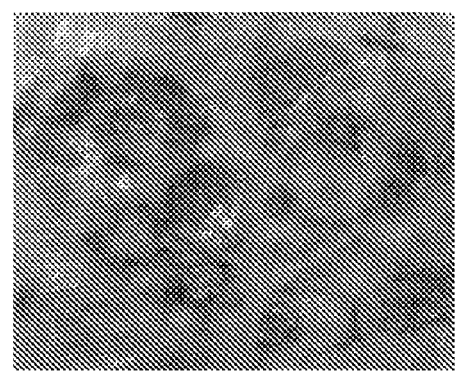
*TRV::NbVIP2*

METHOD FOR AGROBACTERIUM-MEDIATED TRANSFORMATION OF PLANTS

This application claims the priority of U.S. Provisional Patent Application Ser. No. 60/836,461, filed Aug. 7, 2006, the entire disclosure of which is specifically incorporated herein by reference.

The Government may own rights in the invention pursuant to National Science Foundation Grant No. 0445799.

BACKGROUND OF THE INVENTION

1. Field of the Invention

The present invention relates generally to the field of molecular biology. More specifically, the invention relates to methods and compositions for more efficiently transforming cells.

2. Description of the Related Art

*Agrobacterium* sp., including *A. tumefaciens*, are soil borne phytopathogenic bacteria that cause crown gall disease in plants. This disease is a manifestation of the transfer, integration and expression of oncogenes on a specific region of the transferred DNA (T-DNA) in susceptible hosts (Amand and Mysore, 2005; Gelvin, 2003; Tzfira and Citovsky, 2006). The mechanism utilized by *A. tumefaciens* and related species to transfer T-DNA into plant cells also allows engineering of plants with engineered DNA, for instance comprising a transgene of interest.

In addition to the T-DNA, several *Agrobacterium* encoded proteins, such as VirD2, VirE2, VirE3 and VirF are also translocated into plants (Christie, 2004; Cascales and Christie, 2004; Vergunst et al., 2003). It is thought that *A. tumefaciens* separately translocates the VirD2-T-strand and VirE2 and that the VirD2-T-strand-VirE2 complex (T-complex) assembles in the plant cell (Cascales and Christie, 2004; Vergunst et al., 2000). VirD2 remains tightly attached to the 5' end of the nicked T-DNA region, while the remaining single stranded DNA (ssDNA) is covered stoichiometrically with VirE2, protecting the T-strand from exonucleolytic degradation in planta.

The T-complex is subsequently imported into the nucleus most likely through interactions with other host proteins such as VIP1 (Tzfira et al., 2001) and importin α (Ballas and Citovsky, 1997). Once inside the plant cell, the T-complex is stripped of its proteins possibly through targeted proteolysis involving the SCF$^{virF}$ ubiquitin complex (Tzfira et al., 2004). The T-DNA most-likely relies on host DNA repair machinery for its conversion into double stranded (ds) T-DNA intermediates and their recognition by proteins like KU80 (Li et al., 2005) and histone H2A (Li et al., 2005; Mysore et al., 2000) for integration into the host chromosome.

Several plant proteins that interact with the T-DNA nucleoprotein complex have been identified, for instance via yeast two-hybrid assays. These include VIP1 (U.S. Patent Publ. 20030233676, GenBank AF225983; Tzfira et al., 2001) and VIP2 (Tzfira and Citovsky, 2000; GenBank AF295433; GenBank AK117230; GenBank DQ000202; GenBank BG130671). However, the mechanism by which VIP2 acts in relation to *Agrobacterium*-mediated DNA transfer has not been known. Further, methods to utilize VIP2 to enhance such DNA transfer have also not been known.

SUMMARY OF THE INVENTION

In one aspect, the invention provides a transgenic plant or part thereof transformed with a polynucleotide sequence that encodes a VIP2 polypeptide or VIP2-like polypeptide, operably linked to a heterologous promoter. The promoter operably linked to the gene encoding the VIP2 polypeptide or VIP2-like polypeptide may be a promoter functional in a plant cell. In certain embodiments, the VIP2 polypeptide may be encoded by a nucleic acid sequence selected from the group consisting of: (a) a nucleic acid sequence encoding the polypeptide of SEQ ID NO:1, 2, or 4; (b) a nucleic acid comprising the sequence of SEQ ID NO:3 or 26; (c) a nucleic acid hybridizing to SEQ ID NO:3 or 26 under conditions of 0.15M NaCl and 70° C.; (d) a nucleic acid sequence encoding a protein with VIP2 activity and at least 85% sequence identity to SEQ ID NO:3 or 26 over the full length of the coding sequence; and (e) a nucleic acid sequence complementary to the nucleic acid sequences of (a), (b), (c), or (d).

In certain embodiments, the invention also provides a cell or seed of the transgenic plant, or of a subsequent generation of the transgenic plant, wherein the cell or seed comprise the VIP2 or VIP2-like polypeptide, or the polynucleotide sequence encoding the VIP2 or VIP2-like polypeptide.

In another aspect, the invention provides a method of enhancing the efficiency of *Agrobacterium*-mediated transformation of a host cell, comprising expressing in the cell a heterologous polynucleotide encoding VIP2, operably linked to a heterologous promoter functional in a plant cell. In the method, the host cell may be transformed with an *Agrobacterium* transformation vector comprising a T-DNA sequence simultaneously with the VIP2 or VIP2-like encoding sequence or following transformation of the host cell with a VIP2 or VIP2-like coding sequence. For example, the transforming may be carried within any time period in which an increase in transformation efficiency is observed. In certain embodiments the host cell is stably transformed with the polynucleotide sequence.

In specific embodiments, the host cell is defined as expressing the VIP2 polypeptide at the time the host cell is transformed by *Agrobacterium*-mediated transformation. In the method, the host cell may be a plant cell and may be a dicot or monocot plant cell. Non-limiting examples of dicots include cotton, soybean, rapeseed, sunflower, tobacco, sugarbeet, or alfalfa. Non-limiting examples of monocots include corn, rice, wheat, sorghum, barley, oat, and turfgrass. The host cell may also be, for example, a fungal cell.

In still another aspect, the invention provides a method of transformation comprising a) providing a cell prepared by a method of the invention to express heterologous VIP2; and b) transforming the cell with a selected DNA by *Agrobacterium*-mediated transformation, wherein the efficiency of transformation is increased relative to a cell not expressing a transgenic sequence encoding VIP2 function. In the method, the host cell may be a plant cell and may be a dicot or monocot plant cell. Non-limiting examples of dicots include cotton, soybean, rapeseed, sunflower, tobacco, sugarbeet, or alfalfa. Non-limiting examples of monocots include corn, rice, wheat, sorghum, barley, oat, and turfgrass. The host cell may also be, for example, a fungal cell The use of the word "a" or "an" when used in conjunction with the term "comprising" in the claims and/or the specification may mean "one," but it is also consistent with the meaning of "one or more," "at least one," and "one or more than one."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the invention. The invention may be better understood by reference to one or more of these drawings in combination with the detailed description of specific embodiments presented herein:

FIG. 1A-1F. AtVIP2-VirE2 and AtVIP2-AtVIP1 interactions in the two-hybrid system and amino acid sequences of AtVIP2 and NbVIP2. (A) AtVIP2+VirE2. (B) AtVIP2+AtVIP1. (C) AtVIP2+human lamin C. (D) AtVIP2+topoisomerase I. (E) β-galactosidase assay; from left to right: AtVIP2+VirE2, AtVIP2+AtVIP1, AtVIP2+human lamin C, AtVIP2+topoisomerase I. Cells shown in panels A-D were grown in the absence of histidine, tryptophan and leucine, and cells shown in panel E were grown in the absence of tryptophan and leucine. (F) Multiple sequence alignment by CLUSTAL W (1.81) of amino acid sequences encoding full length proteins for AtVIP2 and NbVIP2. The identical amino acids are shown in red, conserved amino acids in blue, semi-conserved amino acids in green and the divergent amino acids in black. The shaded area represents the C-terminal NOT domain between the two proteins.

FIG. 2. Alignment of proteins with the NOT domain from *Arabidopsis* and other genera.

FIG. 7. (A) Semi-quantitative RT-PCR analyses confirm the silencing of NbVIP2 expression in the silenced plants. Total RNA was extracted from the leaf tissues three weeks post-TRV inoculation and was subjected to RT-PCR. PCR products were subjected to electrophoreses on an agarose gel, stained with ethidium bromide and photographed. PCR products for elongation factor 1-α (NbEf1α) were used as a loading control for the RT-PCR amplification. (B) In planta tumor assays. A fragment corresponding to *N. benthamiana* VIP2 gene was cloned into pTRV2 and two-week old seedlings of *N. benthamiana* were agroinfiltrated with pTRV1 and pTRV2::NbVIP2. The stems of the gene-silenced plants (NbVIP2), TRV::00 inoculated and no virus inoculated plants (wild-type) were inoculated, with a tumorigenic *A. tumefaciens* strain A348 (contains octopine type Ti plasmid) 3-wks post-TRV inoculation. Tumors on shoots were scored after four weeks of *Agrobacterium* infection. Smaller tumors and in some cases no tumors were detected in the NbVIP2 silenced plants in comparison to the TRV::00 and control plants.

Leaf disks from the silenced and TRV::00 plants were infected with a non-tumorigenic *A. tumefaciens* strain GV2260 harboring the binary vector pCAS1 and incubated on callus inducing medium (CIM) with glufosinate ammonium (GF). Pictures were taken four weeks after inoculation. (D) Effect of VIP2 gene silencing on cell division. The effect of gene silencing on cell division was evaluated by placing un-inoculated leaf disks from the silenced and TRV::00 plants on a non-selective CIM and photographs were taken four weeks after incubation. All the experiments were done with at least five biological replicates, repeated two times and the results were consistent among the replicates. Asterisk denote significant difference compared to controls using Fisher's LSD test at P=0.05.

Figure 9:
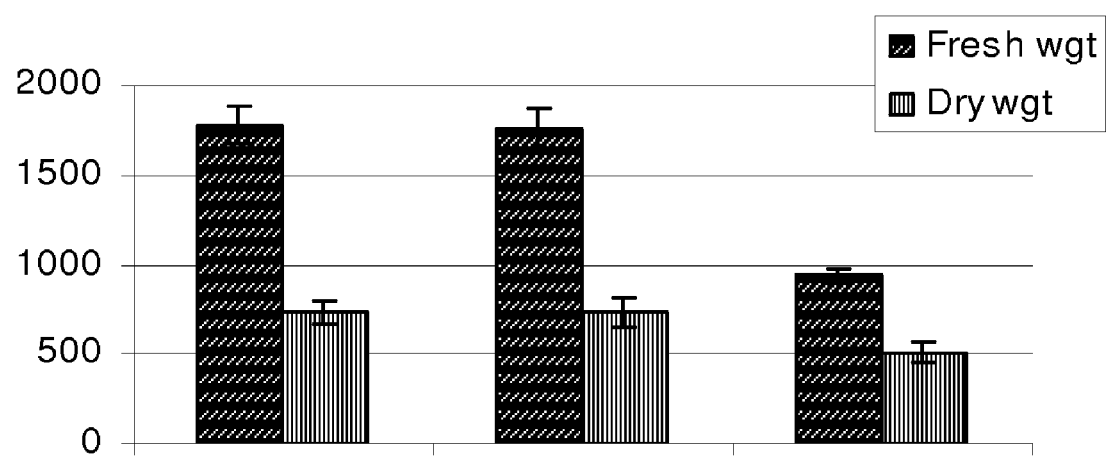

FIG. 9. Quantification of tumors in NbVIP2 silenced plants. Three weeks post-TRV inoculation, equal number of leaf discs from NbVIP2 silenced plants, TRV::00 infected plants and wild-type *N. benthamiana* plants were inoculated with the oncogenic *A. tumefaciens* strain A348, and allowed to produce leaf tumors on a basal selection media with antibiotics. The fresh and dry weight of tumors incited on the leaf discs were quantified 4-wks post *Agrobacterium* inoculation.

Figure 10:
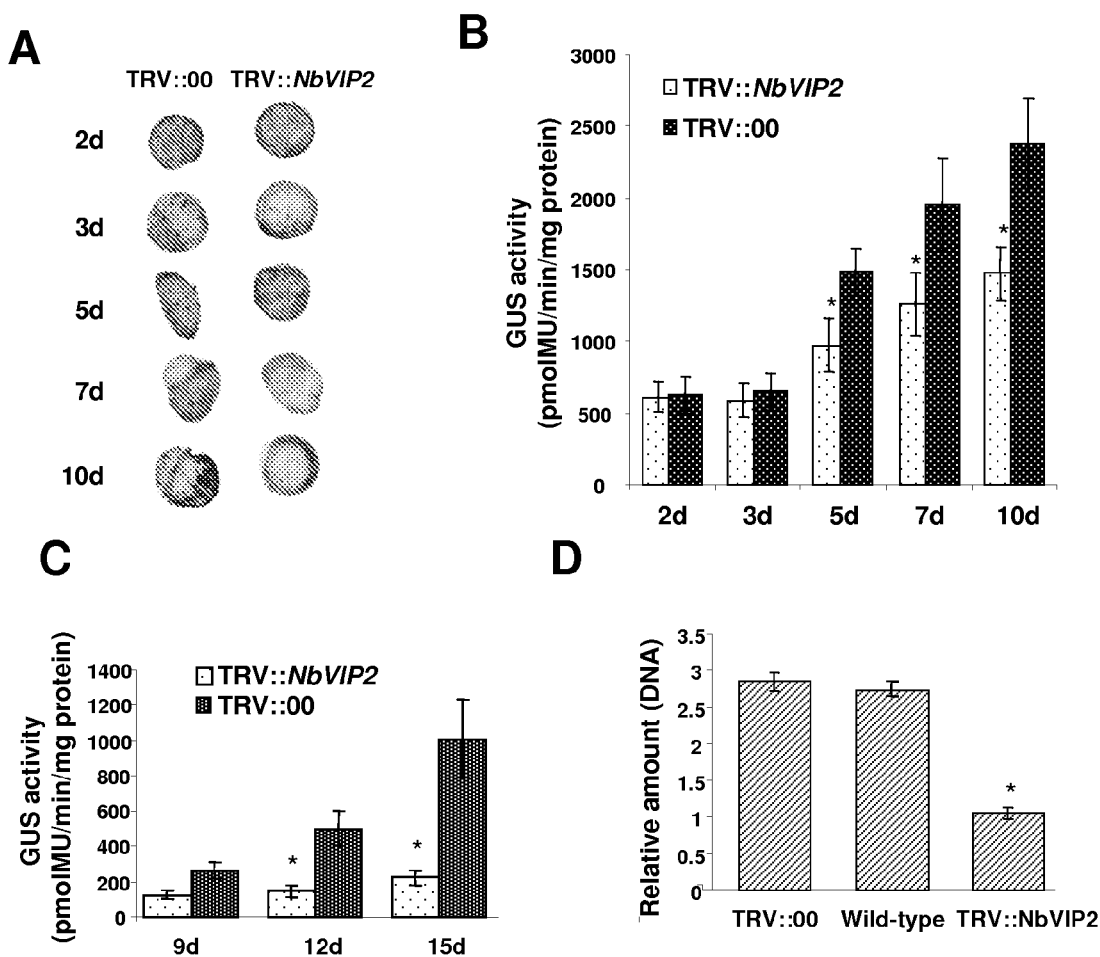

FIG. 10. Transient transformation and T-DNA integration assays in NbVIP2 silenced plants. (A) Transient transformation assay. Leaf disks of the NbVIP2 silenced and TRV::00 plants were inoculated with *Agrobacterium* strain carrying the uidA-intron gene within the T-DNA. The inoculated leaves were periodically collected and stained with X-Gluc. (B) Quantification of GUS activity. Leaf disks from the experiment in panel A were collected periodically and were used for measuring the fluorescence of 4-methylumbelliferone (4-MU). (C) T-DNA integration assay. Leaf disks from TRV::00 and NbVIP2 silenced plants were inoculated with *Agrobacterium* strain carrying a promoterless uidA-intron gene and 35S::luc-intron gene within the T-DNA. Leaf disks were periodically collected and GUS activity was measured as described above. (D) Quantification of T-DNA integration. The amounts of integrated T-DNA molecules in the genomic DNA extracted from calli that were generated from leaf disks transformed with *Agrobacterium* strain carrying the uidA-intron gene within the T-DNA were measured by quantitative PCR. The uidA gene transcripts in calli derived from NbVIP2 silenced plants are represented in relative amounts in comparison to an average T-DNA amount in the calli derived from wild-type and TRV::00 plants. All the experiments were done with at least five biological replicates and repeated two times. Asterisks denote value which are significantly different between the two treatments by ANOVA at P=0.05.

Figure 11:
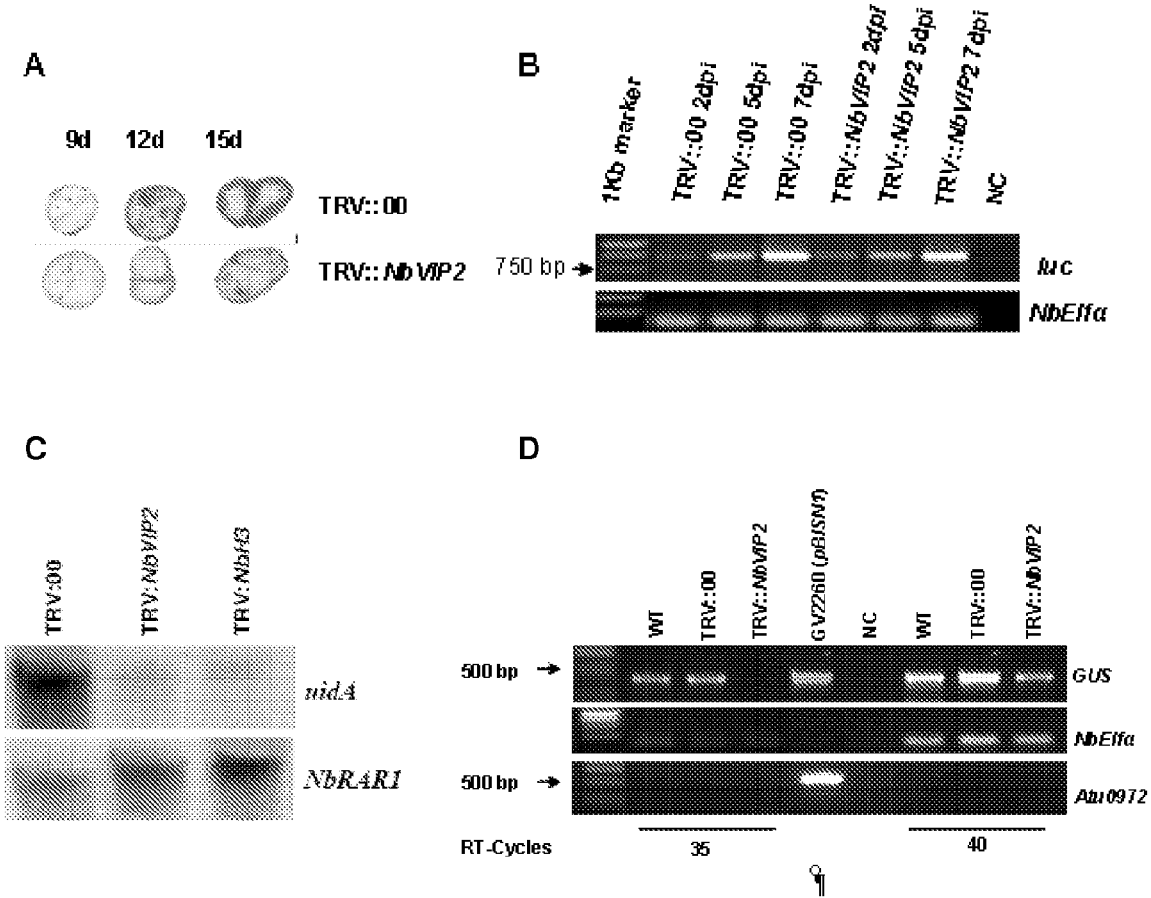

FIG. 11. T-DNA integration assay. (A) The leaf disks from TRV::00 plants and NbVIP2 silenced plants were inoculated with a disarmed *A. tumefaciens* strain GV2260 containing the binary vector pKM1 with a promoterless gusA-intron gene and 35S::luc-intron gene within the T-DNA. Leaf disks were periodically collected and stained with X-Gluc for GUS expression. (B) Expression of the luc gene in the same leaf disks inoculated with *Agrobacterium* strain GV2260 containing the binary vector pKM1 for NbVIP2 silenced and TRV::00 inoculated plants by semi-quantitative RT-PCR. (C) T-DNA integration in the NbVIP2 silenced and TRV:00 infected plants. Genomic DNA extracted from the suspension cultures derived the from calli generated from NbVIP2 silenced and TRV:00 infected leaf segments infected with the non-tumorigenic strain *A. tumefaciens* GV2260 carrying pBISN1 were subjected to electrophoresis through a 0.8% agarose gel, blotted onto a nylon membrane, and hybridized with a uidA gene probe. After autoradiography, the membrane was stripped and rehybridized with the NbRAR1 gene probe to compare the amount of DNA in each lane. (D) Semi-quantitative PCR analyses to determine the amount of integrated T-DNA. The leaf disks derived from NbVIP2 silenced plants and TRV::00 inoculated *N. benthamiana* plants were infected with a non-tumorigenic *A. tumefaciens* strain GV2260 harboring the binary vector pBISN1.The inoculated leaf disks were incubated in CIM without any selection and were collected at 21 dpi. DNA was isolated from the calli and was PCR amplified with primers specific to GUS or elongation factor α (NbEf1 α) or an *Agrobacterium* gene (Atu0972). WT, Wild-type; NC, no template control.

Figure 12:
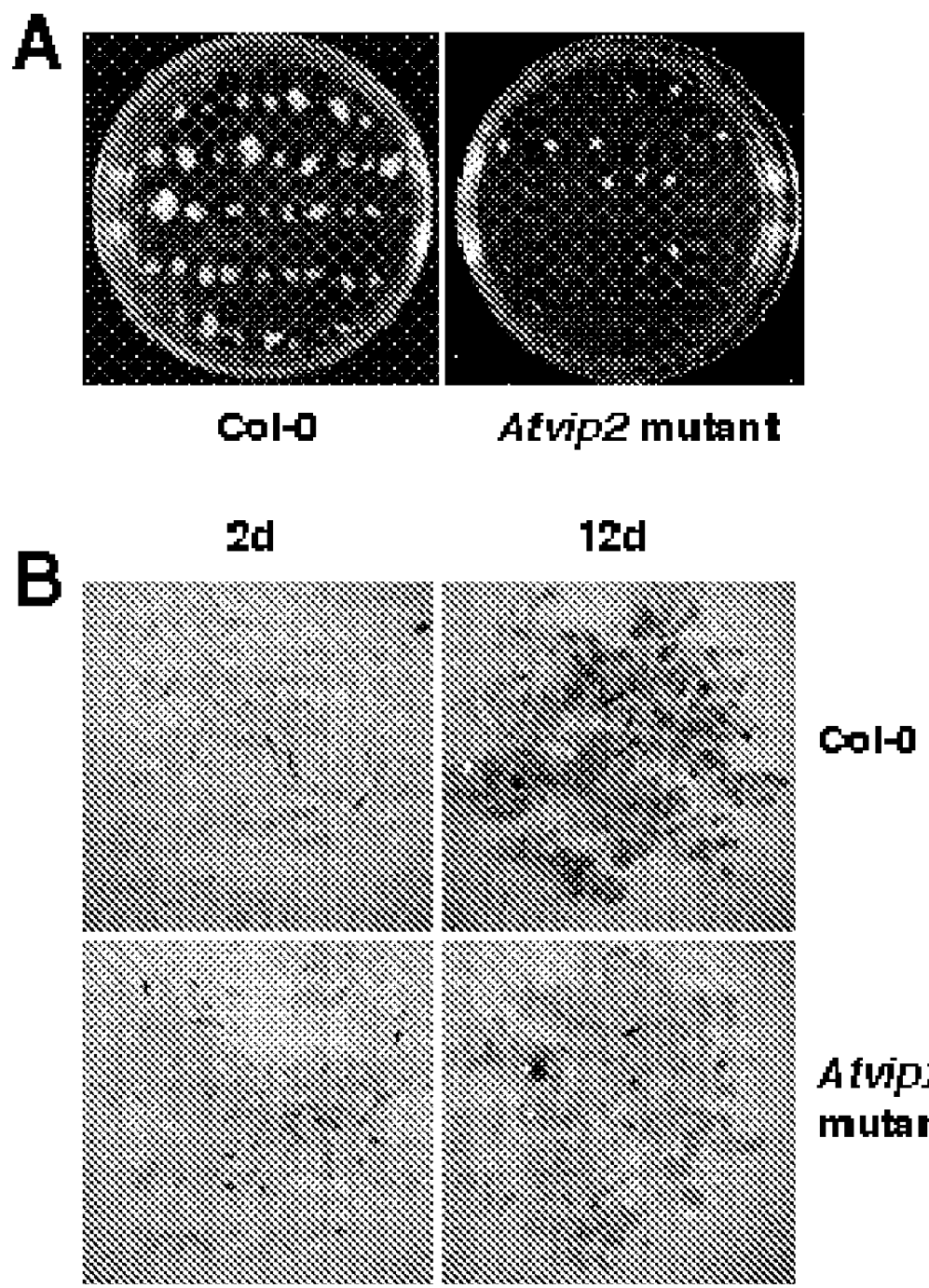

FIG. 12. Transformation assays in Atvip2 mutant. (A) Stable transformation assay. Roots of wild-type and Atvip2 mutant plants were infected with a tumorigenic *A. tumefaciens* strain A208, and tumors incited on the roots were visualized and scored 4 weeks post infection. (B) Transient and stable GUS expression. Roots of the wild-type and Atvip2 mutant plants were inoculated with a disarmed *Agrobacterium* strain carrying the uidA-intron gene within the T-DNA. The inoculated roots were periodically collected and stained with X-Gluc. All the experiments were repeated two times.

FIG. 13. NbVIP2 silenced plants can also be transiently transformed by alternate methods. (A) Transient expression of GFP by particle bombardment in NbVIP2 silenced and TRV::00 inoculated leaves of *N. benthamiana*. Leaves from the NbVIP2 silenced plants and TRV::00 inoculated plants were biolistically transformed with a plant transformation vector pAHC20 carrying 35S::GUS cassette. The transformed leaves were stained for GUS reporter gene expression 48-h after bombardment. No qualitative differences were observed in the number of GFP spots detected on the NbVIP2 silenced and TRV::00 infected plants. (B) Transient GUS expression in the NbVIP2 silenced and TRV::00 inoculated leaves of *N. benthamiana*. Three weeks post-TRV inoculation the NbVIP2 silenced and TRV::00 leaves were agro-infiltrated (using a needle-less syringe) with *A. tumefaciens* strain GV2260 containing the binary vector pBISN1 (containing on its T-DNA a gusA-intron gene). The infiltrated leaves were collected three days post infiltration and stained with X-Gluc. No qualitative differences were observed for transient GUS expression in the NbVIP2 silenced plants and TRV::00 inoculated plants.

Figure 14:
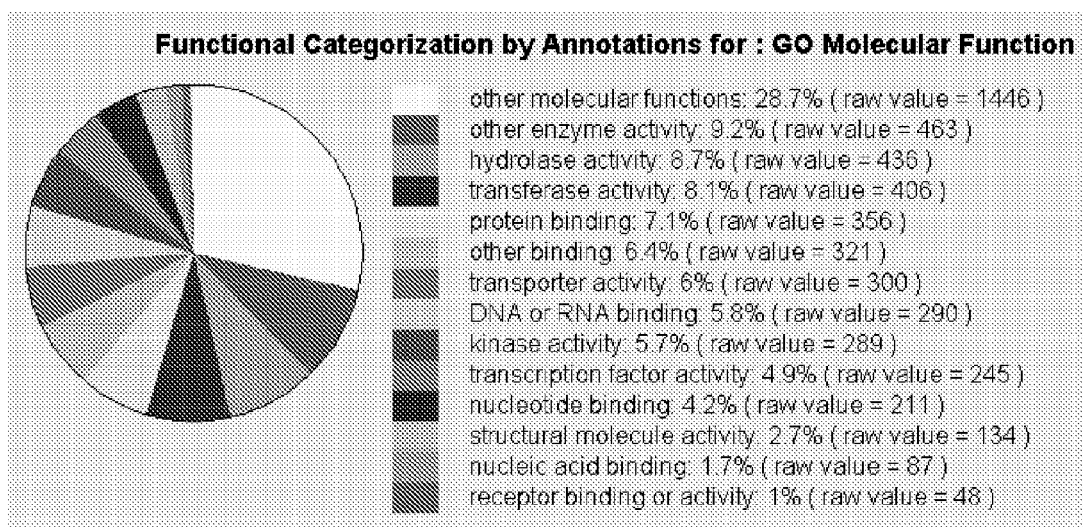

FIG. 14. Transcriptome analyses of wild-type Col-0 and At vip2 mutant. Classification of the 4241 differentially expressed genes between wild-type Col-0 and At vip2 on the basis of their molecular functions.

Figure 15:
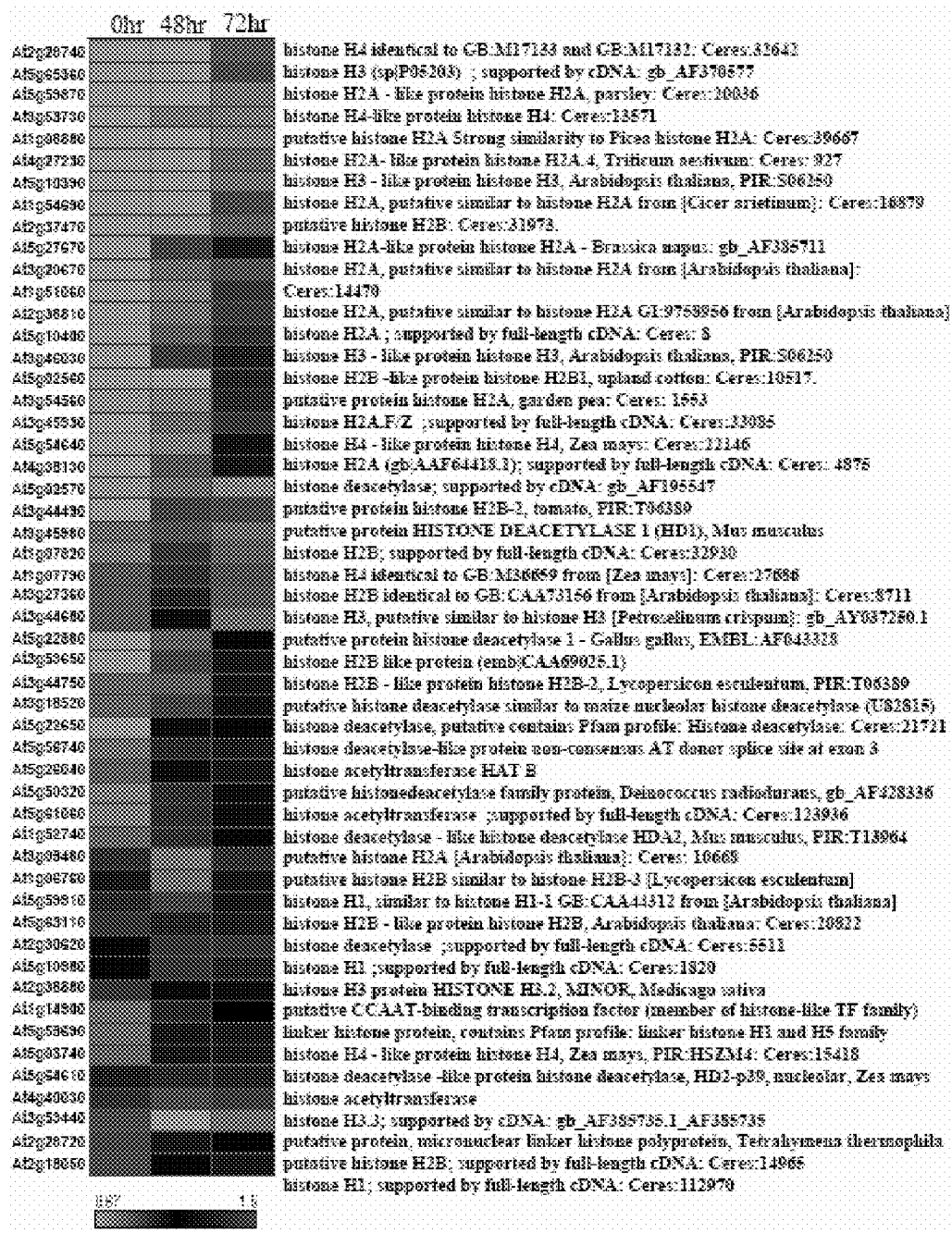

FIG. 15. Expression profile for the 52 differentially expressed histone or histone-associated genes represented in the ATH1 gene chips in the Col-0 and At vip2. Color code represents expression values of ratio between At vip2 and Col-0; wherein red and green indicate up- and down-regulation of genes, respectively. Each horizontal line displays the expression data for one gene. Data were clustered with correlation using TMEV.

Figure 16:
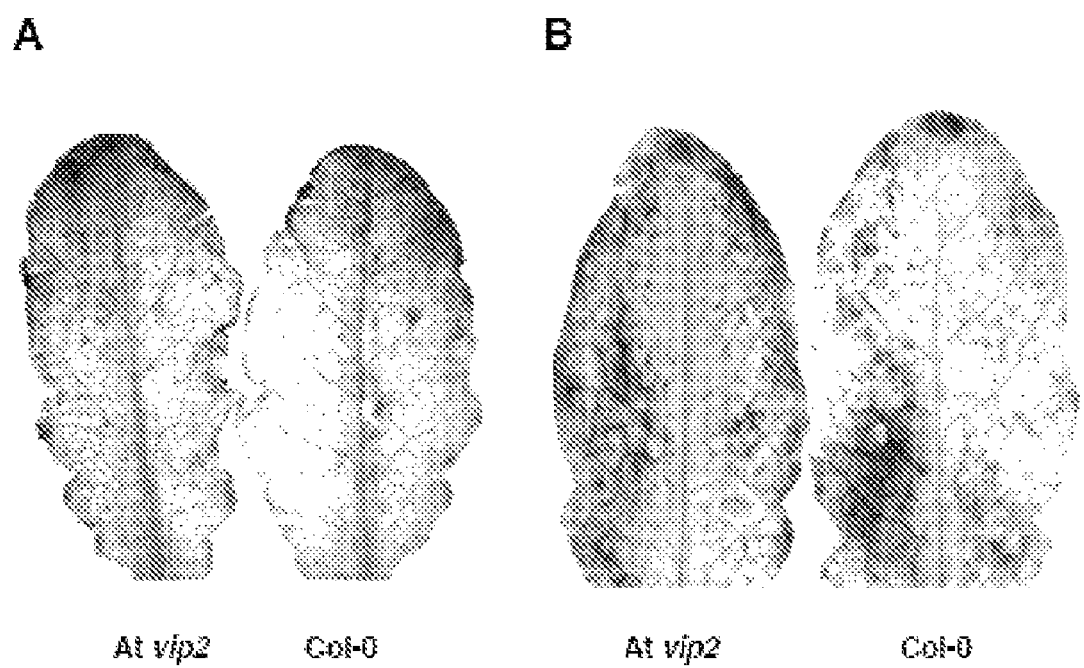

FIG. 16. Transient expression of uidA-intron gene in leaves of *Arabidopsis* plants transformed with *A. tumefaciens* GV3101 containing the binary vector pBISN1 for transcriptome analyses. Leaves of Col-0 and At vip2 were agro-infiltrated with *A. tumefaciens* GV3101 (containing on its T-DNA a uidA-intron gene). The infiltrated leaves were collected 42 hr (A) and 72 hr post infection (B) and stained with X-Gluc. No qualitative differences were observed for transient GUS expression in the At vip2 and Col-0 plants. Similarly infected leaves were used to compare the expression profile of At vip2 and Col-0 in response to *Agrobacterium* infection.

Figure 17:
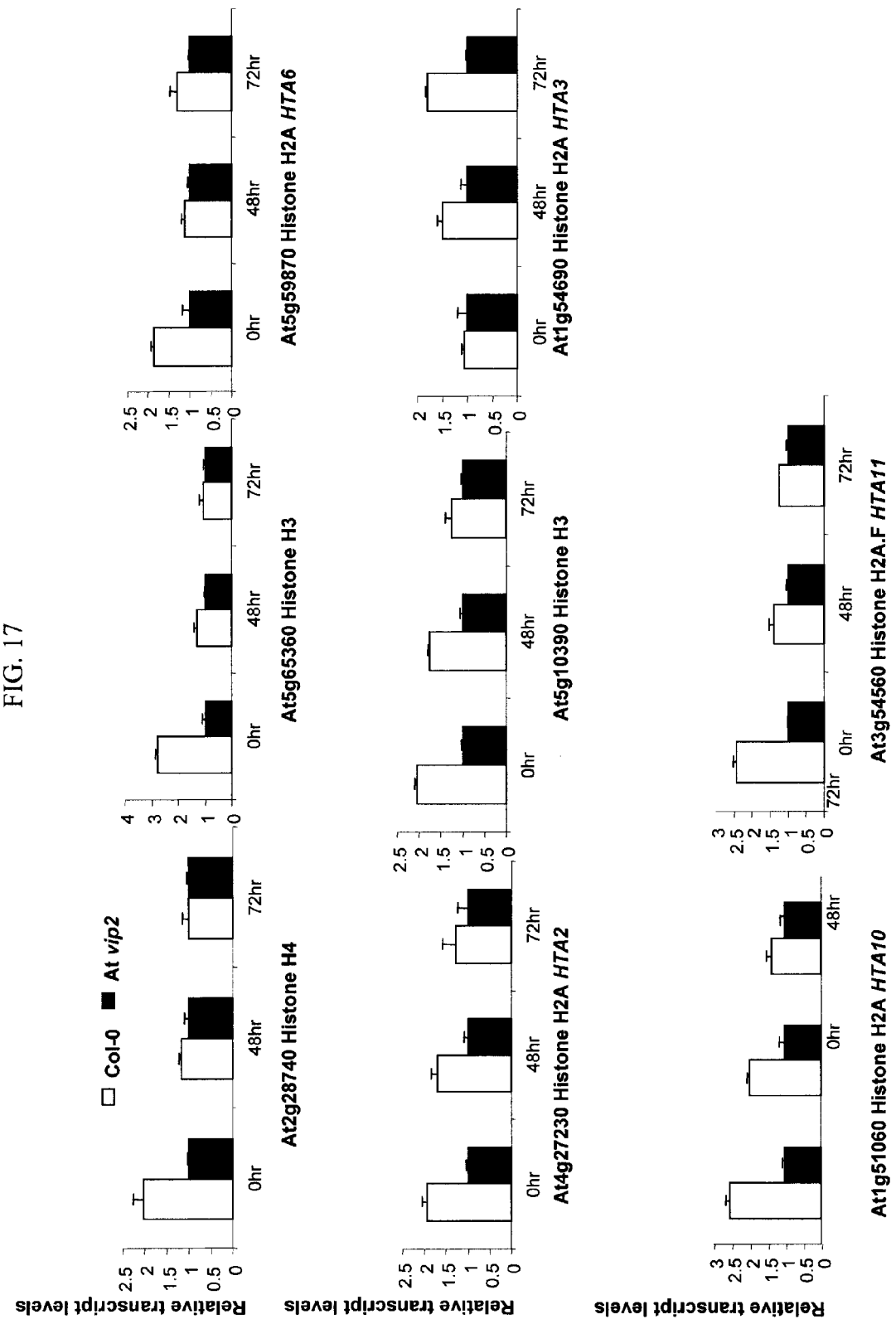

FIG. 17. Validation of the microarray data by real-time quantitative reverse transcriptase PCR (qRT-PCR). Eight different histone genes that had less transcript abundance in At vip2 when compared to Col-0, based on microarray experiments, were selected for validation. The data represent the average of three biological replicates including three technical replicates for each biological replicate with standard error values shown as error bars.

Figure 18:
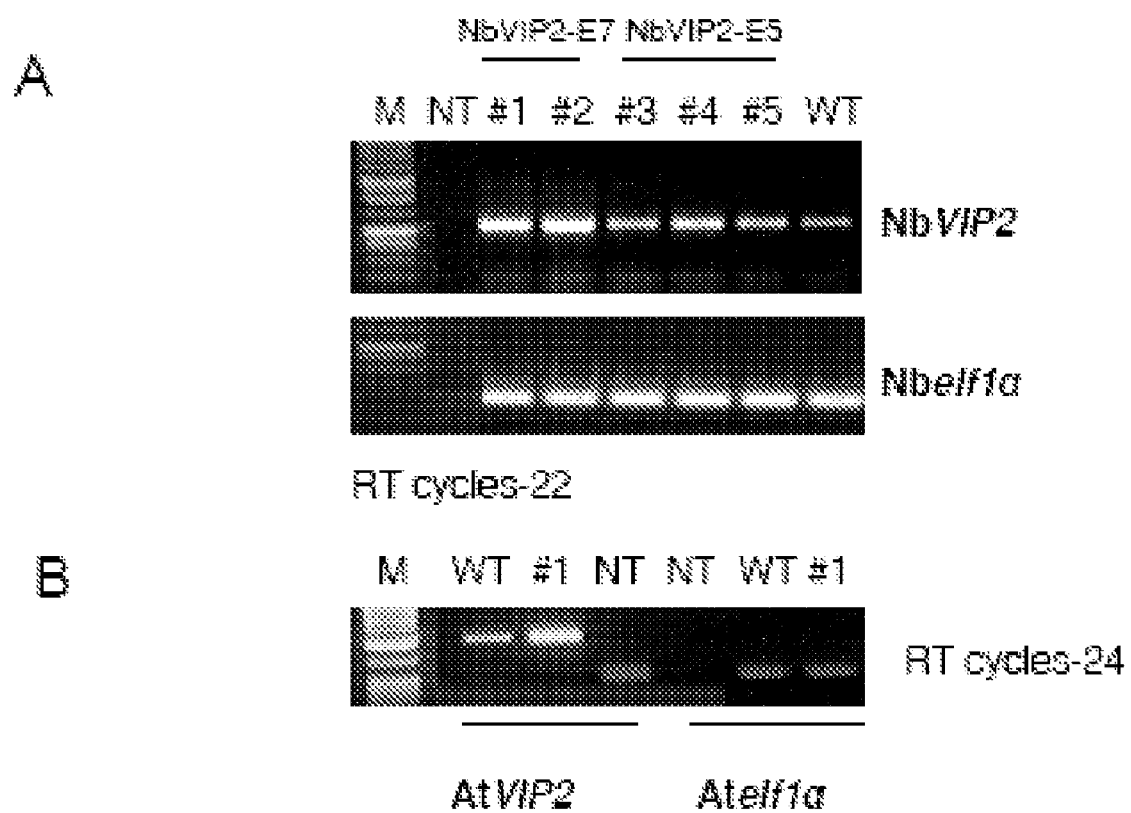

FIG. 18. The relative expression of VIP2 in the transgenic lines of *N. benthamiana* (A) and *Arabidopsis* (B). Expression of VIP2 was determined by semi-quantitative RT-PCR on the total RNA collected from the leaf samples of the independent transgenic lines of and to confirm the expression of the transgenes. The transgenic line NbVIP2-E7 (lanes 1-2) and NbVIP2-E5 (lanes 3, 4 and 5) showed higher transcript levels of VIP2 when compared to wild-type (WT) plants (panel A). The transgenic plant #1 (AtVIP2-E1) showed much higher expression of the AtVIP2 transcript when compared to the wild-type plants (panel B). Parallel reactions were performed using Nb ef1α a primers and At ef1α a as loading controls for wild-type and transgenic plants. The data presented here is the relative transcripts detected at 22 and 24 PCR cycles respectively. WT, Wild-type; NT, no template control; M, 1 Kb ladder.

Figure 19:
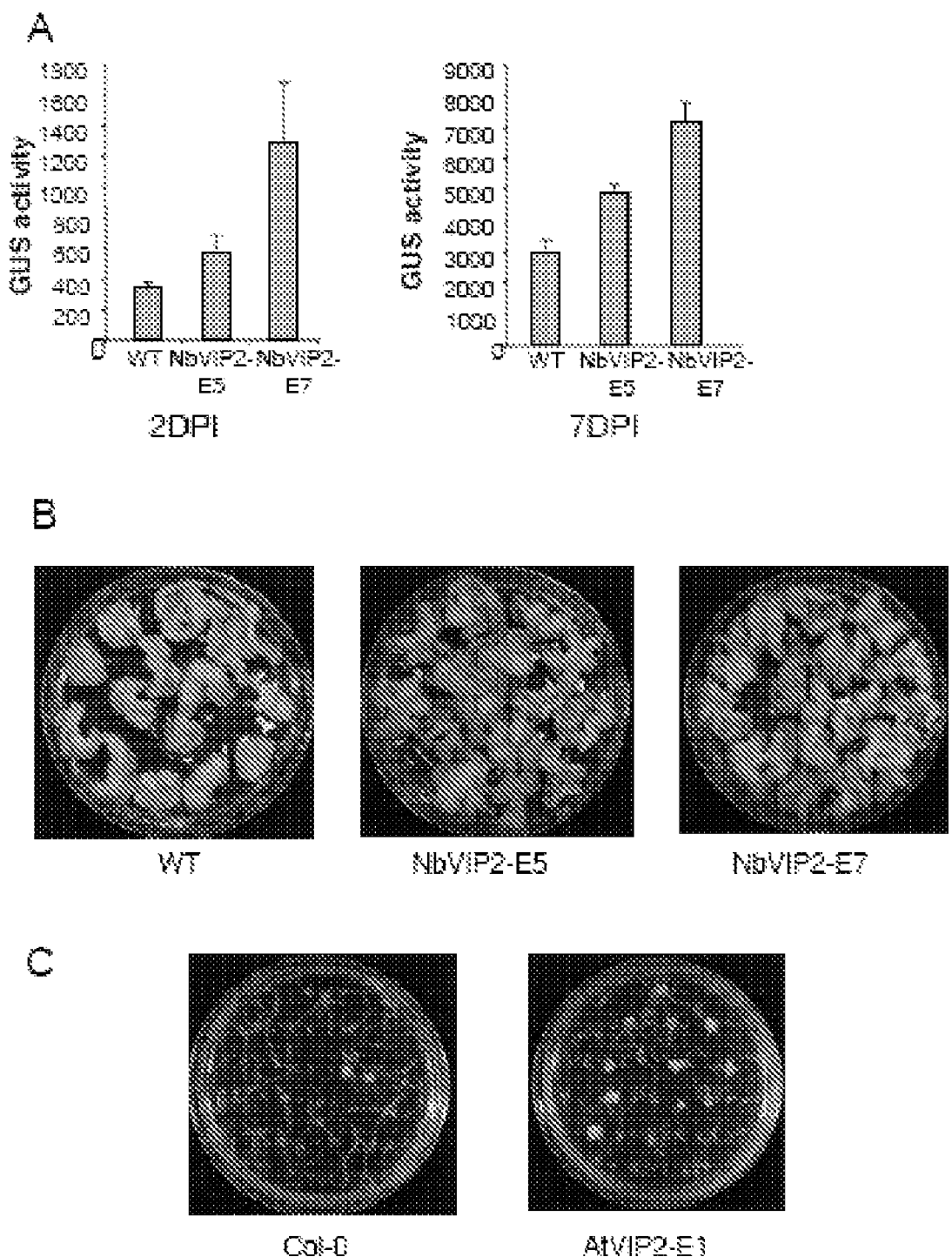

FIG. 19. Overexpression of VIP2 increases *Agrobacterium* infectivity in *N. benthamiana* and *Arabidopsis* transgenic plants. (A) Quantification of GUS activity using the transient transformation assay. Leaf disks of the transgenic lines NbVIP2-E5 and NbVIP2-E7 and wild-type (WT) *N.*

*benthamiana* plants were inoculated with non-tumorigenic strain *A. tumefaciens* GV2260 carrying pBISN1 (has uidA-intron gene within the T-DNA). The inoculated leaves were periodically collected and were used for measuring the fluorescence of 4-methylumbelliferone (4-MU). (B) Leaf disk tumorigenesis assay. Leaf disks of the NbVIP2 transgenic plants and wild-type (WT) plants were inoculated with tumorigenic strain *A. tumefaciens* A348 and incubated on hormone free MS medium. (C) Roots of wild-type Col-0 and the transgenic line AtVIP2-E1 were infected with a tumorigenic strain *A. tumefaciens* A208 (nopaline strain), and tumors incited on the roots were visualized. Photographs shown in B, and D were taken four weeks after *Agrobacterium* inoculation.

DESCRIPTION OF SEQUENCES

SEQ ID NO:1 Predicted peptide sequence of *Arabidopsis* VIP2 splice variant (GenBank AK117230).
SEQ ID NO:2 Predicted peptide sequence of *Arabidopsis* VIP2 splice variant (GenBank AF295433).
SEQ ID NO:3 Nucleotide sequence of *Arabidopsis* VIP2.
SEQ ID NO:4 *N. benthamiana* VIP2 polypeptide sequence (GenBank accession DQ000202).
SEQ ID NO:5 Tomato VIP2 polypeptide sequence (from GenBank accession BG130671).
SEQ ID NO:6 LeVIP2 forward primer.
SEQ ID NO:7 LeVIP2 reverse primer.
SEQ ID NO:8 attB1 primer.
SEQ ID NO:9 attB2 primer.
SEQ ID NO:10 TRV coat protein-specific forward primer.
SEQ ID NO:11 TRV coat protein-specific reverse primer.
SEQ ID NO:12 NbVIP2 forward primer.
SEQ ID NO:13 NbVIP2 reverse primer.
SEQ ID NO:14 NbEfF forward primer.
SEQ ID NO:15 NbEfR reverse primer.
SEQ ID NO:16 NbVIP2 qRT-PCR forward primer.
SEQ ID NO:17 NbVIP2 qRT-PCR reverse primer.
SEQ ID NO:18 GUS primer.
SEQ ID NO:19 GUS primer.
SEQ ID NO:20 Atu0792 primer.
SEQ ID NO:21 Atu0792 primer.
SEQ ID NO:22 qRT-PCR GUS-forward primer.
SEQ ID NO:23 qRT-PCR GUS-reverse primer.
SEQ ID NO:24 AtVIP2F primer.
SEQ ID NO:25 AtVIP2R primer.
SEQ ID NO:26 *N. benthamiana* VIP2 nucleotide sequence (from GenBank DQ000202).
SEQ ID NO:27 *Oyza sativa* NOT2 polypeptide sequence.
SEQ ID NO:28 *Arabidopsis* NOT2 polypeptide sequence.
SEQ ID NOs:29-46 Primers for use in Affymetrix expression studies.

DETAILED DESCRIPTION OF THE INVENTION

The invention provides methods and compositions for increasing *Agrobacterium*-mediated transformation efficiency by expressing a VIP2 or VIP2-like gene in a host cell. The plant VirE2-Interacting Protein 2 (VIP2) plays an important role in *Agrobacterium*-mediated cell transformation. The described methods and compositions are useful in enhancing *Agrobacterium*-mediated gene transfer to host cells, including plant cells.

In one aspect, the invention provides an expression cassette comprising a nucleotide sequence encoding VIP2 or VIP2-like polypeptide operably linked to a promoter which directs expression of the nucleotide sequence encoding VIP2 or VIP2-like polypeptide in the host cell. VIP2 and VIP2-like polypeptides (e.g. comprising a NOT domain) have been identified in plants, including from *Arabidopsis* (GenBank accession AK117230 (SEQ ID NO: 1); GenBank accession AF295433 (SEQ ID NO:2, encoded by SEQ ID NO:3); *Nicotiana benthamiana*, (GenBank accession DQ000202; SEQ ID NO:4), and tomato (*Lycopersicon esculentum*, GenBank accession BG130671; SEQ ID NO:5), among others. The expression cassette may be a plant expression cassette.

In another aspect the invention provides a method of increasing the efficiency of *Agrobacterium*-mediated gene transfer to a cell. The method comprises the steps of introducing into a host cell, a nucleotide sequence encoding a VIP2 polypeptide or a VIP2-like polypeptide, operably linked to a promoter which directs expression of the nucleotide sequence encoding VIP2 or VIP2-like polypeptide in the host cell. The host cell may include a plant, fungal, insect, or animal cell. In a particular embodiment the host cell is a plant cell.

In one embodiment of the invention, the plant cell may be a monocot plant cell, for instance a cell of a member of the Poaceae, including corn, wheat, rice, sorghum, sugar cane, rye, oat, barley, turfgrass, or millet, among others. In another embodiment, the plant cell may be a dicot plant cell, for instance a cell derived from a legume such as alfalfa, common bean, or soybean, or other dicot plant including cotton, tobacco, rapeseed, sunflower, sugar beet, among others.

In yet another aspect of the invention, another method for increasing the efficiency of *Agrobacterium*-mediated gene transfer is provided. The method comprises the steps of: (a) introducing into a host cell, a nucleotide sequence encoding VIP2 or VIP2-like polypeptide operably linked to a promoter which directs expression of the nucleotide sequence encoding VIP2 or VIP2-like polypeptide in the host cell, and (b) transforming the host cell with an *Agrobacterium* transformation vector. The host cell may be transformed with the *Agrobacterium* transformation vector simultaneously with the VIP2 gene or following transformation of the host cell with a VIP2 or VIP2-like coding sequence. The *Agrobacterium* transformation vector may comprise one or more T-DNA sequences adjacent to one or more border sequences. In another embodiment, a (trans)gene of interest is positioned within a T-DNA region, adjacent to or flanked by one or more border sequences for transfer into the host cell. Thus, transfer of the gene of interest may be facilitated due to the host cell expressing a VIP2 or VIP2-like coding sequence.

I. Plant Expression Constructs and Nucleic Acids

In one aspect of the invention, a plant transformation vector comprising a nucleic acid encoding a VIP2 or VIP2-like polypeptide is provided. An exemplary construct may comprise a promoter functional in a plant operably linked to a nucleic acid sequence encoding a VIP2 polypeptide. Examples of regulatory sequences which may be used to drive expression of a VIP2 or VIP2-like genes in host cells include the CaMV 35S promoter, nopaline synthase promoter, or TRV promoter in plant cells. The promoter may be a constitutive promoter or an inducible promoter.

In one embodiment of the invention, a polypeptide is therefore provided that comprises an enzyme coding sequence or the polypeptide encoded thereby set forth in the Sequence Listing, as well as polypeptides and fragments thereof, particularly those polypeptides which exhibit enzyme activity have at least 85%, more preferably at least 90% identity, and most preferably at least 95% identity to a polypeptide sequence selected from the group of sequences set forth in the Sequence Listing. "Identity," as is well understood in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences. Methods to determine "identity" are designed to give the largest match between the sequences tested. Moreover, methods to determine identity are codified in publicly available programs. "Identity" can be readily calculated by known methods including, but not limited to, those described in Computational Molecular Biology (1988); Biocomputing: Informatics and Genome Projects (1993); Computer Analysis of Sequence Data (1994); Sequence Analysis in Molecular Biology (1987); Sequence Analysis Primer (1991); and Carillo and Lipman (1988). Computer programs can be used to determine "identity" between two sequences these programs include but are not limited to, GCG (Devereux et al., 1984); suite of five BLAST programs, three designed for nucleotide sequences queries (BLASTN, BLASTX, and TBLASTX) and two designed for protein sequence queries (BLASTP and TBLASTN) (Coulson, 1994; Birren et al., 1997). The BLAST X program is publicly available from NCBI and other sources (Karlin and Altschul, 1990, 1993; Altschul et al., 1990). The well known Smith Waterman algorithm can also be used to determine identity (Smith and Waterman, 1981).

Parameters for polypeptide sequence comparison include the following: Algorithm: Needleman and Wunsch, (1970); Comparison matrix: BLOSSUM62 from Hentikoff and Hentikoff (1992); Gap Penalty: 12; and Gap Length Penalty: 4. A program which can be used with these parameters is publicly available as the "gap" program from Genetics Computer Group, Madison Wis. The above parameters along with no penalty for end gap may serve as default parameters for peptide comparisons.

Parameters for polynucleotide sequence comparison include the following: Algorithm: Needleman and Wunsch (1970); Comparison matrix: matches=+10; mismatches=0; Gap Penalty: 50; and Gap Length Penalty: 3. A program which can be used with these parameters is publicly available as the "gap" program from Genetics Computer Group, Madison Wis. The above parameters may serve as the default parameters for nucleic acid comparisons.

The invention therefore provides nucleic acids encoding polypeptide described herein. The nucleic acid may be defined as comprising nucleic acids encoding, in frame, the polypeptide. Those of skill in the art will understand in view of the disclosure that such nucleic acids may be provided as an expression construct by linking appropriate regulatory elements to the nucleic acid corresponding to a host cell in which heterologous expression is desired. For plant expression, a plant promoter may be operably linked to the nucleic acid. In addition, other elements such as enhancers, terminators and transit peptides may be used. Endogenous or heterologous elements may be used. For example, MtIOMT could be placed at the N-terminus of the encoded polypeptide in order to utilize a native endoplasmic reticulum localization peptide.

The construction of vectors which may be employed in conjunction with plant transformation techniques using these or other sequences according to the invention will be known to those of skill of the art in light of the present disclosure (see, for example, Sambrook et al., 1989; Gelvin et al., 1990). The techniques of the current invention are thus not limited to any particular nucleic acid sequences.

One important use of the sequences provided by the invention will be in the alteration of plant phenotypes by genetic transformation with coding sequences that alter plant secondary metabolite biosynthesis as described herein. The coding sequences may be provided with other sequences such as regulatory elements or other coding sequences. Where a selectable or screenable marker is used, one may employ the separate coding regions on either the same or different DNA segments for transformation. In the latter case, the different vectors are delivered concurrently to recipient cells to maximize co-transformation.

Vectors used for plant transformation may include, for example, plasmids, cosmids, YACs (yeast artificial chromosomes), BACs (bacterial artificial chromosomes) or any other suitable cloning system, as well as fragments of DNA therefrom. Thus when the term "vector" or "expression vector" is used, all of the foregoing types of vectors, as well as nucleic acid sequences isolated therefrom, are included. It is contemplated that utilization of cloning systems with large insert capacities will allow introduction of large DNA sequences comprising more than one selected gene. In accordance with the invention, this could be used to introduce genes corresponding to an entire biosynthetic pathway into a plant. Introduction of such sequences may be facilitated by use of bacterial or yeast artificial chromosomes (BACs or YACs, respectively), or even plant artificial chromosomes. For example, the use of BACs for *Agrobacterium*-mediated transformation was disclosed by Hamilton et al. (1996).

Particularly useful for transformation are expression cassettes which have been isolated from such vectors. DNA segments used for transforming plant cells will, of course, generally comprise coding sequence which one desires to introduce into and have expressed in the host cells. These DNA segments can further include structures such as promoters, enhancers, polylinkers, or even regulatory genes as desired. The DNA segment or gene chosen for cellular introduction will often encode a protein which will be expressed in the resultant recombinant cells resulting in a screenable or selectable trait and/or which will impart an improved phenotype to the resulting transgenic plant. Preferred components that may be included with plant transformation vectors are as follows.

A. Regulatory Elements

Exemplary promoters for expression of a nucleic acid sequence in plants include the CaMV 35S promoter (Odell et al., 1985), CaMV 19S (Lawton et al., 1987), nos (Ebert et al., 1987), Adh (Walker et al., 1987), sucrose synthase (Yang and Russell, 1990), a-tubulin, actin (Wang et al., 1992), cab (Sullivan et al., 1989), PEPCase (Hudspeth and Grula, 1989) or R gene complex associated promoters (Chandler et al., 1989). Tissue specific promoters such as root cell promoters (Conkling et al., 1990) and tissue specific enhancers (Fromm et al., 1986) are also contemplated to be useful, as are inducible promoters such as ABA- and turgor-inducible promoters. In one embodiment of the invention, the native promoter of a isoflavone biosynthesis sequence is used. In another embodiment, a heterologous sequence is used.

The DNA sequence between the transcription initiation site and the start of the coding sequence, i.e., the untranslated leader sequence, can also influence gene expression. One may thus wish to employ a particular leader sequence with a transformation construct of the invention. Preferred leader sequences are contemplated to include those which comprise sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants will typically be preferred.

It is envisioned that nucleic acids encoding a polypeptide as provided herein may be introduced under the control of novel promoters or enhancers, etc., or homologous or tissue specific promoters or control elements. Vectors for use in tissue-specific targeting of genes in transgenic plants will typically include tissue-specific promoters and may also include other tissue-specific control elements such as enhancer sequences. Promoters which direct specific or enhanced expression in certain plant tissues will be known to those of skill in the art in light of the present disclosure. These include, for example, the rbcS promoter, specific for green tissue; the ocs, nos and mas promoters which have higher activity in roots or wounded leaf tissue.

B. Terminators

Transformation constructs prepared in accordance with the invention will typically include a 3' end DNA sequence that acts as a signal to terminate transcription and allow for the poly-adenylation of the mRNA produced by coding sequences operably linked to a promoter. Alternatively, a heterologous 3' end may enhance the expression of coding sequences. Examples of terminators that are deemed to be useful in this context include those from the nopaline synthase gene of *Agrobacterium tumefaciens* (nos 3' end) (Bevan et al., 1983), the terminator for the T7 transcript from the octopine synthase gene of *Agrobacterium tumefaciens*, and the 3' end of the protease inhibitor I or II genes from potato or tomato. Regulatory elements such as an Adh intron (Callis et al., 1987), sucrose synthase intron (Vasil et al., 1989) or TMV omega element (Gallie et al., 1989), may further be included where desired.

C. Transit or Signal Peptides

Sequences that are joined to the coding sequence of an expressed gene, which are removed post-translationally from the initial translation product and which facilitate the transport of the protein into or through intracellular or extracellular membranes, are termed transit (usually into vacuoles, vesicles, plastids and other intracellular organelles) and signal sequences (usually to the endoplasmic reticulum, golgi apparatus and outside of the cellular membrane). By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed.

D. Marker Genes

By employing a selectable or screenable marker protein, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker proteins are known to the art and can be employed in the practice of the invention.

Included within the terms selectable or screenable markers also are genes which encode a "secretable marker" whose secretion can be detected as a means of identifying or selecting for transformed cells. Examples include markers which are secretable antigens that can be identified by antibody interaction, or even secretable enzymes which can be detected by their catalytic activity.

Many selectable marker coding regions are known and could be used with the present invention including, but not limited to, neo (Potrykus et al., 1985), which provides kanamycin resistance and can be selected for using kanamycin, G418, paromomycin, etc.; bar, which confers bialaphos or phosphinothricin resistance; a mutant EPSP synthase protein (Hinchee et al., 1988) conferring glyphosate resistance; a nitrilase such as bxn from *Klebsiella ozaenae* which confers resistance to bromoxynil (Stalker et al., 1988); a mutant acetolactate synthase (ALS) which confers resistance to imidazolinone, sulfonylurea or other ALS inhibiting chemicals (European Patent Application 154,204, 1985); a methotrexate resistant DHFR (Thillet et al., 1988), a dalapon dehalogenase that confers resistance to the herbicide dalapon; or a mutated anthranilate synthase that confers resistance to 5-methyl tryptophan.

Screenable markers that may be employed include a β-glucuronidase (GUS) or uidA gene which encodes an enzyme for which various chromogenic substrates are known; an R-locus gene, which encodes a product that regulates the production of anthocyanin pigments (red color) in plant tissues (Dellaporta et al., 1988); a β-lactamase gene (Sutcliffe, 1978), which encodes an enzyme for which various chromogenic substrates are known (e.g., PADAC, a chromogenic cephalosporin); a xylE gene (Zukowsky et al., 1983) which encodes a catechol dioxygenase that can convert chromogenic catechols; an α-amylase gene (Ikuta et al., 1990); a tyrosinase gene (Katz et al., 1983) which encodes an enzyme capable of oxidizing tyrosine to DOPA and dopaquinone which in turn condenses to form the easily-detectable compound melanin; a β-galactosidase gene, which encodes an enzyme for which there are chromogenic substrates; a luciferase (lux) gene (Ow et al., 1986), which allows for bioluminescence detection; or a gene encoding for green fluorescent protein (Sheen et al., 1995; Haseloff et al., 1997; Reichel et al., 1996; Tian et al., 1997; WO 97/41228).

II. Methods for Genetic Transformation

Suitable methods for transformation of plant or other cells for use with the current invention are believed to include virtually any method by which DNA can be introduced into a cell, such as by direct delivery of DNA such as by PEG-mediated transformation of protoplasts (Omirulleh et al., 1993), by desiccation/inhibition-mediated DNA uptake (Potrykus et al., 1985), by electroporation (U.S. Pat. No. 5,384,253, specifically incorporated herein by reference in its entirety), by agitation with silicon carbide fibers (Kaeppler et al., 1990; U.S. Pat. No. 5,302,523, specifically incorporated herein by reference in its entirety; and U.S. Pat. No. 5,464,765, specifically incorporated herein by reference in its entirety), by Agrobacterium-mediated transformation (U.S. Pat. Nos. 5,591,616 and 5,563,055; both specifically incorporated herein by reference) and by acceleration of DNA coated particles (U.S. Pat. Nos. 5,550,318; 5,538,877; and 5,538,880; each specifically incorporated herein by reference in its entirety), etc. Through the application of techniques such as these, the cells of virtually any plant species may be stably transformed, and these cells developed into transgenic plants.

A. Agrobacterium-mediated Transformation

Agrobacterium-mediated transfer is a widely applicable system for introducing genes into plant cells because the DNA can be introduced into whole plant tissues, thereby bypassing the need for regeneration of an intact plant from a protoplast. The use of Agrobacterium-mediated plant integrating vectors to introduce DNA into plant cells is well known in the art. See, for example, the methods described by Fraley et al., (1985), Rogers et al., (1987) and U.S. Pat. No. 5,563,055, specifically incorporated herein by reference in its entirety.

Agrobacterium-mediated transformation is most efficient in dicotyledonous plants and is the preferable method for transformation of dicots, including Arabidopsis, tobacco, tomato, alfalfa and potato. Indeed, while Agrobacterium-mediated transformation has been routinely used with dicotyledonous plants for a number of years, it has only recently become applicable to monocotyledonous plants. Advances in Agrobacterium-mediated transformation techniques have now made the technique applicable to nearly all monocotyledonous plants. For example, Agrobacterium-mediated transformation techniques have now been applied to rice (Hiei et al., 1997; U.S. Pat. No. 5,591,616, specifically incorporated herein by reference in its entirety), wheat (McCormac et al., 1998), barley (Tingay et al., 1997; McCormac et al., 1998) and maize (Ishida et al., 1996).

Modern Agrobacterium transformation vectors are capable of replication in E. coli as well as Agrobacterium, allowing for convenient manipulations as described (Klee et al., 1985). Moreover, recent technological advances in vectors for Agrobacterium-mediated gene transfer have improved the arrangement of genes and restriction sites in the vectors to facilitate the construction of vectors capable of expressing various polypeptide coding genes. The vectors described (Rogers et al., 1987) have convenient multi-linker regions flanked by a promoter and a polyadenylation site for direct expression of inserted polypeptide coding genes and are suitable for present purposes. In addition, Agrobacterium containing both armed and disarmed Ti genes can be used for the transformations. In those plant strains where Agrobacterium-mediated transformation is efficient, it is the method of choice because of the facile and defined nature of the gene transfer.

B. Electroporation

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plants (Bates, 1994; Lazzeri, 1995). For example, the generation of transgenic soybean plants by electroporation of cotyledon-derived protoplasts is described by Dhir and Widholm in Intl. Patent Appl. Publ. No. WO 9217598 (specifically incorporated herein by reference). Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

C. Microprojectile Bombardment

Another method for delivering transforming DNA segments to plant cells in accordance with the invention is microprojectile bombardment (U.S. Pat. Nos. 5,550,318; 5,538,880; 5,610,042; and PCT Application WO 94/09699; each of which is specifically incorporated herein by reference in its entirety). In this method, particles may be coated with nucleic acids and delivered into cells by a propelling force. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. Hence, it is proposed that DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a filter surface covered with monocot plant cells cultured in suspension. The screen disperses the particles so that they are not delivered to the recipient cells in large aggregates. Microprojectile bombardment techniques are widely applicable, and may be used to transform virtually any plant species. Examples of species for which have been transformed by microprojectile bombardment include monocot species such as maize (PCT Application WO 95/06128), barley (Ritala et al., 1994; Hensgens et al., 1993), wheat (U.S. Pat. No. 5,563,055, specifically incorporated herein by reference in its entirety), rice (Hensgens et al., 1993), oat (Torbet et al., 1995; Torbet et al., 1998), rye (Hensgens et al., 1993), sugarcane (Bower et al., 1992), and sorghum (Casa et al., 1993; Hagio et al., 1991); as well as a number of dicots including tobacco (Tomes et al., 1990; Buising and Benbow, 1994), soybean (U.S. Pat. No. 5,322,783, specifically incorporated herein by reference in its entirety), sunflower (Knittel et al. 1994), peanut (Singsit et al., 1997), cotton (McCabe and Martinell, 1993), tomato (VanEck et al. 1995), and legumes in general (U.S. Pat. No. 5,563,055, specifically incorporated herein by reference in its entirety).

D. Other Transformation Methods

Transformation of protoplasts can be achieved using methods based on calcium phosphate precipitation, polyethylene glycol treatment, electroporation, and combinations of these treatments (see, e.g., Potrykus et al., 1985; Lorz et al., 1985; Omirulleh et al., 1993; Fromm et al., 1986; Uchimiya et al., 1986; Callis et al., 1987; Marcotte et al., 1988).

Application of these systems to different plant strains depends upon the ability to regenerate that particular plant strain from protoplasts. Illustrative methods for the regeneration of cereals from protoplasts have been described (Toriyama et al., 1986; Yamada et al., 1986; Abdullah et al., 1986; Omirulleh et al., 1993 and U.S. Pat. No. 5,508,184; each specifically incorporated herein by reference in its entirety). Examples of the use of direct uptake transformation of cereal protoplasts include transformation of rice (Ghosh-Biswas et al., 1994), sorghum (Battraw and Hall, 1991), barley (Lazerri, 1995), oat (Zheng and Edwards, 1990) and maize (Omirulleh et al., 1993).

To transform plant lines that cannot be successfully regenerated from protoplasts, other ways to introduce DNA into intact cells or tissues can be utilized. For example, regeneration of cereals from immature embryos or explants can be effected as described (Vasil, 1989). Also, silicon carbide fiber-mediated transformation may be used with or without protoplasting (Kaeppler, 1990; Kaeppler et al., 1992; U.S. Pat. No. 5,563,055, specifically incorporated herein by reference in its entirety). Transformation with this technique is accomplished by agitating silicon carbide fibers together with cells in a DNA solution. DNA passively enters as the cells are punctured. This technique has been used successfully with, for example, the monocot cereals maize (PCT Application WO 95/06128, specifically incorporated herein by reference in its entirety (Thompson, 1995), and rice (Nagatani, 1997).

E. Tissue Cultures

Tissue cultures may be used in certain transformation techniques for the preparation of cells for transformation and for the regeneration of plants therefrom. Maintenance of tissue cultures requires use of media and controlled environments. "Media" refers to the numerous nutrient mixtures that are used to grow cells in vitro, that is, outside of the intact living organism. The medium usually is a suspension of various categories of ingredients (salts, amino acids, growth regulators, sugars, buffers) that are required for growth of most cell types. However, each specific cell type requires a specific range of ingredient proportions for growth, and an even more specific range of formulas for optimum growth. Rate of cell growth also will vary among cultures initiated with the array of media that permit growth of that cell type.

Nutrient media is prepared as a liquid, but this may be solidified by adding the liquid to materials capable of providing a solid support. Agar is most commonly used for this purpose. Bactoagar (e.g. Difco Laboratories, Detroit, Mich.), Hazelton agar, Gelrite, and Gelgro are specific types of solid support that are suitable for growth of plant cells in tissue culture.

Some cell types will grow and divide either in liquid suspension or on solid media. As disclosed herein, plant cells will grow in suspension or on solid medium, but regeneration of plants from suspension cultures typically requires transfer from liquid to solid media at some point in development. The type and extent of differentiation of cells in culture will be affected not only by the type of media used and by the environment, for example, pH, but also by whether media is solid or liquid.

Tissue that can be grown in a culture includes meristem cells, Type I, Type II, and Type III callus, immature embryos and gametic cells such as microspores, pollen, sperm and egg cells. Type I, Type II, and Type III callus may be initiated from tissue sources including, but not limited to, immature embryos, seedling apical meristems, root, leaf, microspores and the like. Those cells which are capable of proliferating as callus also are recipient cells for genetic transformation.

Somatic cells are of various types. Embryogenic cells are one example of somatic cells which may be induced to regenerate a plant through embryo formation. Non-embryogenic cells are those which typically will not respond in such a fashion. Certain techniques may be used that enrich recipient cells within a cell population. For example, Type II callus development, followed by manual selection and culture of friable, embryogenic tissue, generally results in an enrichment of cells. Manual selection techniques which can be employed to select target cells may include, e.g., assessing cell morphology and differentiation, or may use various physical or biological means. Cryopreservation also is a possible method of selecting for recipient cells.

Manual selection of recipient cells, e.g., by selecting embryogenic cells from the surface of a Type II callus, is one means that may be used in an attempt to enrich for particular cells prior to culturing (whether cultured on solid media or in suspension).

Where employed, cultured cells may be grown either on solid supports or in the form of liquid suspensions. In either instance, nutrients may be provided to the cells in the form of media, and environmental conditions controlled. There are many types of tissue culture media comprised of various amino acids, salts, sugars, growth regulators and vitamins. Most of the media employed in the practice of the invention will have some similar components, but may differ in the composition and proportions of their ingredients depending on the particular application envisioned. For example, various cell types usually grow in more than one type of media, but will exhibit different growth rates and different morphologies, depending on the growth media. In some media, cells survive but do not divide. Various types of media suitable for culture of plant cells previously have been described. Examples of these media include, but are not limited to, the N6 medium described by Chu et al. (1975) and MS media (Murashige and Skoog, 1962).

III. Production and Characterization of Stably Transformed Plants

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait.

A. Selection

It is believed that DNA is introduced into only a small percentage of target cells in any one study. In order to provide an efficient system for identification of those cells receiving DNA and integrating it into their genomes one may employ a means for selecting those cells that are stably transformed. One exemplary embodiment of such a method is to introduce into the host cell, a marker gene which confers resistance to some normally inhibitory agent, such as an antibiotic or herbicide. Examples of antibiotics which may be used include the aminoglycoside antibiotics neomycin, kanamycin and paromomycin, or the antibiotic hygromycin. Resistance to the aminoglycoside antibiotics is conferred by aminoglycoside phosphotransferase enzymes such as neomycin phosphotransferase II (NPT II) or NPT I, whereas resistance to hygromycin is conferred by hygromycin phosphotransferase.

Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA.

One herbicide which constitutes a desirable selection agent is the broad spectrum herbicide bialaphos. Bialaphos is a tripeptide antibiotic produced by *Streptomyces hygroscopicus* and is composed of phosphinothricin (PPT), an analogue of L-glutamic acid, and two L-alanine residues. Upon removal of the L-alanine residues by intracellular peptidases, the PPT is released and is a potent inhibitor of glutamine synthetase (GS), a pivotal enzyme involved in ammonia assimilation and nitrogen metabolism (Ogawa et al., 1973). Synthetic PPT, the active ingredient in the herbicide Liberty™ also is effective as a selection agent. Inhibition of GS in plants by PPT causes the rapid accumulation of ammonia and death of the plant cells.

The organism producing bialaphos and other species of the genus *Streptomyces* also synthesizes an enzyme phosphinothricin acetyl transferase (PAT) which is encoded by the bar gene in *Streptomyces hygroscopicus* and the pat gene in *Streptomyces viridochromogenes*. The use of the herbicide resistance gene encoding phosphinothricin acetyl transferase (PAT) is referred to in DE 3642 829 A, wherein the gene is isolated from *Streptomyces viridochromogenes*.

Another example of a herbicide which is useful for selection of transformed cell lines in the practice of the invention is the broad spectrum herbicide glyphosate. Glyphosate inhibits the action of the enzyme EPSPS which is active in the aromatic amino acid biosynthetic pathway. Inhibition of this enzyme leads to starvation for the amino acids phenylalanine, tyrosine, and tryptophan and secondary metabolites derived thereof. U.S. Pat. No. 4,535,060 describes the isolation of EPSPS mutations which confer glyphosate resistance on polypeptides encoded by the *Salmonella typhimurium* gene for EPSPS, aroA. The EPSPS gene was cloned from *Zea mays* and mutations similar to those found in a glyphosate resistant aroA gene were introduced in vitro. Mutant genes encoding glyphosate resistant EPSPS enzymes are described in, for example, International Patent WO 97/4103. The best characterized mutant EPSPS gene conferring glyphosate resistance comprises amino acid changes at residues 102 and 106, although it is anticipated that other mutations will also be useful (PCT/WO97/4103).

To use a bar-bialaphos or the EPSPS-glyphosate selective system, for example, transformed tissue can be cultured for 0-28 days on nonselective medium and subsequently transferred to medium containing from 1-3 mg/l bialaphos or 1-3 mM glyphosate as appropriate. While ranges of 1-3 mg/l bialaphos or 1-3 mM glyphosate may be preferred, it is proposed that ranges of 0.1-50 mg/l bialaphos or 0.1-50 mM glyphosate will find utility.

B. Regeneration and Seed Production

Cells that survive the exposure to the selective agent, or cells that have been scored positive in a screening assay, may be cultured in media that supports regeneration of plants. In an exemplary embodiment, MS and N6 media may be modified by including further substances such as growth regulators. One such growth regulator is dicamba or 2,4-D. However, other growth regulators may be employed, including NAA, NAA+2,4-D or picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, at least 2 wk, then transferred to media conducive to maturation of embryoids. Cultures are transferred every 2 wk on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soilless plant growth mix, and hardened, e.g., in an environmentally controlled chamber, for example, at about 85% relative humidity, 600 ppm $CO_2$, and 25-250 microeinsteins $m^{-2}$ $s^{-1}$ of light. Plants may be matured in a growth chamber or greenhouse. Plants can be regenerated from about 6 wk to 10 months after a transformant is identified, depending on the initial tissue. During regeneration, cells are grown on solid media in tissue culture vessels. Illustrative embodiments of such vessels are petri dishes and Plant Cons. Regenerating plants can be grown at about 19 to 28° C. After the regenerating plants have reached the stage of shoot and root development, they may be transferred to a greenhouse for further growth and testing.

Seeds on transformed plants may occasionally require embryo rescue due to cessation of seed development and premature senescence of plants. To rescue developing embryos, they are excised from surface-disinfected seeds 10-20 days post-pollination and cultured. An embodiment of media used for culture at this stage comprises MS salts, 2% sucrose, and 5.5 µl agarose. In embryo rescue, large embryos (defined as greater than 3 mm in length) are germinated directly on an appropriate media. Embryos smaller than that may be cultured for 1 wk on media containing the above ingredients along with $10^{-5}M$ abscisic acid and then transferred to growth regulator-free medium for germination.

C. Characterization

To confirm the presence of the exogenous DNA or "transgene(s)" in the regenerating plants, a variety of assays may be performed. Such assays include, for example, "molecular biological" assays, such as Southern and Northern blotting and PCR™; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

D. DNA Integration, RNA Expression and Inheritance

Genomic DNA may be isolated from cell lines or any plant parts to determine the presence of the exogenous gene through the use of techniques well known to those skilled in the art. Note, that intact sequences will not always be present, presumably due to rearrangement or deletion of sequences in the cell. The presence of DNA elements introduced through the methods of this invention may be determined, for example, by polymerase chain reaction (PCR™). Using this technique, discrete fragments of DNA are amplified and detected by gel electrophoresis. This type of analysis permits one to determine whether a gene is present in a stable transformant, but does not prove integration of the introduced gene into the host cell genome. It is typically the case, however, that DNA has been integrated into the genome of all transformants that demonstrate the presence of the gene through PCR™ analysis. In addition, it is not typically possible using PCR™ techniques to determine whether transformants have exogenous genes introduced into different sites in the genome, i.e., whether transformants are of independent origin. It is contemplated that using PCR™ techniques it would be possible to clone fragments of the host genomic DNA adjacent to an introduced gene.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced genes in high molecular weight DNA, i.e., confirm that the introduced gene has been integrated into the host cell genome. The technique of Southern hybridization provides information that is obtained using PCR™, e.g., the presence of a gene, but also demonstrates integration into the genome and characterizes each individual transformant.

It is contemplated that using the techniques of dot or slot blot hybridization which are modifications of Southern hybridization techniques one could obtain the same information that is derived from PCR™, e.g., the presence of a gene.

Both PCR™ and Southern hybridization techniques can be used to demonstrate transmission of a transgene to progeny. In most instances the characteristic Southern hybridization pattern for a given transformant will segregate in progeny as one or more Mendelian genes (Spencer et al., 1992) indicating stable inheritance of the transgene.

Whereas DNA analysis techniques may be conducted using DNA isolated from any part of a plant, RNA will only be expressed in particular cells or tissue types and hence it will be necessary to prepare RNA for analysis from these tissues. PCR™ techniques also may be used for detection and quantitation of RNA produced from introduced genes. In this application of PCR™ it is first necessary to reverse transcribe RNA into DNA, using enzymes such as reverse transcriptase, and then through the use of conventional PCR™ techniques amplify the DNA. In most instances PCR™ techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species also can be determined using dot or slot blot Northern hybridizations. These techniques are modifications of Northern blotting and will only demonstrate the presence or absence of an RNA species.

E. Gene Expression

While Southern blotting and PCR™ may be used to detect the gene(s) in question, they do not provide information as to whether the corresponding protein is being expressed. Expression may be evaluated by specifically identifying the protein products of the introduced genes or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of genes encoding enzymes or storage proteins which change amino acid composition and may be detected by amino acid analysis, or by enzymes which change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays.

IV. Breeding Plants of the Invention

In addition to direct transformation of a particular plant genotype with a construct prepared according to the current invention, transgenic plants may be made by crossing a plant having a selected DNA of the invention to a second plant lacking the construct. For example, a selected polypeptide coding sequence can be introduced into a particular plant variety by crossing, without the need for ever directly transforming a plant of that given variety. Therefore, the current invention not only encompasses a plant directly transformed or regenerated from cells which have been transformed in accordance with the current invention, but also the progeny of such plants. As used herein the term "progeny" denotes the offspring of any generation of a parent plant prepared in accordance with the instant invention, wherein the progeny comprises a selected DNA construct prepared in accordance with the invention. "Crossing" a plant to provide a plant line having one or more added transgenes relative to a starting plant line, as disclosed herein, is defined as the techniques that result in a transgene of the invention being introduced into a plant line by crossing a starting line with a donor plant line that comprises a transgene of the invention. To achieve this one could, for example, perform the following steps:

(a) plant seeds of the first (starting line) and second (donor plant line that comprises a transgene of the invention) parent plants;

(b) grow the seeds of the first and second parent plants into plants that bear flowers;

(c) pollinate a flower from the first parent plant with pollen from the second parent plant; and (d) harvest seeds produced on the parent plant bearing the fertilized flower.

Backcrossing is herein defined as the process including the steps of:

(a) crossing a plant of a first genotype containing a desired gene, DNA sequence or element to a plant of a second genotype lacking the desired gene, DNA sequence or element;

(b) selecting one or more progeny plant containing the desired gene, DNA sequence or element;

(c) crossing the progeny plant to a plant of the second genotype; and (d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

VI. Definitions

*Agrobacterium*-mediated transformation: Methods of *Agrobacterium*-mediated plant cell transformation include the use of bacterial strain(s) classified among the Rhizobiaceae, including *Agrobacterium* sp., *Rhizobium* sp., *Sinorhizobium* sp., among others. *Agrobacterium* may also mediate transformation of other eukaryotic cells, including fungal and insect cells.

Expression: The combination of intracellular processes, including transcription and translation undergone by a coding DNA molecule such as a structural gene to produce a polypeptide.

Genetic Transformation: A process of introducing a DNA sequence or construct (e.g., a vector or expression cassette) into a cell or protoplast in which that exogenous DNA is incorporated into a chromosome or is capable of autonomous replication.

Heterologous: A sequence which is not normally present in a given host genome in the genetic context in which the sequence is currently found In this respect, the sequence may be native to the host genome, but be rearranged with respect to other genetic sequences within the host sequence. For example, a regulatory sequence may be heterologous in that it is linked to a different coding sequence relative to the native regulatory sequence.

Obtaining: When used in conjunction with a transgenic plant cell or transgenic plant, obtaining means either transforming a non-transgenic plant cell or plant to create the transgenic plant cell or plant, or planting transgenic plant seed to produce the transgenic plant cell or plant. Such a transgenic plant seed may be from an Ro transgenic plant or may be from a progeny of any generation thereof that inherits a given transgenic sequence from a starting transgenic parent plant.

Promoter: A recognition site on a DNA sequence or group of DNA sequences that provides an expression control element for a structural gene and to which RNA polymerase specifically binds and initiates RNA synthesis (transcription) of that gene.

$R_0$ transgenic plant: A plant that has been genetically transformed or has been regenerated from a plant cell or cells that have been genetically transformed.

Regeneration: The process of growing a plant from a plant cell (e.g., plant protoplast, callus or explant).

Selected DNA: A DNA segment which one desires to introduce or has introduced into a plant genome by genetic transformation.

Transformation construct: A chimeric DNA molecule which is designed for introduction into a host genome by genetic transformation. Preferred transformation constructs will comprise all of the genetic elements necessary to direct the expression of one or more exogenous genes. In particular embodiments of the instant invention, it may be desirable to introduce a transformation construct into a host cell in the form of an expression cassette.

Transformed cell: A cell the DNA complement of which has been altered by the introduction of an exogenous DNA molecule into that cell.

Transgene: A segment of DNA which has been incorporated into a host genome or is capable of autonomous replication in a host cell and is capable of causing the expression of one or more coding sequences. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the DNA segment.

Transgenic plant: A plant or progeny plant of any subsequent generation derived therefrom, wherein the DNA of the plant or progeny thereof contains an introduced exogenous DNA segment not naturally present in a non-transgenic plant of the same strain. The transgenic plant may additionally contain sequences which are native to the plant being transformed, but wherein the "exogenous" gene has been altered in order to alter the level or pattern of expression of the gene, for example, by use of one or more heterologous regulatory or other elements.

Vector: A DNA molecule designed for transformation into a host cell. Some vectors may be capable of replication in a host cell. A plasmid is an exemplary vector, as are expression cassettes isolated therefrom.

VIP2-like polypeptide: A polypeptide comprising a primary sequence with at least 60%, 70%, 80%, 85%, 90% or at least 95% sequence similarity to a known VIP2 polypeptide, which possesses VIP2 activity.

VI. EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Materials and Methods

A. Yeast Two-hybrid Assay.

Yeast two-hybrid assays were carried out as previously described ((Lin et al., 2002). In particular, *Saccharomyces cerevisiae* strain L40 {MATa his3Δ200 trp1-901 leu2-3,112 ade2 lys2-801am URA3::(lexAop)$_8$-lacZ LYS2::(lexAop)$_4$-HIS3} (Hollenberg et al., 1995) was grown in yeast extract/peptone/dextrose (YPD) or the appropriate selective minimal medium using standard conditions (Kaiser et al., 1994). Plasmids were introduced into yeast cells using a standard lithium acetate protocol (Kaiser et al., 1994). *Arabidopsis thaliana*

(ecotype Colombia) cDNA library in pGAD424 (LEU3+, Clontech, Mountain View, Calif., USA) (Ballas and Citovsky, 1997) was screened with pBTM116-VirE2 (Tzfira et al., 2001) as bait as described (Hollenberg et al., 1995; Ballas and Citovsky, 1997; Tzfira et al., 2001) and positive clones were selected on a histidine-deficient selective medium and confirmed by the β-galactosidase assay as described (Durfee et al., 1993). False-positives were eliminated using human lamin C and topoisomerase I, known to function as non-specific activators in the two-hybrid system (Hollenberg et al., 1995; Bartel et al., 1993), as baits. The NbVIP2 gene was cloned into pGAD424 as a Pst1 fragment and screened with pBTM116-VirE2 as bait for characterizing its interaction with VirE2.

B. VIGS and in Planta Tumor Assay.

Plant material, bacterial culture conditions, cloning of the NbVIP2 gene into the TRV-VIGS vector and sequence conformation and protocols for VIGS were performed as follows. *Nicotiana benthamiana* seeds were germinated in flats with a soil-less potting mixture, BM7 (Berger Co., Quebec, Canada) and the germinated seedlings were propagated as detailed in (Ryu et al., 2004). One to three week-old plants were used for silencing experiments. All *Agrobacterium* strains were cultured in Luria-Bertani (LB) medium supplemented with the appropriate antibiotics (rifampicin, 10 μg/ml; kanamycin, 50 μg/ml) at 28° C. The overnight bacterial cultures were washed with distilled water; induced on agro-induction medium (1/10 MS basal salt; 0.5 mg/ml 2-N-Morpholino-ethanesulfonic acid [MES] and 1% glucose) supplemented with acetosyringone (150 μg/ml) at room temperature (24° C.) for 14-16 hr. The induced cultures were washed with sterile distilled water and resuspended in 0.9% NaCl at $10^6$ cfu/ml for in vivo shoot and in vitro tumorigenesis assays, while a concentration of $10^9$ cfu/ml was used for the transient transformation assays.

For VIGS, pTRV1 and pTRV2 vectors (Lin et al., 2002) were utilized. A 414 bp fragment corresponding to NbVIP2 was amplified using the following tomato primer pairs; LeVIP2 forward 5'-GATTTCCCTCAGTTAAGCAGTCG-3' (SEQ ID NO:6) and LeVIP2 reverse 5'-GACTGCGATG-GATGGAAGAC-3' (SEQ ID NO:7) with adapter GATE-WAY primers (attB1 5'-GGGGACAAGTTTGTA-CAAAAAAGCAGGCT-3' (SEQ ID NO:8) and attB2 5'-GGGGACCACTTTGTACAAGAAAGCTGGGT-3' (SEQ ID NO:9) and cloned into pTRV2 by GATEWAY cloning according to the manufacturers suggestions (Invitrogen Life Tech, Carlsbad, Calif., USA). Agroinoculations for VIGS were done by leaf infiltration method (Ryu et al., 2004; Liu et al., 2002). Accumulation of virus in the freshly grown part of the plant was detected two weeks after inoculation by PCR with TRV coat protein-specific primers 5'-CTGGGT-TACTAGCGGCACTGAATA-3' (forward primer, SEQ ID NO:10) and 5'-TCCACCAAACTTAATCCCGAATAC-3' (reverse primer, SEQ ID NO:11). A minimum of 15 replications were performed for each experiment and the experiment was repeated at least three times.

C. Semi-quantitative RT-PCR and qRT-PCR Analyses.

For semi-quantitative RT-PCR analyses of the relative transcripts of NbVIP2 in the silenced plants and to quantify the effects of in vitro cultures on silencing, PCR amplifications were performed for 20, 25 and 30 cycles respectively. Total RNA was extracted from the leaves of NbVIP2 silenced *N. benthamiana* plants and TRV::00 plants and from representative leaf disks derived from TRV::00 and NbVIP2 silenced plants 3d, 7d and 10d post-infection (dpi) using the following primer combinations, NbVIP2 forward 5'-GATTTCCCT-CAGCTAAGCAGCC-3' (SEQ ID NO:12) and NbVIP2 reverse 5'-TGGAAGACATCTGAACCATGTAAA-3' (SEQ ID NO:13) along with *N. benthamiana* elongation factor 1α, NbEf1α (forward 5'-TGAGGCTCTTGACCAGAT-TAATGA-3' (SEQ ID NO:14); and reverse 5'-GTAAACATC-CTGAAGTGGAAGACGTA-3' (SEQ ID NO:15) as control. Similarly the relative transcript levels of a luciferase (luc) gene was determined to measure the transient expression of this gene in the promoter less GUS gene construct pKM1, by using luc-specific primers as described (Mysore et al., 1998) along with NbEf1α as control. The PCR products were sampled from each cycle, separated on a 1.8% gel, stained with ethidium bromide and the resultant band intensity of the PCR bands served as indicator for relative transcript levels in the silenced and TRV::00 plants. Similarly the presence of bar gene in a few representative GF-resistant calli derived through particle bombardment of NbVIP2 silenced plants and TRV::00 plants with 35S::bar was detected by PCR as described earlier by (Anand et al., 2003).

Real-time quantitative RT-PCR (qRT-PCR) was performed with ABI PRISM 7000 (ABI) using SYBR Green (ABI; Applied Biosystems Inc., Foster City, Calif.) as described (Ryu et al., 2004). Briefly, independent RNA samples from triplicate biological replicates (Constantin et al., 2004) were analyzed using the following primer combinations; NbVip2F forward primer 5'-AAGGTGGGAATGCTGATTATGC-3' (SEQ ID NO:16) and NbVIP2R reverse primer 5'-TCTTC-CCATTGAGAAGTGTTGCT-3' (SEQ ID NO:17). As a control for silenced and non-silenced plants, parallel reactions using NbEf1α primers were performed and the data obtained were used to normalize VIP2 transcripts from *N. benthamiana*. Each sample was run in triplicate from three independent silenced and TRV::00 plants and the entire experiment was repeated twice. The averages of the two experiments were recorded, and calculations were performed as described (Constantin et al., 2004) to determine the percentage inhibition.

Shoots of the gene-silenced plants and empty vector control plants (TRV::00), 3 wks post-TRV inoculation, were inoculated by puncturing the stem using a needle with a suspension culture of a tumorigenic *A. tumefaciens* strain A348 containing the octopine type Ti plasmid (pTiA6). Tumors on shoots were observed 4 wks after *Agrobacterium* infection.

D. Leaf Disk Transformation Assays.

Leaf explants from the gene silenced and control plants were collected 3 wks post-TRV inoculation and were washed twice with water, treated with 10% Clorox for 10 mins, and rinsed with sterile distilled water three times before punching disks using a cork borer (0.5 cm). The leaf disks (15-20 for each plant) were incubated with different *A. tumefaciens* strains (see results) for 15 minutes, blotted on sterile filter paper to remove excess bacteria, and were later transferred to plain MS basal medium (4.32 g/l MS minimal salts; Gibco-BRL, Gaithersberg, Md.). Leaf disks were co-cultivated with the bacteria at 25° C. for two days in the dark; transferred onto either MS medium for tumorigenesis assay or to CIM (4.32 μl MS minimal salts, 1 ml/l vitamin stock, 100 mg/l myo-inositol, 20 μl glucose, 0.5 mg/l 2,4-dichlorophenoxyacetic acid, 0.3 mg/ml kinetin, 5 mg/l indole acetic acid, and 0.8% phytagar with antibiotics) containing cefotaxamine (200 μg/ml) and tricarcillin (100 μg/ml) for stable and transient transformation assays. Five μg/ml GF was included in CIM for stable transformation assay. The cultures were incubated at 25.0±2.0° C.; 16 h photoperiod; 70% humidity at 150 μE sec$^{-1}$ m$^{-2}$ light intensity. Experiments were carried out with five biological replicates and repeated twice.

For transient transformation assay the leaf disks were stained with X-Gluc solution (50 mM NaH$_2$PO$_4$, 10 mM Na$_2$·EDTA, 300 mM mannitol, and 2 mM X-Gluc, pH 7.0) for 1 day at 37° C. GUS activity was analyzed using fluorometric assays (Jefferson et al., 1987). Protein extracts were prepared by grinding five to eight leaf disks/silenced line in a microfuge tube containing GUS extraction buffer (50 mM Na$_2$HPO$_4$, 5 mM dithiothreitol, 1 mM Na$_2$·EDTA, 0.1% Sarcosyl, 0.1% Triton X-100, pH 7.0). Protein concentrations of plant extracts were determined spectrophotometrically using the Bio-Rad protein assay (Bio-Rad, Richmond, Calif.) based on the Bradford method (Bradford, 1976). Fluorescence of 4-methylumbelliferone (4-MU) was measured with WALLAC 1420-11 Multilabel Counter (PerkinElmer Life Tech, Wallac OY, Turku, Finland).

E. RNA Extraction, PCR, T-DNA Integration Assay and Differential Gene Expression.

RNA extraction, first strand cDNA synthesis, semi-quantitative RT-PCR and qRT-PCR were performed using standard protocols (Ryu et al., 2004). For the T-DNA integration assay (Li et al., 2005), genomic DNA was extracted from calli (collected from a pool of two independent experiments, with five biological replicates each) produced on leaf disks of NbVIP2 silenced and TRV::00 plants that were transformed with *A. tumefaciens* strain GV2260 carrying pBISN1. Calli were washed with dimethyl sulfoxide (15% v/w) several times by vortexing to remove any attached bacteria and DNA was extracted using DNAzol (Invitrogen, Carlsbad, Calif., USA) as per manufacturer's recommendation. Semi-quantitative PCR was performed using the following primer combinations; GUS primers 5'-CGATCAGTTCGCCGATGG-3' (SEQ ID NO:18) and 5'-TCCCGCTAGTGCCTTGTCC 3' (SEQ ID NO:19) that encompasses the intron (Hwang and Gelvin, 2004); *Agrobacterium* chromosomal gene (Atu0792) primers 5'-GCGTTCGCTGGTGTCACGCC-3' (SEQ ID NO:20) and 5'-GATCAGCGGAGACCAGCTTC-3' (SEQ ID NO:21). Duplicate samples were analyzed by qRT-PCR with the primers GUS-FP 5'-AGGTGCACGGGAATATTTCG-3' (SEQ ID NO:22) and GUS-RP 5'-ACGCGTCGGGTC-GAGTT-3' (SEQ ID NO:23) to determine the abundance of integrated T-DNA. As a loading control for silenced and non-silenced plants, parallel qRT-PCR reactions using NbEf1α primers NbEfF-5'-TGAGGCTCTTGACCAGAT-TAATGA-3' (SEQ ID NO:14) and NbEfR 5'-GTAAACATC-CTGAAGTGGAAGACGTA-3' (SEQ ID NO:15) were carried out.

For differential gene expression analyses of NbVIP2, individual leaves of two separate *N. benthamiana* plants were infiltrated (using a needle-less syringe) with an avirulent *A. tumefaciens* strain A136 or a T-DNA transfer competent strain *A. tumefaciens* GV2260 carrying pBISN1 or the infiltration buffer and qRT-PCR was performed as described in Example 1, section III.

F. Characterization of Atvip2 Mutant.

Seeds of *Arabidopsis* wild-type Col-0, and T-DNA insertion mutant GABI_676A06 were germinated and the roots were subjected to transient and stable *Agrobacterium*-mediated transformation assays as described (Nam et al., 1999; Zhu et al., 2003). RT-PCR reactions were performed on cDNAs prepared from the mutant using primer combinations; AtVIP2F 5'-TGGTTCGGGCAGATCGTTTACTGC-3' (SEQ ID NO:24) and AtVIP2R 5'-GCAAGCTTG-GTCTCTTTTCC-3' (SEQ ID NO:25) to determine the presence of AtVIP2 transcript. In vitro tumorigenesis assays were performed on the axenic root segments by infecting with oncogenic *A. tumefaciens* strain A208 containing a nopaline type Ti plasmid, co-cultivated for 48 h in dark at room temperature, transferred to a hormone-free MS media supplemented with cefotaxamine and tricarcillin, and the tumor numbers and phenotypes were recorded 4-5 weeks post infection. Transient and stable GUS expression assays and the GF-resistant calli assay were performed as detailed earlier (Li et al., 2005; Mysore et al., 2000) using the disarmed *A. tumefaciens* strain GV3101 containing either pBISN1or pCAS1.

G. Bimolecular Fluorescence Complementation (BiFC) Assay.

*Agrobacterium* binary BiFC vectors (Walter et al., 2004); pSPYNE-35S and pSPYCE-35S with yellow fluorescent protein (YFP) dissected into two parts; the N-terminal (nYFP) and the C-terminal (cYFP), were used to generate GATEWAY compatible derivatives. A blunt end GATEWAY cassette, reading frame B (Invitrogen GmbH, Karlsruhe, Germany) was inserted into the EcoRV site of pBluescript SKII+ (Stratagene, La Jolla, Calif.) to obtain pBGB-EH. Subsequently, a XbaI-XhoI fragment of pBGB-EH was transferred into the XbaI-XhoI sites of pSPYNE-35S and pSPYCE-35S to obtain pSPYNE-35S_GW and pSPYCE-35S_GW, respectively. For fusion protein analyses, the full length NbVIP2 ORF was cloned into the nYFP construct (pSPYNE::VIP2); while the translational fusion of VirE2 into the cYFP construct with (pSPYCE::VirE2*) and without (pSPYCE::VirE2) the stop codon. The transcriptional factor TGA2 gene was also cloned into the cYFP construct (pSPYCE::TGA2). These constructs were transformed into *A. tumefaciens* strain GV2260 by electroporation. pCAM-BIA1390 harboring the 35S::YFP in GV2260 was used as a positive control. All the *Agrobacterium* strains were grown in LB media under appropriate antibiotics overnight, induced with acetosyringone (100 μg/ml) for 4 hrs at room temperature. *Agrobacterium* strains containing individual constructs were mixed at 1:1 ratio and infiltrated (~1.0 O.D) into the leaves of 3-4 week old *N. benthamiana* plants. The infiltrated plants were placed under dark for 72 hrs and leaf sections were examined by Leica TCS SP2 AOBS confocal laser scanning microscope with the samples excited at 514 nm 72 h post infiltration (hpi). These experiments were repeated twice.

H. Expression Profiling in vip2 Mutant in Response to *Agrobacterium* Infection

Affymetrix microarrays (*Arabidopsis* ATH1 genome array; Affymetrix, Santa Clara, Calif.) were used in expression profiling study involving At vip2 and Col-0 plants. The wild-type Col-0 and At vip2 mutant plants were infiltrated with the disarmed strain *A. tumefaciens* GV3101 (O.D$_{600}$~0.2) by a needle-less syringe. Samples were collected at 0 hpi, 48 hpi, and 72 hpi based on the previous report (Ditt et al., 2006) showing strong differential gene expression at 48 hpi in *Arabidopsis* suspension cell cultures following *Agrobacterium* infection. Preliminary experiments on Agro-infiltration in *Arabidopsis* indicated that the earliest GUS expression was observed at 48 hpi, with the GUS expression even stronger at 72 hpi which is indicative of higher transformation frequency. Leaf samples were individually pooled from the infected plants (10 plants for each time point) for RNA extraction, and few representative leaves were stained with X-Gluc to confirm GUS expression. Total RNA was extracted from two independent biological replicates as described earlier (Ryu et al., 2004). RNA was further cleaned with RNeasy Mini Kit (Qiagen Inc, Valencia, Calif.) following manufacturer's instructions and a quality check was performed using Bioanalyzer 2100 (Agilent Technologies, Foster City, Calif.). Affymetrix chip labeling, hybridization, and scanning procedures followed the instructions provided in the Affymetrix manual (www.affymetrix.com/support/technical/manual/expression-manual.affx).

I. Revalidation of the Microarray Data.

Several differentially regulated histone genes were identified from the transcriptome analysis and revalidated the Affymetrix results by qRT-PCR using the following primer combinations (Table 1).

TABLE 1

Primers used for expression studies
(SEQ ID NOs: 29-46).

| GenBank ID | Forward primer 5'-3' | Reverse primer 5'-3' |
|---|---|---|
| At4g27230 | GGAAAGCTGGAAACTGGTTGAT | GCAGAGGAAAAGCAAATGAAAAA |
| At5g10390 | CACTAATCTTTGCGCCATTCAC | CGCGAGCTGGATATCCTTAGG |
| At1g54690 | GCGGATTCAATGGCTTCAA | CACTTGCAGAAACCATGGCTAA |
| At1g51060 | CCTAACATTCACAATCTTCTTCTTCCT | CAAGAGAGTGGATTTGGTTGATTAATC |
| At5g59870 | GTTTTCGTTGCTAGTTTGTGTTTGA | CCAAATACATAGAAACTAAGATCCAAAAGC |
| At2g28740 | TGCGATCAAGAAATTCCAGAAA | CAATGCTGCCCTAATTACAACACA |
| At5g65360 | GGTTGGATTAGGTTTTGCGTTT | TTTGCTAAGGAAGGAGAGATTTTGA |
| At3g54560 | TCATCAACAAAACCACCAAGGA | TGAGTCCAAGACTACAGAAATACAAACA |
| At1g07940 | CGGAGCTCAATTCTCGGAATT | AGGAAGCTCGAGTGCCAAGTAC |

The data from two of the biological replicates used for microarray analysis and an independent third biological replicate each with three technical replicates were analyzed to quantify the relative transcript levels in At vip2 and Col-0 plants.

J. Overexpression of VIP2 in N. Benthamiana and Arabidopsis

The full length cDNAs corresponding to N. benthamiana VIP2 (GenBank accession DQ000202) and Arabidopsis VIP2 cDNA (GenBank AF295433) were RT-PCR amplified using GATEWAY primers, sequence verified and cloned into the plant expression vector pMDC32 (Curtis and Grossniklaus, 2003), under the constitutive 35S CaMV promoter, resulting in the constructs 35S:NbVIP2 and 35S:AtVIP2. For plant transformation, a modified N. benthamiana leaf disks transformation protocol described by Horsch et al., 1985 was used, while the Arabidopsis plants were transformed by floral dip method. The regenerated plants were tested for the presence of the transgenes using the GATEWAY adapter primers (attB1/B2), while the expression of the transgenes was confirmed by semi-quantitative RT-PCR using gene specific primers (SEQ ID 12, 13, 14, 15, 24, 25). Heterozygous plants over expressing the transgenes were identified and were subjected to Agrobacterium leaf transformation assays and quantified as detailed under Section C.

K. Data Analyses.

Data were subjected to analysis of variance using JMP software version 4.0.4 (SAS Institute Inc., Cary, N.C., USA) or by ANOVA. When a significant results using F-test was obtained at P=0.05, separation of treatment means was determined by Fisher's protected least significant difference (LSD).

The genes differentially expressed between wild-type and mutant was identified by pair wise comparisons were of the microarray data obtained from Col-0 and At vip2 under the same treatment conditions. Genes responsive to Agrobacterium treatment in both Col-0 and At vip2 were identified by comparing the treated samples with their 0 hr control accordingly. For each comparison, the normalized data were imported into Excel sheet and differential genes were selected using Associative Analysis algorithm developed by Dozmorov and Centola (2003). In this analysis, Bonferroni adjusted 'p' value threshold for student t-test was set at 0.05/N, N=22,000, the number of probe sets in the "reference group" (Dozmorov and Centola, 2003). The corrected p-value ensures that the overall false positive among the multiple comparisons are controlled under 0.05. To account for multiple hypotheses testing, Q-Values, an estimation of false discovery rates (FDR), were also calculated for each probe set using EDGE software (www.biostat.washington.edu/software/jstorey/edge/; Leek et al., 2006). The Q-Value for a particular probe set reflects the proportion of false positives incurred among all probe set as or more significant than the one being measured (Leek et al., 2006). For comparative gene expression analyses of histone and histone-related genes between Col-0 and At VIP2 mutant following Agrobacterium treatment, all 52 histones and histone-related genes known to be expressed (having presence call in both replicates) were clustered and visualized using TIGR Multiple Experiment Viewer (TMEV; Saeed et al., 2003; www.tm4.org/mev.html).

Example 2

Identification of AtVIP2

Figure 1:
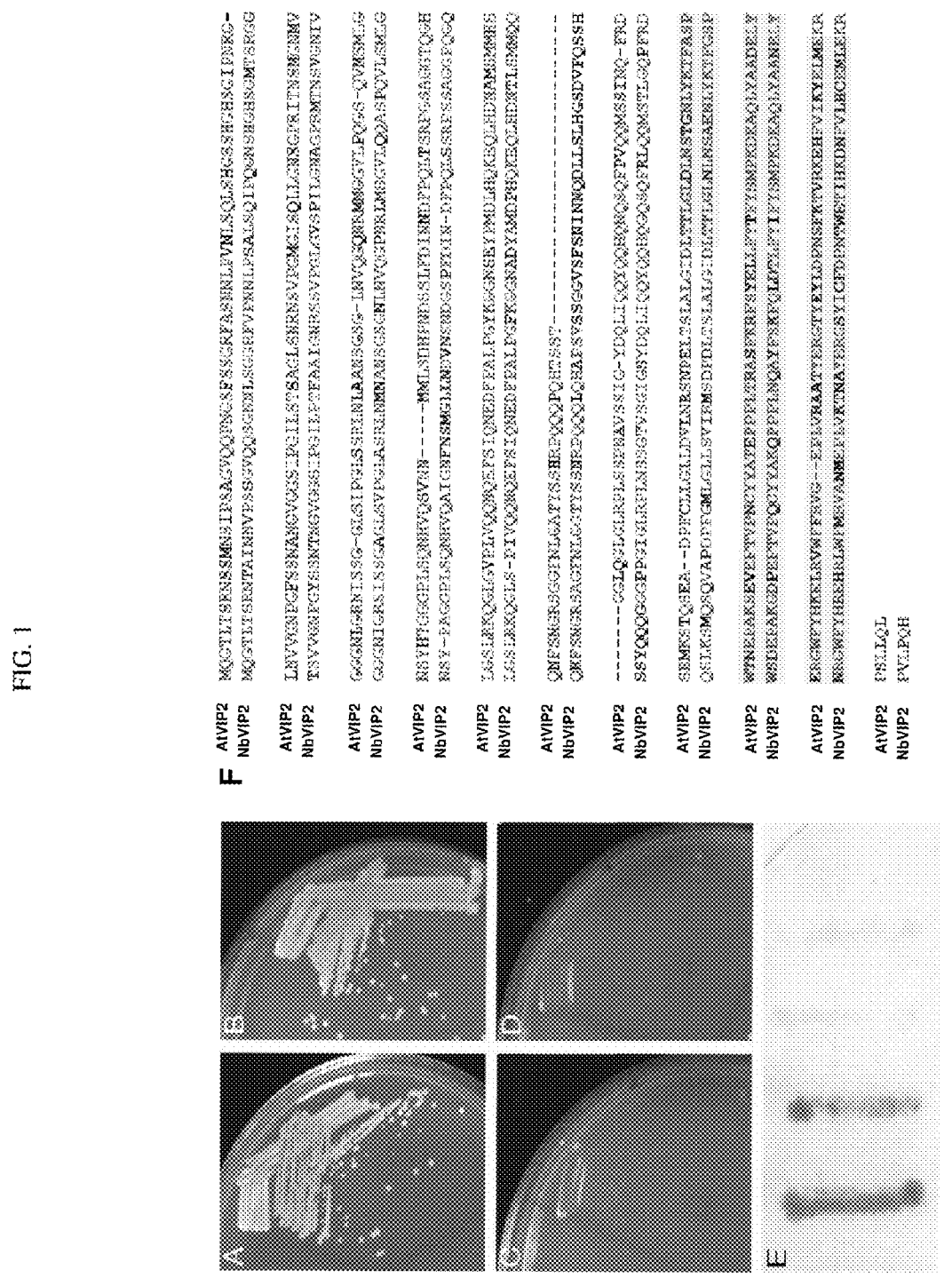

VIP2 and VIP2-like proteins contain a conserved C-terminal domain of NOT2/NOT3/NOT5 (negative on TATA-less) proteins (FIG. 1F). NOT2/NOT3/NOT5 domain containing genes were identified from Saccharomyces cerevisiae via genetic screens for increased transcription from TATA-less promoters (Oberholzer and Collart, 1998; Collart, 2003). The NOT proteins are an integral component of the CCR4 (carbon catabolite repression) transcriptional complex sharing overlapping functions (Liu et al., 1998) and are believed to be involved in both positive and negative regulation of gene expression in yeast (Collart, 2003; Collart and Timmers, 2004). The yeast Not2p and Drosophila Rga proteins that contain NOT domains are well studied and are thought to mediate intranuclear interactions between chromatin components and the transcriptional complex (Collart, 2003; Collart and Struhl, 193; Frolov et al., 1998). VirE2-interacting proteins (VIPs) were identified using the yeast two-hybrid screen with an Arabidopsis cDNA library as prey and the Agrobacterium VirE2 protein as bait, as described in Example 1 and in (Tzfira et al., 2001).

Three VirE2-interacting clones belonged to the same cDNA, which was designated AtVIP2. Co-expression of a largest clone of AtVIP2 and VirE2 (FIG. 1A), but not of lamin C (FIG. 1C) or topoisomerase I (FIG. 1D), indicated that only AtVIP2 and VirE2 co-expression activated the HIS3 and β-galactosidase (FIG. 1E) reporter genes. The interaction of AtVIP2 with VirE2 was specific because it did not occur with lamin C and DNA topoisomerase I, known as non-specific activators in the two-hybrid system best suited to eliminate false positive interactions (Bartel et al., 1993; Park and Sternglanz, 1998). AtVIP2 did not interact with VirD2 (data not shown) that is thought to function differently from VirE2 during the T-DNA nuclear import (Guralnick et al., 1996), which further reinforces its specific interaction. Interestingly AtVIP2 also interacted with AtVIP1, a previously identified VirE2 interacting protein (Tzfira et al., 2001), in the yeast two-hybrid system (FIGS. 1B, E).

Figure 3:
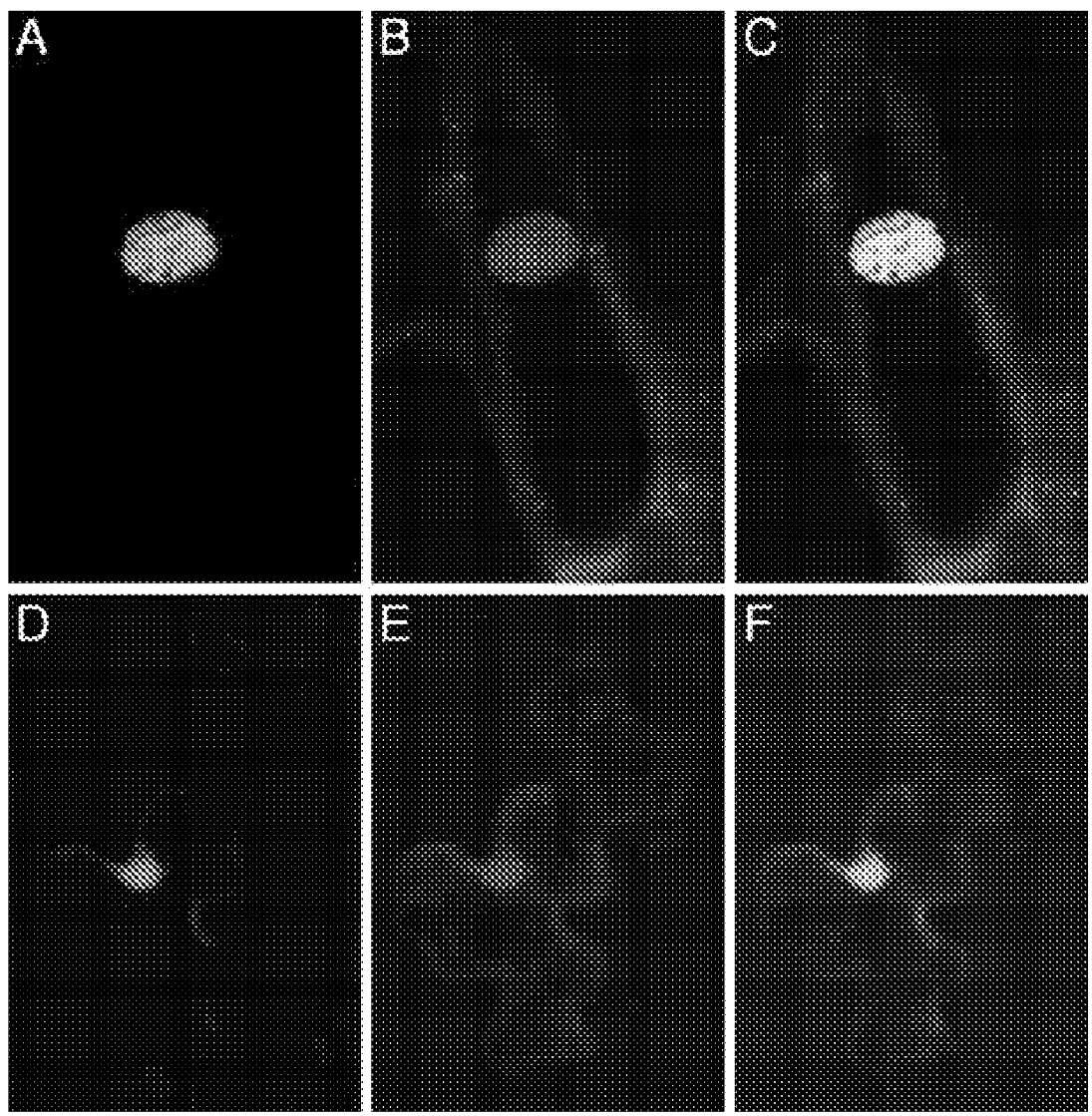
FIG. 3. Nuclear localization of GFP-AtVIP2 in plant cells (A, D) GFP-AtVIP2. (B, E) Free DsRed2 produced from the pGDR-GFP-AtVIP2-expressing construct. (C, F) Merged images. Panels A-C and D-F show expression in onion and tobacco cells, respectively. GFP is in green, DsRed2 is in red, and overlapping GFP and DsRed2 are in yellow. All images are single confocal sections.

Sequence analysis of the AtVIP2 cDNA predicted a single open reading frame (ORF) encoding a protein of 556 amino acid residues (See locus At5g59710 at www.ebi.uniprot.org for the genomic sequence of AtVIP2 carrying 11 exons and 10 introns; encoding SEQ ID NO:2). The deduced amino acid sequence of AtVIP2 contains a conserved C-terminal domain for negative on TATA-less (NOT; NOT2/NOT3/NOT5 (Collart and Struhl, 1994; Oberholzer and Collart, 1998) genes (FIG. 1F). The VIP2 gene (At5g59710) in the Arabidopsis database is represented by two splice variant cDNAs (GenBank accession no. AKI 17230 and AF295433; (Wang and Brendel, 2006). AtVIP2 is also annotated as a transcription regulator NOT2/NOT3/NOT5 protein (GenBank accession no. NM125363). There are at least two other proteins with a NOT domain in Arabidopsis (GenBank accession nos. NP568361 and NP563795) that have 15% and 61% similarity to AtVIP2, respectively (FIG. 2). The NOT domain of VIP2 is conserved among plants and animals (FIG. 2). As to VIP2 localization within the cell, it was shown that GFP-tagged VIP2 localized predominantly to the nucleus of onion and tobacco cells (FIG. 3). These results were consistent with the previous report that showed in transgenic Arabidopsis plants the YFP-tagged AtVIP2, expressed under its native promoter and terminator sequences, accumulated within the cell nucleus (Tian et al., 2004).

Example 3

NbVIP2 is Induced by Agrobacterium Infection

Figure 4:
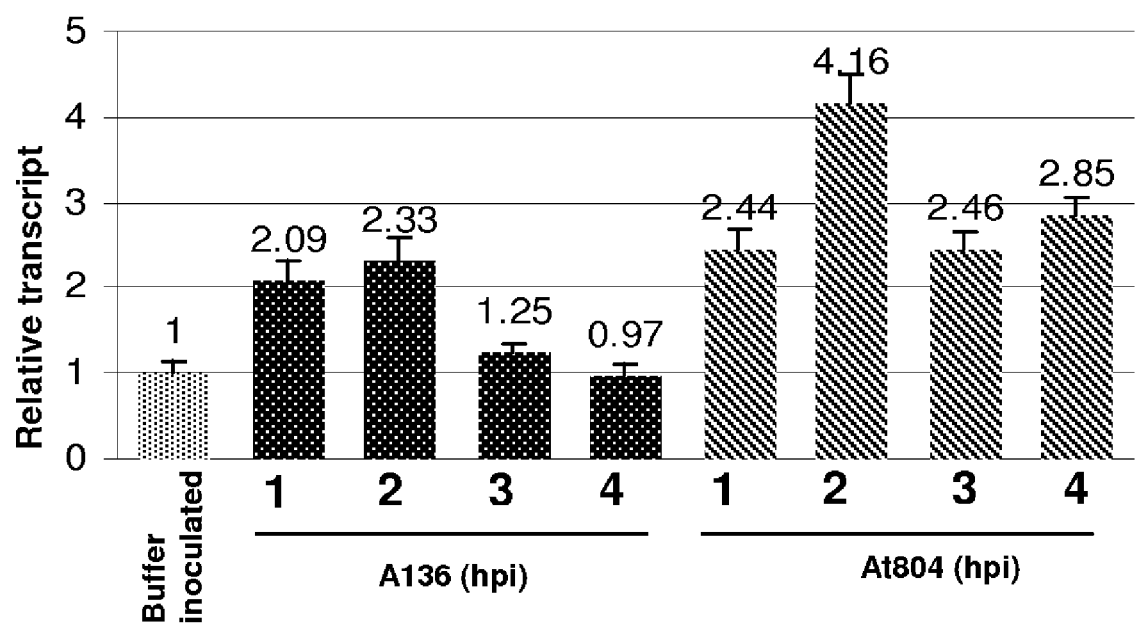
FIG. 4. Differential gene expression of the NbVIP2 upon infection with *Agrobacterium*. Individual leaves of two separate *N. benthamiana* plants were syringe (needle-less) infiltrated with either an avirulent *A. tumefaciens* strain A136 (lacks Ti plasmid; cannot transfer T-DNA) or a T-DNA transfer competent *A. tumefaciens* GV2260 carrying pBISN1. Leaf samples from the infiltrated area were collected at different times after inoculation and total RNA was isolated for real-time quantitative PCR. RNA from the buffer infiltrated *N. benthamiana* leaves collected at 12 hpi was used as a calibrator to determine the relative amount of NbVIP2 transcripts.
Figure 5:
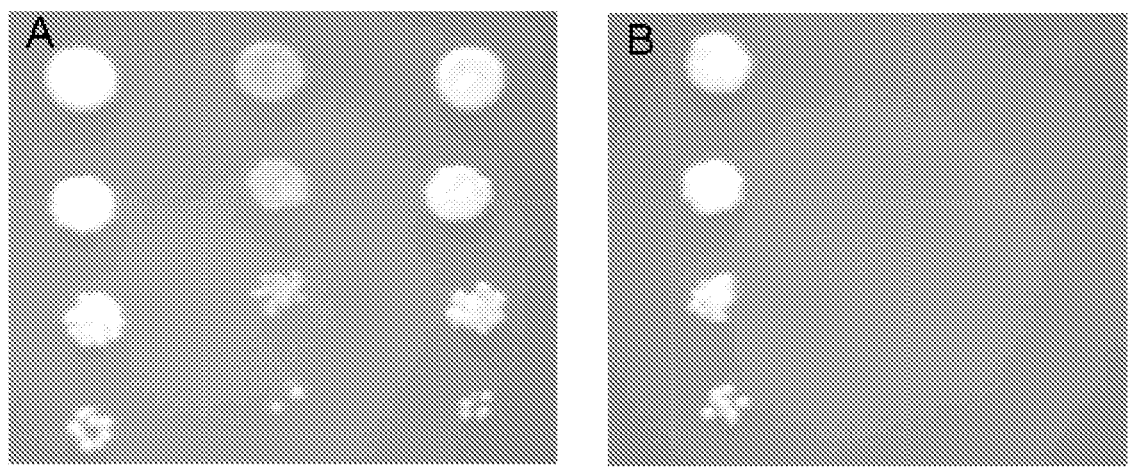
FIG. 5. Specific NbVIP2-VirE2 interaction in the yeast two-hybrid system. Yeast shown in panel A were grown on double dropout (-Leu/-Trp) plates. Yeast shown in panel B were grown on triple dropout (-Leu/-Trp/-His) plates. Both plate types contain the following plasmids combinations from left to right: pSTT-VirE2::pGAD-NbVIP2; pSTT-LaminC::pGAD-NbVIP2; pSTT-TOPI::pGAD-NbVIP2. Growth of yeast bearing pSTT-VirE2::pGAD-NbVIP2, and absence of growth of pSTT-LaminC::pGAD-NbVIP2 and pSTT-TOPI::pGAD-NbVIP2 bearing yeast, on the triple dropout plates indicate specific interaction between VirE2 and NbVIP2.

The NbVIP2 gene was induced up to two-fold following 12 h post infection (hpi) with both an avirulent A. tumefaciens strain A136 (lacks Ti plasmid) and a T-DNA transfer competent strain A. tumefaciens GV2260 carrying pBISN1, when compared with the mock inoculated N. benthamiana (FIG. 5). NbVIP2 transcripts remained elevated up to 36 hpi in leaves inoculated with A136, but decreased to basal levels at 48 hpi. In the leaves infected with T-DNA transfer competent strain, elevated transcript levels of NbVIP2 were maintained up to 48 hpi and were 2-3 fold more than those detected in A136 infected leaves (FIG. 4). These results suggest that the transfer competent Agrobacterium strain induces VIP2 gene expression to a greater extent than the avirulent strain.

Example 4

NbVIP2 Interacts with VirE2 Both in vitro and in Planta

N. benthamiana gene corresponding to NbVIP2 was cloned by RACE (Example 1). The NbVIP2 ORF is 1,812 bp in length, encoding a protein of 603 amino acid residues (GenBank accession DQ000202; SEQ ID NO:4). Sequence alignment of the NbVIP2 and AtVIP2 protein sequences showed 69% sequence identity with a conserved C-terminal NOT domain (FIG. 1F). NbVIP2 carries two in frame insertions of 5 and 32 amino acids which are lacking in AtVIP2 (FIG. 1F).

Figure 6:
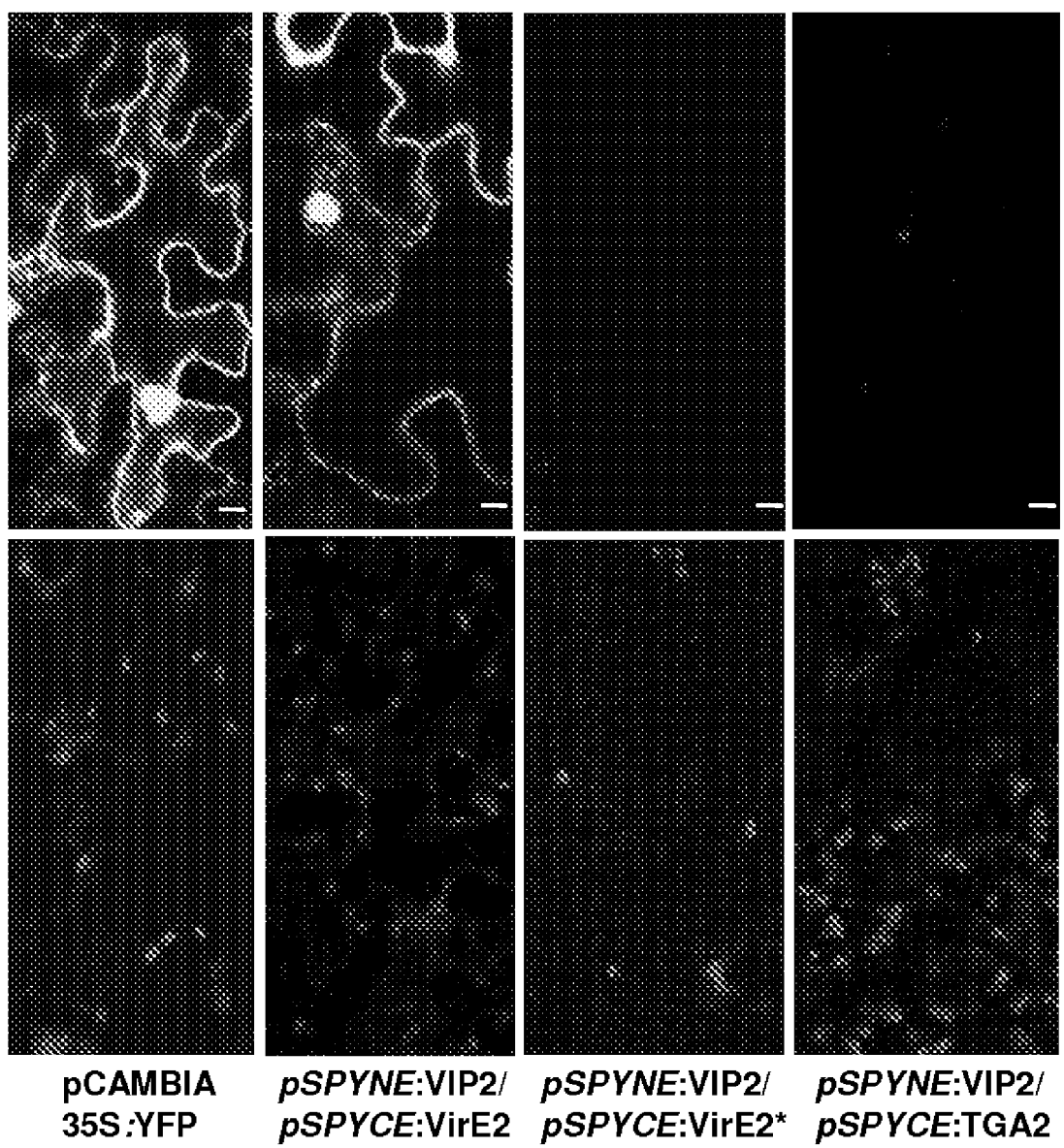
FIG. 6. In planta interaction of NbVIP2 with VirE2. The upper panel depicts the YFP fluorescence and the lower panel represents the epifluorescence images of epidermal leaf cells from the same leaf infiltrated with *Agrobacterium* suspension cultures harboring the indicated proteins. Individual leaves of *N. benthamiana* plants were syringe (needle-less) infiltrated with *Agrobacterium* suspension cultures singly or in the following combinations; pCAMBIA 1390-35S::YFP; pSPYNE::VIP2; pSPYCE::VirE2; pSPYNE::VIP2/pSPYCE::VirE2, pSPYNE::VIP2/pSPYCE::TGA2 and pSPYNE::VIP2/pSPYCE::VirE2*. Wild type 35S::YFP and fusion protein pSPYNE::VIP2/pSPYCE::VirE2 are both localized to the nucleus of plant cells, while the pSPYNE::VIP2/pSPYCE::VirE2* carrying the VirE2 stop codon and pSPYNE::VIP2/pSPYCE::TGA2 did not produce any fluorescence. All images are from a single confocal section. Scale bars 10 μm.

NbVIP2 also interacted with VirE2 in a yeast two-hybrid system and this interaction was specific since the NbVIP2 interaction did not occur with the non-specific interactors such as DNA topoisomerase I and lamin C (FIG. 5). It was further demonstrated that NbVIP2 can interact with VirE2 in planta by using binary biomolecular fluorescence complementation (BiFC; (Walter et al., 2004)). BiFC vectors were modified to make it GATEWAY ready (see Materials and Methods). The interaction between N-tagged NbVIP2 (pSPYNE::NbVIP2) and C-tagged VirE2 (pSPYCE::VirE2) was predominantly localized in the nucleus of N. benthamiana leaf epidermal cells, resulting from the reconstitution of the YFP fluorescence (FIG. 6). Two different controls were used for BiFC; firstly we made a translational fusion of full length VirE2 including the stop codon (designated as VirE2*) with cYFP in pSPYCE, and secondly we cloned the full length transcriptional factor TGA2 into pSPYCE. In the first control, no VirE2-cYFP fusion protein would be synthesized resulting in the failure of the reconstitution of YFP fluorescence when the two interactors are brought together. The second control facilitates identification of non-specific interaction of VIP2 with transcription factors. YFP fluorescence was not detected in leaves co-infiltrated with pSPYNE::NbVIP2 and pSPYCE::VirE2* or pSPYNE::NbVIP2 and pSPYCE::TGA2 (FIG. 6).

Example 5

AtVIP2 is Imported into the Plant Cell Nucleus

The subcellular localization of GFP tagged AtVIP2 in epidermal cells of tobacco and onion was examined along with another fluorescent reporter, DsRed2 (known to partition between the cell cytoplasm and the nucleus (Nam et al., 1999; Mysore et al., 1998; Rosso et al., 2003). GFP-AtVIP2 was imported into the nucleus of onion and tobacco cells displaying a predominantly intranuclear accumulation as determined by confocal microscopy with optical sections through the cell nucleus (FIG. 3). Combined image of GFP-AtVIP2 and DsRed2 fluorescence showed overlapping signal (yellow color) within the cell nucleus, confirming GFP-AtVIP2 localization within the nucleus (FIG. 3).

Example 6

Effect of VIP2 Silencing on Transformation

A. Silencing of NbVIP2 Results in Smaller Crown Galls

A virus-induced gene silencing (VIGS)-based reverse genetics approach (Burch-Smith et al., 2004) was utilized to investigate whether VIP2 is required for Agrobacterium-mediated plant transformation. A fragment representing part of NbVIP2 gene (414 bp in length) was amplified by PCR from N. benthamiana cDNA, using primers specific to tomato VIP2 (LeVIP2; GenBank accession No. BG130671), and cloned into Tobacco rattle virus—(TRV) based VIGS vectors (Liu et al., 2002a; Liu et al., 2002b). The reduction of NbVIP2 transcripts was quantified by semi-quantitative RT-PCR (FIG. 7) and by real-time quantitative RT-PCR (qRT-PCR) analyses. Only 23±4% mRNA of NbVIP2 was detected in gene silenced plants when compared to TRV::00 (virus without the insert) inoculated plants.

To test whether VIP2 is required for Agrobacterium infectivity, the stems of NbVIP2 silenced, TRV::00 inoculated and wild-type (no virus inoculation) plants were infected with oncogenic A. tumefaciens strain A348. Relatively smaller tumors were incited on the shoots of NbVIP2 silenced plants when compared to the tumors on the TRV::00 inoculated plants or wild-type plants (FIG. 7).

B. NbVIP2 is Required for Stable Transformation.

Figure 8:
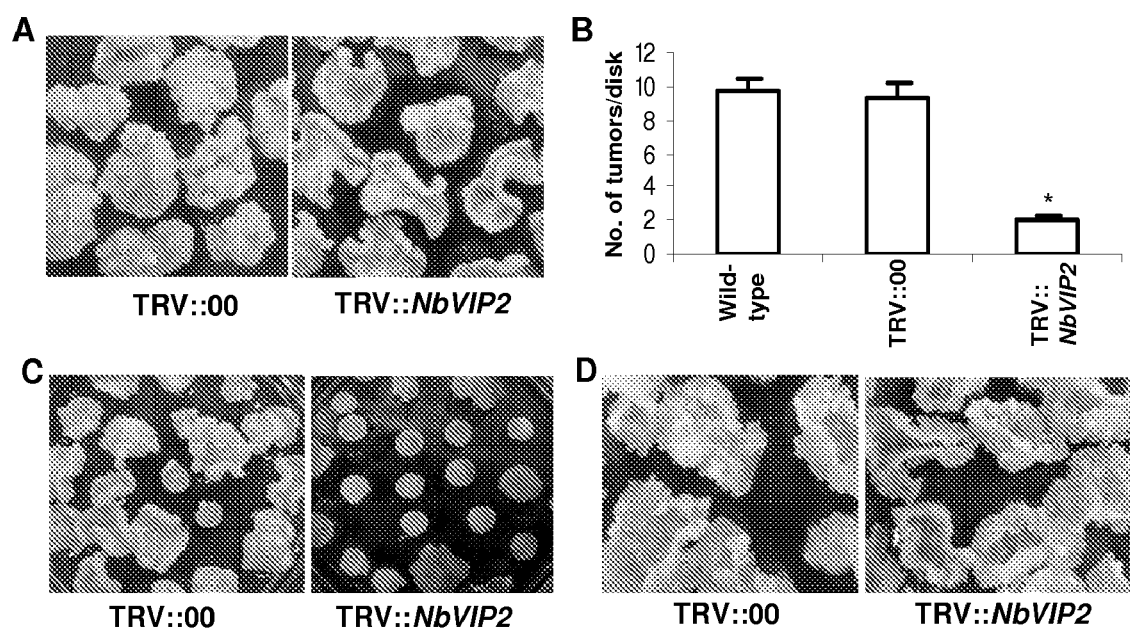
FIG. 8. *Agrobacterium* transformation assays in NbVIP2 silenced plants. (A) Leaf disk tumorigenesis assay. Leaf disks of the NbVIP2 silenced plants and TRV::00 (control) plants were inoculated with tumorigenic *A. tumefaciens* strain A348 and incubated on hormone free MS medium. Photographs were taken four weeks after *Agrobacterium* infection. (B) Quantification of tumors. The number of tumors produced per leaf disk was counted three weeks after inoculation. (C) Stable transformation assay.

The ability of NbVIP2 silenced plants to develop tumors on leaf disks was tested following inoculation with A. tumefaciens strain A348. Tumors were quantified by counting the number of tumors/leaf disk and by measuring the weight of leaf disks with tumors (FIG. 8; FIG. 9). The tumor inducing capability was severely attenuated in NbVIP2 silenced plants when compared to TRV::00 and wild-type plants.

To rule out the possibility that the reduction in number of tumors produced in NbVIP2 silenced plants could have resulted from the down-regulation of gene(s) involved in phytohormone responses, leaf disks from the NbVIP2 silenced and TRV::00 plants were inoculated with a non-tumorigenic *A. tumefaciens* strain, GV2260, containing the binary vector pCAS1 (Nam et al., 1999) that contains a nos-bar gene as a selectable marker. Approximately, 33% of the leaf disks derived from the NbVIP2 silenced plants survived the glufosinate ammonium (GF)-selection and produced small transgenic GF-resistant calli on callus inducing medium (CIM). In the case of TRV::00 and wild-type control plants, 100% of the leaf disks survived GF-selection and produced predominantly large GF-resistant calli (FIG. 8C).

Interestingly, VIP2 gene silencing in *N. benthamiana* did not affect both transient and stable transformation by particle bombardment. Uninfected leaf disks of NbVIP2 silenced plants were able to form calli, at an equal efficiency as that of TRV::00 plants, on non-selective CIM (FIG. 8D). Thus, silencing of VIP2 gene apparently does not interfere with essential plant cellular functions pertaining to cell division. These data clearly indicate that silencing of VIP2 in *N. benthamiana* attenuates *Agrobacterium*-mediated stable transformation.

C. NbVIP2 Silenced Plants are Partially Blocked at the T-DNA Integration Step.

To identify the step at which VIP2 is involved in *Agrobacterium*-mediated transformation, leaf disks derived from the NbVIP2 silenced *N. benthamiana* and TRV::00 plants were inoculated with a disarmed *A. tumefaciens* strain GV2260 containing the binary vector pBISN1 which carries on its T-DNA a uidA-intron gene encoding β-glucoronidase (GUS; Nam et al., 1999). 5-bromo-4-chloro-3-indolyl b-D-glucuronide (X-Gluc) staining and GUS activity on the leaf disks of NbVIP2 silenced plants were not significantly different than TRV::00 plants at 2 and 3 days post inoculation (dpi) FIG. 10), suggesting that there was no deficiency in transient transformation in the silenced plants. Also, no qualitative differences in the transient GUS expression were detected, when the uidA-intron gene was delivered by agro-infiltration, in the NbVIP2 silenced and TRV::00 plants (FIG. 13B). Leaf disks from NbVIP2 silenced plants showed less X-Gluc staining and only 61-65% GUS activity when compared to leaf disks derived from the TRV::00 plants at 5-10 dpi (FIG. 10). This represents a combination of both transient and stable GUS expression. Thus, NbVIP2 gene silencing partially blocked the later stages (T-DNA integration) of *Agrobacterium*-mediated transformation.

To provide additional evidence that the T-DNA integration was blocked in NbVIP2 silenced plants, the leaf disks derived from NbVIP2 silenced and TRV::00 plants were inoculated with a disarmed *A. tumefaciens* strain GV2260 containing the binary vector pKM1 (Mysore et al., 1998) carrying a promoterless uidA-intron gene and a 35S::luciferase (luc)-intron gene within the T-DNA. Here the expression of uidA gene in plants is dependent upon T-DNA integration downstream of a plant promoter, while the luc gene can express transiently irrespective of T-DNA integration. Significantly less GUS activity were detected on the leaf disks of NbVIP2 silenced plants at 9-15 dpi when compared with the TRV::00 plants (FIG. 10C; FIG. 11A). As a positive control for *Agrobacterium* infectivity, expression of the luc gene was detected in the representative leaf disks derived from the same experiment for NbVIP2 silenced and TRV::00 plants by semi-quantitative RT-PCR (FIG. 11B).

In order to provide direct evidence for deficiency in T-DNA integration in Nb VIP2 silenced plants, DNA-blot analyses (Mysore et al., 2000) were performed on high molecular weight DNA extracted from cell cultures of Nb VIP2 silenced and TRV:00 plants infected with a disarmed strain *A. tumefaciens* GV2260 containing the binary vector pBISN1 (Nam et al., 1999). The differences in the amount of T-DNA, containing uidA-intron gene, integrated into the genomes of Nb VIP2 silenced and TRV:00 plants was determined by hybridizing the above mentioned DNA-blot with radiolabeled uidA gene. DNA from Nb VIP2 silenced plants showed weaker signals when compared to DNA from TRV:00 plants (FIG. 11C). Nb H3 silenced plants have been recently shown to be deficient in T-DNA integration (Anand et al., 2007b). DNA from Nb H3 silenced plants infected with *A. tumefaciens* GV2260 containing pBISN1 was used as control. The plant DNA samples were confirmed to be free of contaminating *A. tumefaciens* DNA by performing quantitative DNA PCR using a bacterial chromosomal gene Atu0972 as previously described (Anand et al., 2007b). The same DNA blot was stripped and re-hybridized with radiolabeled Nb RAR1 gene to demonstrate that similar amounts of DNA were loaded in lanes with DNA from Nb VIP2 and Nb H3 cultures with respect to DNA from TRV:00 cultures (FIG. 11C).

To confirm further that the NbVIP2 silenced plants were deficient in T-DNA integration, real-time quantitative PCR (qPCR) was performed as described (Li et al., 2005) on genomic DNA extracted from calli generated on leaf disks (without any selection) that were inoculated with the disarmed *A. tumefaciens* strain containing the binary vector pBISN1. The amount of PCR products specific to uidA gene, determined by qPCR, was ~63% lesser in NbVIP2 silenced plants when compared to TRV::00 plants (FIG. 10D). Semi-quantitative PCR amplifications were also performed using primers specific to exons bordering an intron and primers specific to bacterial chromosome to show the specific amplification of integrated T-DNA molecule (FIG. 11D). Based on these results, it is suggested that VIP2 plays a crucial role in T-DNA integration.

Example 7

An *Arabidopsis* vip2 Mutant is Defective in T-DNA Integration but not in Transient T-DNA Expression An *Arabidopsis* T-DNA mutant line (GABI_676A06; T-DNA insertion in the second exon; Rosso et al., 2003) was identified that does not produce an AtVIP2 transcript. To further confirm the results obtained from NbVIP2 silenced plants, root transformation assays were performed on Atvip2 plants. Upon infection with an oncogenic *Agrobacterium* strain, Atvip2 mutant produced fewer tumors (38±3% of the infected roots formed tumors) as compared to the wild-type plants (87±5% of the infected roots formed tumors; (FIG. 12A; FIG. 2). No significant differences, however, were observed between the wild-type and Atvip2 mutant for transient GUS expression at 2 dpi (FIG. 12B). Stable GUS expression in the Atvip2 mutant was significantly lower (25±6% of calli showed GUS staining) when compared to the wild-type plants (100% of calli showed GUS staining; FIG. 12B). Subsequently, a stable transformation assay was performed with the disarmed *Agrobacterium* strain containing pCAS1. Significantly reduced numbers of GF-resistant calli were observed in the Atvip2 mutant (33±1% of infected roots formed GF resistant calli), relatively to the wild-type plants (83±3% of infected roots formed GF resistant calli). Root segments derived from both the wild-type and Atvip2 mutant plants were able to form calli at similar frequencies on non-selective CIM. These results further support the role of VIP2 in T-DNA integration in another plant species.

Example 8

Transcriptome Analyses Suggest that VIP2 Plays a Role in Transcription Regulation In order to gain insight on the biological role of VIP2 in plants, a comprehensive survey of global gene expression was done by using *Arabidopsis thaliana* whole genome Affymetrix gene chip (ATH1) to quantify the spatio-temporal variations in transcript abundance between wild-type Col-0 and At vip2. Comparative analyses between Col-0 and At vip2 showed 4,241 genes to be constitutively differentially expressed with a false discovery rate (FDR) less than 10%. Out of the 4,241 differentially expressed genes, 2,157 genes had more transcript abundance in At vip2 when compared to Col-0 whereas 2,084 genes had more transcript abundance in Col-0 when compared to At vip2 (Anand et al., 2007b). Functional classification of the 4,241 differentially expressed genes indicated genes involved in a variety of functions and the majority (28.7%) of them encodes proteins of unknown function (FIG. 14). These data support the hypothesis that VIP2 has a direct or indirect role in transcription regulation of many genes. Interestingly, upon careful examination of the transcriptome data, it was found that a majority of the 52 genes encoding histones or histone-associated proteins to be constitutively repressed in the At vip2 when compared to Col-0 plants (FIG. 14; Anand et al., 2007b). Although, the transcript differences of some of the histone genes were less than two-fold, their expression profile were obviously different in At vip2 and Col-0 plants (FIG. 15). The exact expression values of these genes are shown in Supplemental Table 3. Histones have already been implicated in *Agrobacterium*-mediated plant transformation (Mysore et al., 2000; Yi et al., 2002; Li et al., 2005; Yi et al., 2006; Anand et al., 2007a).

The differential expression of genes in At vip2 mutant and Col-0 in response to *Agrobacterium* infection were monitored by infiltrating the leaves with a disarmed strain *A. tumefaciens* GV3101 harboring the uidA-intron gene as described (Wroblewski et al., 2005). Under the same selection condition, strikingly, fewer genes were differentially expressed in At vip2, at 48 hpi and 72 hpi, when compared to the number of genes that were differentially expressed in Col-0 plant at the same time points (Supplemental Table 4). The fact that 100% transformation was not seen in the infiltrated plants, based on the GUS histochemical staining (FIG. 16) could have diluted the effect on differential gene expression upon *Agrobacterium* infection. Nevertheless, the data show that At vip2 is significantly muted in its response, based on differential gene expression, to *A. tumefaciens* infection. These results further validate the role of VIP2 in transcriptional regulation and *Agrobacterium*-mediated plant transformation.

Example 9

Real-time Quantitative RT-PCR Showed that Reduced Transcript Levels of Several Histone Genes in at vip2 Mutant when Compared to Wild-type *Arabidopsis*

The microarray results for a number of histone genes were validated, and differential expression between wild-type Col-0 and At vip2 was shown. Eight histone genes that showed less transcript abundance in At vip2 when compared to Col-0 were selected for the qRT-PCR analysis. Five different members of histone H2A viz. HTA10 (At1g51060), HTA3 (At1g54690), HTA6 (At5g59870), HTA2 (At4g27230) and HTA11 (At3g54560); two Histone H3 genes (At5g65360, At5g10390); and one Histone H4 (At2g28740) were selected. The transcript abundance of all the eight genes tested were significantly less in At vip2 when compared to Col-0 at one or the other time point (FIG. 17). For all the histone genes tested, qRT-PCR results strongly correlated with the microarray data except for HTA3 (At1g54690) that did not show any significant difference in the expression between Col-0 and At vip2 at 0 hpi. However, lesser transcripts of HTA3 in At vip2 mutant when compared to Col-0 were observed at 48 hpi and 72 hpi post *A. tumefaciens* infection. These results further imply that VIP2 plays a role in *Agrobacterium*-mediated plant transformation by modulating the expression of several plant histone genes.

Example 10

Transgenic Plants Over Expressing VIP2 Showed Increased Susceptibility to *Agrobacterium* Infection To examine whether VIP2 may represent one of the limiting cellular factors during *Agrobacterium* infection, transgenic *N. benthamiana* and *Arabidopsis* plants were constructed that over express the *N. benthamiana* VIP2 cDNA (GenBank accession DQ000202) and *Arabidopsis* VIP2 cDNA (GenBank AF295433). 11 independent transgenic *N. benthamiana* lines overexpressing NbVIP2 were generated and evaluated, and 2 independent heterozygous transgenic lines were identified that had increased transcript levels (FIG. 18A), which are designated NbVIP2-E5 and NbVIP2-E7 for transient and stable transformation. Similarly, one *Arabidopsis* line (AtVIP2-E1) with increased expression of the transgene (FIG. 18B) was also screened for stable transformation. The relative transcript levels in the transgenic lines were quantified by semi-quantitative RT-PCR (FIG. 18) using the primers detailed in materials and methods. The transgenic lines NbVIP2-E5 and E7 showed increased transient expression of *Agrobacterium* T-DNA at 2 dpi and 7 dpi (FIG. 19A), suggesting overexpression of VIP2 supposedly increases the early steps of transformation. The transgenic lines NbVIP2-E5 and E7 also produced higher number of stably transformed tumor phenotypes upon infection with *A. tumefaciens* strain A348 (FIG. 19B). Similarly, the transgenic line AtVIP2-E1 produced more number of tumors when infected with low concentration of the oncogenic strain A208 as compared to the wild-type Col-0 plants (FIG. 19C).

* * * * * * * *

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for, or teach methodology, techniques, and/or compositions employed herein.

U.S. Pat. Nos. 4,535,060; 5,302,523; 5,322,783; 5,384,253; 5,384,253; 5,464,765; 5,508,184; 5,538,877; 5,538,880; 5,545,818; 5,550,318; 5,563,055; 5,563,055; 5,591,616; 5,610,042; 5,591,616

U.S. Publn. 20030233676

Abdullah et al., *Biotechnology*, 4:1087, 1986.
Altschul et al., *J. Mol. Biol.*, 215:403-410, 1990.
Anand and Mysore, In: *Advances Plant Physiol.*, Scientific Publishers, Jodhpur, 2005.
Anand et al., *J. Exp. Bot.*, 54:1101-1111, 2003.
Anand A, et al., *Mol. Plant-Microbe Interact.* 20:41-52, 2007a.
Anand A, et al., *Plant Cell* 19:1695-1708, 2007b.
Ballas and Citovsky, *Proc. Natl. Acad. Sci. USA*, 94:10723-10728, 1997.
Bartel et al., *BioTechniques*, 14:920-924, 1993.
Bates, *Mol. Biotechnol.*, 2(2):135-145, 1994.
Battraw and Hall, *Theor. App. Genet.*, 82(2):161-168, 1991.
Bevan et al., *Nucleic Acids Res.*, 11(2):369-385, 1983.
Bhattacharjee et al., *J. Plant Bioch. Biotech.*, 6(2):69-73. 1997.
Biocomputing: Informatics and Genome Projects, Smith (Ed.), Academic Press, NY, 1993.
Birren, et al., *Genome Analysis*, 1:543-559, 1997.
Bower et al., *Plant J.*, 2:409-416. 1992.
Bradford, *Anal. Biochem.* 72:248-254, 1976.
Buising and Benbow, *Mol. Gen. Genet.*, 243(1):71-81, 1994.
Burch-Smith et al., *Plant J.*, 39:734-746, 2004.
Callis et al., *Genes Dev.*, 1:1183-1200, 1987.
Carillo and Lipman, *J. Applied Math.*, 48:1073, 1988.
Casas et al., *Proc. Natl. Acad. Sci. USA*, 90:11212-11216, 1993.
Cascales and Christie, *Science*, 304:1170-1173, 2004.
Chandler et al., *Plant Cell*, 1:1175-1183, 1989.
Christie, *Biochem. Biophys. Acta*, 1694:219-234, 2004.
Christou et al., *Proc. Natl. Acad. Sci. USA*, 84:3962-3966, 1987.
Chu et al., *Scientia Sinica*, 18:659-668, 1975.
Collart and Struhl, *EMBO J.*, 12:177-186, 1993.
Collart and Struhl, *Genes Dev.*, 8:525-537, 1994.
Collart and Timmers, *Prog. Nucl. Acid Res. Mol. Biol.*, 77:289-322, 2004.
Collart, *Gene*, 313:1-16, 2003.
Computational Molecular Biology, Lesk (Ed.), Oxford University Press, NY, 1988.
Computer Analysis Sequence Data, Part I, Griffin and Griffin (Eds.), Humana Press, NY, 1994.
Conkling et al., *Plant Physiol.*, 93:1203-1211, 1990.
Constantin et al., *Plant J.*, 40:622-631, 2004.
Coulson, *Trends in Biotech.*, 12:76-80, 1994.
Curtis and Grossniklaus, *Plant Physiol.* 133:462-469, 2003.
D'Halluin et al., *Plant Cell*, 4:1495-1505, 1992.
DE 3642 829 A
Dellaporta et al., In: *Chromosome Structure and Function: Impact of New Concepts*, 18th Stadler Genetics Symposium, 11:263-282, 1988.
Devereux et al., *Nucl. Acid Res.*, 12(1):387-395, 1984.
Ditt et al., *Mol. Plant. Microbe Interact.* 19:665-681, 2006.
Dozmorov and Centola, *Bioinformatics*, 19:204-211, 2003.
Durfee et al., *Genes Dev.*, 7:525-537, 1993.
Ebert et al., *Proc. Natl. Acad. Sci. USA*, 84:5745-5749, 1987.
EP 154,204
Fraley et al., *Bio/Technology*, 3:629-635, 1985.
Frolov et al., *Genetics*, 148:317-330, 1998.
Fromm et al., *Nature*, 319(6056):791-793, 1986.
Gallie et al., *Plant Cell*, 1:301-311, 1989.
Gelvin et al., In: *Plant Molecular Biology Manual*, Kluwer Academic Publishers, 1990.
Gelvin, *Microbiol. Molec. Biol. Rev.*, 67:16-37, 2003.
Ghosh-Biswas et al., *J. Biotechnol.*, 32(1):1-10, 1994.
Guralnick et al., *Plant Cell*, 8:363-373, 1996.
Hagio et al., *Plant Cell Rep.*, 10(5):260-264, 1991.
Hamilton et al., *Proc. Natl. Acad. Sci. USA*, 93:9975-9979, 1996.
Haseloff et al., *Proc. Natl. Acad. Sci. USA*, 94(6):2122-2127, 1997.
He et al., *Plant Cell Reports*, 14 (2-3):192-196, 1994.
Hensgens et al., *Plant Mol. Biol.*, 22(6):1101-1127, 1993.
Hentikoff and Hentikoff, *Proc. Natl. Acad. Sci. USA*, 89:10915-10919, 1992.
Hiei et al., *Plant. Mol. Biol.*, 35(1-2):205-218, 1997.
Hinchee et al., *Bio/Technology*, 6:915-922, 1988.
Hollenberg et al., *Mol. Cell. Biol.*, 15:3813-3822, 1995.
Horsch et al., *Science*, 227:1229-1231, 1985
Hou and Lin, *Plant Physiology*, 111:166, 1996.
Hudspeth and Grula, *Plant Mol. Biol.*, 12:579-589, 1989.
Hwang and Gelvin, *Plant Cell* 16, 3148-3167, 2004.
Ikuta et al., *BioTechnol.*, 8:241-242, 1990.
Ishida et al., *Nat. Biotechnol.*, 14(6):745-750, 1996.
Jefferson et al., *EMBO J.*, 6:901-907, 1987.
Kaeppler et al., *Plant Cell Rep.*, 8:415-418, 1990.
Kaeppler et al., *Theor. Appl. Genet.*, 84(5-6):560-566, 1992.
Kaiser et al., Cold Spring Harbor Laboratory Press, Cold Spring Harbor, N.Y., 1994.
Karlin and Altschul, *Proc. Natl. Acad. Sci. USA* 87:2264-68, 1990.
Karlin and Altschul, *Proc. Natl. Acad. Sci. USA* 90:5873-7, 1993.
Katz et al., *J. Gen. Microbiol.*, 129:2703-2714, 1983.
Klee et al., *Bio-Technology*, 3(7):637-642, 1985.
Knittel et al., *Plant Cell Reports*, 14(2-3):81-86, 1994.
Lawton et al., *Plant Mol. Biol.* 9:315-324, 1987.
Lazzeri, Methods Mol. Biol., 49:95-106, 1995.
Lee et al., *Korean J. Genet.*, 11:65-72, 1989.
Leek et al., *Bioinformatics*, 22:507-508, 2006.
Li et al., *Proc. Natl. Acad. Sci. USA*, 102:19231-19236, 2005.
Liu et al., *EMBO J.*, 17:1096-1106, 1998.
Liu et al., *Plant J.*, 31:777-786, 2002a.
Liu et al., *Plant J.*, 30:415-429, 2002b.
Lorz et al., *Mol Gen Genet*, 199:178-182, 1985.
Marcotte and Bayley, *Nature*, 335(6189):454-457, 1988.
McCabe and Martinell, *Bio-Technology*, 11(5):596-598, 1993.
McCormac et al., *Euphytica*, 99(1):17-25, 1998.
Murashige and Skoog, *Physiol. Plant*, 15:473-497, 1962.
Mysore et al., *Mol. Plant-Microbe. Interact.*, 11:668-683, 1998.
Mysore et al., *Proc. Natl. Acad. Sci. USA*, 97:948-953, 2000.
Nagatani et al., *Biotech. Tech.*, 11(7):471-473, 1997.
Nam et al., *Mol. Gen. Genet.*, 261:429-438, 1999.
Needleman and Wunsch, *J. Mol. Biol.*, 48:443-453, 1970.
Oberholzer and Collart, *Gene*, 207:61-69, 1998.
Odell et al., *Nature*, 313:810-812, 1985.
Ogawa et al., *Sci. Rep.*, 13:42-48, 1973.

Omirulleh et al., *Plant Mol. Biol.,* 21(3):415-428, 1993.
Ow et al., *Science,* 234:856-859, 1986.
Park and Sternglanz, *Chromosoma,* 107:211-215, 1998.
PCT Appln. WO 9217598
PCT Appln. WO 94/09699
PCT Appln. WO 95/06128
PCT Appln. WO 95/06128
PCT Appln. WO 97/41103
PCT Appln. WO 97/41228
Potrykus et al., *Mol. Gen. Genet.,* 199(2):169-177, 1985.
Reichel et al., *Proc. Natl. Acad. Sci. USA,* 93:5888-5893, 1996.
Rhodes et al., *Methods Mol. Biol.,* 55:121-131, 1995.
Ritala et al., *Plant Mol. Biol.,* 24(2):317-325, 1994.
Rogers et al., *Methods Enzymol.,* 153:253-277, 1987.
Rosso et al., *Plant Mol. Biol.,* 53:247-259, 2003.
Ryu et al., *Plant J.,* 40:322-331, 2004.
Saeed et al., *Biotechniques,* 34:374-8, 2003.
Sambrook et al., In: *Molecular cloning: a laboratory manual,* 2d Ed., Cold Spring Harbor Laboratory Press, Cold Spring Harbor, N.Y., 1989.
Sequence Analysis in Molecular Biology, von Heinje (Ed.), Academic Press, 1987.
Sequence Analysis Primer, Gribskov, and Devereux (Eds.), Stockton Press, NY, 1991.
Sheen et al., *Plant J.* 8:777-784, 1995.
Singsit et al., *Transgenic Res.,* 6(2):169-176, 1997.
Smith and Waterman, *J. Mol. Biol.,* 147:195-197, 1981.
Spencer et al., *Plant Mol. Biol.,* 18(2):201-210, 1992.
Stalker et al., *J. Biol. Chem.,* 263:6310-6314, 1988.
Sullivan et al., *Mol. Gen. Genet.,* 215(3):431-440, 1989.
Sutcliffe et al., *Proc. Natl. Acad. Sci. USA,* 75:3737-3741, 1978.
Thillet et al., *J. Biol. Chem.,* 263:12500-12508, 1988.
Thompson et al., *Nature Medicine,* 1:277-278, 1995.
Tian et al., *Genes Dev.,* 11(1):72-82, 1997.
Tian et al., *Plant Physiol.,* 135:25-38, 2004.
Tingay et al., *J. Plant,* 11(6):1369-1376. 1997.
Tomes et al., *Plant. Mol. Biol.,* 14(2):261-268, 1990.
Torbet et al., *Crop Science,* 38(1):226-231, 1998.
Torbet et al., *Plant Cell Reports,* 14:635-640, 1995.
Toriyama et al., *TheorAppl. Genet.,* 73:16, 1986.
Tsukada et al., *Plant Cell Physiol.,* 30(4)599-604, 1989.
Tzfira and Citovsky, *Curr. Opin. Biotechnol.,* 17:147-154, 2006.
Tzfira and Citovsky, *Mol. Plant. Pathol.,* 1:201-212, 2000.
Tzfira et al., *EMBO J.,* 20:3596-3607, 2001.
Tzfira et al., *EMBO J.,* 20:3596-3607, 2001.
Tzfira et al., *Nature,* 431:87-92, 2004.
Uchimiya et al., *Mol. Gen. Genet.,* 204(2):204-207, 1986.
Van Eck et al., *Plant Cell Reports,* 14(5):299-304, 1995.
Vasil et al., *Plant Physiol.,* 91:1575-1579, 1989.
Veena et al., *Plant J.,* 35:219-226, 2003.
Vergunst et al., *Plant Physiol.,* 133:978-988, 2003.
Vergunst et al., *Science,* 290:979-982, 2000.
Walker et al., *Proc. Natl. Acad. Sci. USA,* 84:6624, 1987.
Walter et al., *Plant J.,* 40:428-438, 2004.
Wang and Brendel, *Proc. Natl. Acad. Sci. USA,* 103:7175-7180, 2006.
Wang et al., *Am. J. Physiol.,* 263(4 Pt 1):G480-486, 1992.
Wroblewski et al., *Plant Biotechnol J.* 3:259-73, 2005.
Yamada et al., *Plant Cell Rep.,* 4:85, 1986.
Yang and Russell, *Proc. Natl. Acad. Sci. USA,* 87:4144-4148, 1990.
Yi et al., *Plant J.* 32:285-298, 2002.
Yi et al., *Plant Cell* 18:1575-1589, 2006.
Zheng and Edwards, *J. Gen. Virol.,* 71:1865-1868, 1990.
Zhou et al., *Exp. Hematol,* 21:928-933, 1993.
Zhu et al., *Plant Physiol.,* 132:494-505, 2003.
Zukowsky et al., *Proc. Natl. Acad. Sci. USA,* 80:1101-1105, 1983.

What is claimed is:

1. A transgenic plant or part thereof transformed with a polynucleotide sequence encoding a VireE2-Interacting-Protein (VIP2) polypeptide, operably linked to a heterologous promoter functional in the plant or part thereof, wherein the plant or part thereof exhibits increased transformability by *Agrobacterium*-mediated transformation relative to a plant or part thereof lacking the polynucleotide sequence.

2. The transgenic plant or part thereof of claim 1, wherein the VIP2 polypeptide is encoded by a nucleic acid sequence selected from the group consisting of:

(a) a nucleic acid sequence encoding the polypeptide of SEQ ID NO:1, 2, or 4;

(b) a nucleic acid comprising the sequence of SEQ ID NO:3 or 26;

(c) a nucleic acid sequence encoding a protein with VIP2 activity and at least 85% sequence identity to SEQ ID NO:3 or 26 over the full length of the coding sequence; and (d) a nucleic acid sequence complementary to the full length of the nucleic acid sequences of (a), (b), or (c).

3. A cell of the transgenic plant of claim 1.

4. A seed of the transgenic plant of claim 1, wherein the seed comprises the polynucleotide sequence.

5. A method of increasing the transformability of a plant cell by *Agrobacterium*-mediated transformation, comprising:

expressing in the plant cell a recombinant nucleic acid sequence comprising a polynucleotide sequence encoding a VIP2 polypeptide operably linked to a heterologous promoter functional in a plant cell.

6. The method of claim 5 wherein the plant cell is transformed with an *Agrobacterium* transformation vector comprising a T-DNA sequence, simultaneously with the VIP2 encoding sequence or following transformation of the plant cell with a VIP2 encoding sequence.

7. The method of claim 5, wherein the cell is stably transformed with the polynucleotide sequence.

8. The method of claim 5, wherein the cell transiently expresses the polynucleotide sequence.

9. The method of claim 5, wherein the plant cell is a dicot cell.

10. The method of claim 9, wherein the dicot cell is a cotton, soybean, rapeseed, sunflower, tobacco, sugarbeet, or alfalfa cell.

11. The method of claim 5, wherein the plant cell is a monocot cell.

12. The method of claim 11, wherein the monocot cell is a corn, rice, wheat, sorghum, barley, oat, or turfgrass cell.

13. A method of transformation comprising:

a) expressing a transgenic polynucleotide sequence encoding a VIP2 polypeptide in a plant cell susceptible to *Agrobacterium*-mediated transformation; and b) transforming the plant cell with a selected DNA by *Agrobacterium*-mediated transformation;

wherein the efficiency of transformation is increased relative to a cell of the same genotype not expressing the transgenic sequence.

14. The method of claim 13, wherein the plant cell is a dicot cell.

15. The method of claim 14, wherein the dicot cell is a cotton, soybean, rapeseed, sunflower, tobacco, sugarbeet, or alfalfa cell.

16. The method of claim 15 wherein the plant cell is a monocot cell.

17. The method of claim 16, wherein the monocot cell is a corn, rice, wheat, sorghum, barley, oat, or turfgrass cell.

* * * * *

SEQUENCE LISTING

```
<160> NUMBER OF SEQ ID NOS: 46

<210> SEQ ID NO 1
<211> LENGTH: 439
<212> TYPE: PRT
<213> ORGANISM: Arabidopsis thaliana

<400> SEQUENCE: 1

Met Ser Asn Leu His Ser Ser Leu Asn Gly Ser Ala Ser Asn Leu Pro
  1               5                  10                  15

Asp Gly Ser Gly Arg Ser Phe Thr Ala Ser Tyr Ser Gly Gln Ser Gly
             20                  25                  30

Ala Pro Ser Pro Ser Phe His His Thr Gly Asn Leu Gln Gly Leu His
         35                  40                  45

Asn Val His Gly Asn Tyr Asn Val Gly Asn Met Gln Gly Thr Leu Thr
     50                  55                  60

Ser Arg Asn Ser Ser Met Asn Ser Ile Pro Ser Ala Gly Val Gln Gln
 65                  70                  75                  80

Pro Asn Gly Ser Phe Ser Ser Gly Arg Phe Ala Ser Asn Asn Leu Pro
                 85                  90                  95

Val Asn Leu Ser Gln Leu Ser His Gly Ser Ser His Gly His Ser Gly
            100                 105                 110

Ile Pro Asn Arg Gly Leu Asn Val Val Gly Asn Pro Gly Phe Ser Ser
        115                 120                 125
```

Asn Ala Asn Gly Val Gly Gly Ser Ile Pro Gly Ile Leu Ser Thr Ser
130                 135                 140

Ala Gly Leu Ser Asn Arg Asn Ser Val Pro Gly Met Gly Ile Ser Gln
145                 150                 155                 160

Leu Leu Gly Asn Ser Gly Pro Arg Ile Thr Asn Ser Met Gly Asn Met
                165                 170                 175

Val Gly Gly Asn Leu Gly Arg Asn Ile Ser Ser Gly Gly Leu Ser
            180                 185                 190

Val Pro Gly Leu Ser Ser Arg Leu Asn Leu Ala Ala Asn Ser Gly Ser
            195                 200                 205

Gly Leu Asn Val Gln Gly Gln Asn Arg Met Met Gly Gly Val Leu Pro
            210                 215                 220

Gln Gly Ser Gln Val Met Ser Met Leu Gly Asn Ser Tyr His Thr Gly
225                 230                 235                 240

Gly Gly Pro Leu Ser Gln Asn His Val Gln Ser Val Asn Asn Met Met
                245                 250                 255

Leu Ser Asp His Pro Asn Asp Ser Ser Leu Phe Asp Ile Asn Asn Asp
                260                 265                 270

Phe Pro Gln Leu Thr Ser Arg Pro Gly Ser Ala Gly Gly Thr Gln Gly
                275                 280                 285

His Leu Gly Ser Leu Arg Lys Gln Gly Leu Gly Val Pro Leu Val Gln
290                 295                 300

Gln Asn Gln Glu Phe Ser Ile Gln Asn Glu Asp Phe Pro Ala Leu Pro
305                 310                 315                 320

Gly Tyr Lys Gly Gly Asn Ser Glu Tyr Pro Met Asp Leu His Gln Lys
                325                 330                 335

Glu Gln Leu His Asp Asn Ala Met Ser Met Met His Ser Gln Asn Phe
                340                 345                 350

Ser Met Gly Arg Ser Gly Gly Phe Asn Leu Gly Ala Thr Tyr Ser Ser
                355                 360                 365

His Arg Pro Gln Gln Gln Pro Gln His Thr Ser Ser Val Ser Gly Ser
                370                 375                 380

Leu Ser Tyr Pro Tyr Met Tyr Thr Ser Arg Asn Phe Leu Gln Phe Ala
385                 390                 395                 400

Tyr Leu Ile Leu Leu Trp Tyr Cys Ile Met Trp Leu Gly His Thr Cys
                405                 410                 415

Ser Asn Tyr Arg Ile Leu Ser Phe Asn Ser Tyr Leu Ile Pro Asp Trp
                420                 425                 430

Trp Ala Thr Gly Ser Trp Pro
                435

<210> SEQ ID NO 2
<211> LENGTH: 556
<212> TYPE: PRT
<213> ORGANISM: Arabidopsis thaliana

<400> SEQUENCE: 2

Met Gln Gly Thr Leu Thr Ser Arg Asn Ser Ser Met Asn Ser Ile Pro
1               5                   10                  15

Ser Ala Gly Val Gln Gln Pro Asn Gly Ser Phe Ser Ser Gly Arg Phe
                20                  25                  30

Ala Ser Asn Asn Leu Pro Val Asn Leu Ser Gln Leu Ser His Gly Ser
            35                  40                  45

Ser His Gly His Ser Gly Ile Pro Asn Arg Gly Leu Asn Val Val Gly
        50                  55                  60

```
Asn Pro Gly Phe Ser Ser Asn Ala Asn Gly Val Gly Ser Ile Pro
 65                  70                  75                  80

Gly Ile Leu Ser Thr Ser Ala Gly Leu Ser Asn Arg Asn Ser Val Pro
            85                  90                  95

Gly Met Gly Ile Ser Gln Leu Leu Gly Asn Ser Gly Pro Arg Ile Thr
           100                 105                 110

Asn Ser Met Gly Asn Met Val Gly Gly Asn Leu Gly Arg Asn Ile
       115                 120                 125

Ser Ser Gly Gly Leu Ser Ile Pro Gly Leu Ser Ser Arg Leu Asn Leu
130                 135                 140

Ala Ala Asn Ser Gly Ser Gly Leu Asn Val Gln Gly Gln Asn Arg Met
145                 150                 155                 160

Met Gly Gly Val Leu Pro Gln Gly Ser Gln Val Met Ser Met Leu Gly
               165                 170                 175

Asn Ser Tyr His Thr Gly Gly Pro Leu Ser Gln Asn His Val Gln
           180                 185                 190

Ser Val Asn Asn Met Met Leu Ser Asp His Pro Asn Asp Ser Ser Leu
       195                 200                 205

Phe Asp Ile Asn Asn Asp Phe Pro Gln Leu Thr Ser Arg Pro Gly Ser
210                 215                 220

Ala Gly Gly Thr Gln Gly His Leu Gly Ser Leu Arg Lys Gln Gly Leu
225                 230                 235                 240

Gly Val Pro Leu Val Gln Gln Asn Gln Glu Phe Ser Ile Gln Asn Glu
               245                 250                 255

Asp Phe Pro Ala Leu Pro Gly Tyr Lys Gly Gly Asn Ser Glu Tyr Pro
           260                 265                 270

Met Asp Leu His Gln Lys Glu Gln Leu His Asp Asn Ala Met Ser Met
       275                 280                 285

Met His Ser Gln Asn Phe Ser Met Gly Arg Ser Gly Gly Phe Asn Leu
       290                 295                 300

Gly Ala Thr Tyr Ser Ser His Arg Pro Gln Gln Gln Pro Gln His Thr
305                 310                 315                 320

Ser Ser Thr Gly Gly Leu Gln Gly Leu Gly Leu Arg Pro Leu Ser Ser
               325                 330                 335

Pro Asn Ala Val Ser Ser Ile Gly Tyr Asp Gln Leu Ile Gln Gln Tyr
           340                 345                 350

Gln Gln His Gln Asn Gln Ser Gln Phe Pro Val Gln Gln Met Ser Ser
       355                 360                 365

Ile Asn Gln Phe Arg Asp Ser Glu Met Lys Ser Thr Gln Ser Glu Ala
370                 375                 380

Asp Pro Phe Cys Leu Leu Gly Leu Leu Asp Val Leu Asn Arg Ser Asn
385                 390                 395                 400

Pro Glu Leu Thr Ser Leu Ala Leu Gly Ile Asp Leu Thr Thr Leu Gly
               405                 410                 415

Leu Asp Leu Asn Ser Thr Gly Asn Leu Tyr Lys Thr Phe Ala Ser Pro
           420                 425                 430

Trp Thr Asn Glu Pro Ala Lys Ser Glu Val Glu Phe Thr Val Pro Asn
       435                 440                 445

Cys Tyr Tyr Ala Thr Glu Pro Pro Leu Thr Arg Ala Ser Phe Lys
       450                 455                 460

Arg Phe Ser Tyr Glu Leu Leu Phe Tyr Thr Phe Tyr Ser Met Pro Lys
465                 470                 475                 480

Asp Glu Ala Gln Leu Tyr Ala Ala Asp Glu Leu Tyr Glu Arg Gly Trp
```

```
                    485                 490                 495
Phe Tyr His Lys Glu Leu Arg Val Trp Phe Phe Arg Val Gly Glu Pro
                500                 505                 510

Leu Val Arg Ala Ala Thr Tyr Glu Arg Gly Thr Tyr Glu Tyr Leu Asp
                515                 520                 525

Pro Asn Ser Phe Lys Thr Val Arg Lys Glu His Phe Val Ile Lys Tyr
                530                 535                 540

Glu Leu Met Glu Lys Arg Pro Ser Leu Leu Gln Leu
545                 550                 555

<210> SEQ ID NO 3
<211> LENGTH: 1671
<212> TYPE: DNA
<213> ORGANISM: Arabidopsis thaliana

<400> SEQUENCE: 3
atgcaaggta cacttacatc aagaaactca agtatgaata gtataccatc tgccggagtt      60
caacaaccta tgggagtttt tccagtggaa gatttgcttc aaataatctt acctgttaat     120
ctctctcagt tgtcccatgg tagctcacat gggcattcgg gaatcccaaa tagaggtctt     180
aatgttgttg caaccctgga attcagtagt aacgctaatg gagttggtgg ttctattcct     240
ggaattctct ctacatctgc aggactcagt aatcggaata tgttccagg atgggaata      300 tcccaattgt tgggaaattc aggtcctcga ataacaaatt caatgggaaa catggttggt     360
ggaggtaact tggggaggaa tattagctct ggtggattgt ctattcctgg tctgtcttca     420
cgactaaatt tggcagcaaa tagcggatca ggattaaatg ttcagggaca gaaccgaatg     480
atgggtggag tacttcctca aggatctcag gtcatgtcta tgctggggaa ctcctatcat     540
actggtggtg gcccgctttc gcagaatcat gttcagtcag ttaacaatat gatgctcagt     600
gatcatccta cgacagctc tctatttgac atcaacaacg attttcccca gctgacaagt      660
cgtcctgggt ctgctggtgg cactcaagga catctaggct ctttgaggaa caaggttta     720 ggagttccac ttgtccaaca aaaccaggag ttcagcatcc aaaatgaaga cttcctgcc      780 cttcctggat ataaaggtgg taattctgag atcctatgg atttgcatca aaagaacaa      840 ctgcatgaca atgctatgtc aatgatgcac tctcaaaact tttctatggg tagatctggt     900
ggtttcaact gggagcaac atattcatca catcgtccac aacaacagcc acaacatact      960
tcatctactg gtgggctaca gggtcttggc cttagacctc taagctcgcc taatgcagtt    1020
tccagtattg gttatgatca gcttattcag cagtatcagc aacatcaaaa tcaatcccag    1080
ttccctgtgc aacagatgtc atcaatcaac aatttagag attctgagat gaaatcgaca    1140
cagtcagagg cagatccttt tgcttgctt ggcttgttag acgtactaaa caggagcaac    1200
cctgaattga cctcacttgc tcttggcatc gacttgacga cgctaggatt ggatttgaat    1260
tcaactggaa atctctacaa gacatttgcg tctccttgga caaatgaacc ggcaaagagc    1320
gaggtcgagt tcacagtacc aaattgttac tacgccacag aacctccgcc tctaactcga    1380
gctagtttca aaggttctc ctacgagtta ttgttctaca catttacag tatgccaaaa    1440 gatgaagcac agctgtacgc agcagatgaa ctttacgaaa gaggttggtt ttaccacaag    1500
gaactcagag tatggttctt cagagtcggg gaacctttag tcaggcagc tacatatgaa    1560 agaggaacat acgaataccct tgatccaaat tcgttcaaaa cagtgagaaa ggaacatttt    1620
gttatcaagt acgagcttat ggaaaagaga ccaagcttgc tgcagctttg a             1671

<210> SEQ ID NO 4
```

<211> LENGTH: 603
<212> TYPE: PRT
<213> ORGANISM: Nicotiana benthamiana

<400> SEQUENCE: 4

```
Met Gln Gly Thr Leu Thr Ser Arg Asn Thr Ala Ile Asn Asn Val Pro
 1               5                  10                  15

Ser Ser Gly Val Gln Gln Ser Gly Asn Asn Leu Ser Gly Gly Arg Phe
             20                  25                  30

Val Pro Asn Asn Leu Pro Ser Ala Leu Ser Gln Ile Pro Gln Gly Asn
         35                  40                  45

Ser His Gly His Ser Gly Met Thr Ser Arg Gly Gly Thr Ser Val Val
     50                  55                  60

Gly Asn Pro Gly Tyr Ser Ser Asn Thr Asn Gly Val Gly Gly Ser Ile
 65                  70                  75                  80

Pro Gly Ile Leu Pro Thr Phe Ala Ala Ile Gly Asn Arg Ser Ser Val
                 85                  90                  95

Pro Gly Leu Gly Val Ser Pro Ile Leu Gly Asn Ala Gly Pro Arg Met
            100                 105                 110

Thr Asn Ser Val Gly Asn Ile Val Gly Gly Asn Ile Gly Arg Ser
        115                 120                 125

Ile Ser Ser Gly Ala Gly Leu Ser Val Pro Gly Leu Ala Ser Arg Leu
    130                 135                 140

Asn Met Asn Ala Asn Ser Gly Ser Gly Asn Leu Asn Val Gln Gly Pro
145                 150                 155                 160

Asn Arg Leu Met Ser Gly Val Leu Gln Gln Ala Ser Pro Gln Val Leu
                165                 170                 175

Ser Met Leu Gly Asn Ser Tyr Pro Ala Gly Gly Pro Leu Ser Gln Asn
            180                 185                 190

His Val Gln Ala Ile Gly Asn Phe Asn Ser Met Gly Leu Leu Asn Asp
        195                 200                 205

Val Asn Ser Asn Asp Gly Ser Pro Phe Asp Ile Asn Asp Phe Pro Gln
    210                 215                 220

Leu Ser Ser Arg Pro Ser Ser Ala Gly Gly Pro Gln Gly Gln Leu Gly
225                 230                 235                 240

Ser Leu Arg Lys Gln Gly Leu Ser Pro Ile Val Gln Asn Gln Glu
                245                 250                 255

Phe Ser Ile Gln Asn Glu Asp Phe Pro Ala Leu Pro Gly Phe Lys Gly
            260                 265                 270

Gly Asn Ala Asp Tyr Ala Met Asp Pro His Gln Lys Glu Gln Leu His
        275                 280                 285

Asp Asn Thr Leu Ser Met Met Gln Gln Gln His Phe Ser Met Gly Arg
    290                 295                 300

Ser Ala Gly Phe Asn Leu Gly Gly Thr Tyr Ser Ser Asn Arg Pro Gln
305                 310                 315                 320

Gln Gln Leu Gln His Ala Pro Ser Val Ser Ser Gly Val Ser Phe
                325                 330                 335

Ser Asn Ile Asn Asn Gln Asp Leu Leu Ser Leu His Gly Ser Asp Val
            340                 345                 350

Phe Gln Ser Ser His Ser Ser Tyr Gln Gln Gln Gly Gly Pro Pro
        355                 360                 365

Gly Ile Gly Leu Arg Pro Leu Asn Ser Ser Gly Thr Val Ser Gly Ile
    370                 375                 380

Gly Ser Tyr Asp Gln Leu Ile Gln Gln Tyr Gln His Gln Gly Gln
385                 390                 395                 400
```

Ser Gln Phe Arg Leu Gln Gln Met Ser Thr Leu Gly Gln Pro Phe Arg
            405                 410                 415

Asp Gln Ser Leu Lys Ser Met Gln Ser Gln Val Ala Pro Asp Pro Phe
            420                 425                 430

Gly Met Leu Gly Leu Leu Ser Val Ile Arg Met Ser Asp Pro Asp Leu
            435                 440                 445

Thr Ser Leu Ala Leu Gly Ile Asp Leu Thr Thr Leu Gly Leu Asn Leu
            450                 455                 460

Asn Ser Ala Glu Asn Leu Tyr Lys Thr Phe Gly Ser Pro Trp Ser Asp
465                 470                 475                 480

Glu Pro Ala Lys Gly Asp Pro Glu Phe Thr Val Pro Gln Cys Tyr Tyr
            485                 490                 495

Ala Lys Gln Pro Pro Leu Asn Gln Ala Tyr Phe Ser Lys Phe Gln
            500                 505                 510

Leu Asp Thr Leu Phe Tyr Ile Phe Tyr Ser Met Pro Lys Asp Glu Ala
            515                 520                 525

Gln Leu Tyr Ala Ala Asn Glu Leu Tyr Asn Arg Gly Trp Phe Tyr His
            530                 535                 540

Arg Glu His Arg Leu Trp Phe Met Arg Val Ala Asn Met Glu Pro Leu
545                 550                 555                 560

Val Lys Thr Asn Ala Tyr Glu Arg Gly Ser Tyr Ile Cys Phe Asp Pro
            565                 570                 575

Asn Thr Trp Glu Thr Ile His Lys Asp Asn Phe Val Leu His Cys Glu
            580                 585                 590

Met Leu Glu Lys Arg Pro Val Leu Pro Gln His
            595                 600

<210> SEQ ID NO 5
<211> LENGTH: 713
<212> TYPE: DNA
<213> ORGANISM: Lycopersicon esculentum

<400> SEQUENCE: 5
gggcaacatt ggcagaagca ttagctctgc aggattgtct gtgactaatc ttgcttcacg      60
gttaaatatg aacgccaatg ccggttctgg aaatttaaat gttcaaggac ctaataggat     120
aatgagtggt gttcttcagc aagcctctcc gcaggtactt tctatgttag aaattccta     180
ttctgctggt ggtccactag ctcaaaacca tgtccaagca atgggaaacc ttaattcttt     240
gggattgttg aatgatgtaa attcaaatga tggatctcct tttgatatca atgatttccc     300
tcagttaagc agtcgaccta gttctgctgg aggacctcaa ggacaaatgg gttctttgcg     360
gaaacaaggg atcagtccta tgttcagca aaaccaggaa ttcagcattc aaaatgaaga     420
ttttcctgct ttaccaggat ttaaaggtgg gaatgctgat tatgcgatgg atcctcacca     480
gaaagagcag cttcatgata atgctctttc tatgatgcaa cagcaacact tctaatggga     540
aagatccaca ggttttaatt tgggtggaac atattcatca catcgtccgc agccgcagct     600
gcaacatgct ccatctggtt agtagaccgg ggtgtcttct ttttcaatat aaacacccag     660
gatctggctg agtttacatg ggtccagatg tcttccatcc atcgcagtcc aat            713

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic Primer

```
<400> SEQUENCE: 6
gatttccctc agttaagcag tcg                                            23

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
gactgcgatg gatggaagac                                                20

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
ggggacaagt ttgtacaaaa aagcaggct                                      29

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 9
ggggaccact ttgtacaaga aagctgggt                                      29

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 10
ctgggttact agcggcactg aata                                           24

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 11
tccaccaaac ttaatcccga atac                                           24

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 12
```
gatttccctc agctaagcag cc                                             22

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 13
tggaagacat ctgaaccatg taaa                                           24

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 14
tgaggctctt gaccagatta atga                                           24

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 15
gtaaacatcc tgaagtggaa gacgta                                         26

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 16
aaggtgggaa tgctgattat gc                                             22

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 17
tcttcccatt gagaagtgtt gct                                            23

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 18
cgatcagttc gccgatgg                                                  18

-continued

```
<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 19
tcccgctagt gccttgtcc                                                  19

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 20
gcgttcgctg gtgtcacgcc                                                 20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 21
gatcagcgga gaccagcttc                                                 20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 22
aggtgcacgg gaatatttcg                                                 20

<210> SEQ ID NO 23
<211> LENGTH: 17
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 23
acgcgtcggg tcgagtt                                                    17

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 24
tggttcgggc agatcgttta ctgc                                            24
```

| | | | | |
|---|---|---|---|---|
| <210> SEQ ID NO 25 | | | | |
| <211> LENGTH: 20 | | | | |
| <212> TYPE: DNA | | | | |
| <213> ORGANISM: Artificial Sequence | | | | |
| <220> FEATURE: | | | | |
| <223> OTHER INFORMATION: Description of Artificial Sequence: Synthetic Primer | | | | |

<400> SEQUENCE: 25

| | |
|---|---|
| gcaagcttgg tctcttttcc | 20 |

| | | | | |
|---|---|---|---|---|
| <210> SEQ ID NO 26 | | | | |
| <211> LENGTH: 1812 | | | | |
| <212> TYPE: DNA | | | | |
| <213> ORGANISM: Nicotiana benthamiana | | | | |

<400> SEQUENCE: 26

| | | | | |
|---|---|---|---|---|
| atgcaaggta | cacttacatc | aagaaacaca | gcaataaata | acgtcccctc cagtggtgtc | 60 |
| cagcaatctg | ggaataatct | ttctggtggt | cgttttgtac | caaacaatct tcccagtgcc | 120 |
| ctttctcaga | taccccaagg | caattcgcat | ggtcattctg | ggatgacgag tagaggtggt | 180 |
| acgagtgttg | ttggtaaccc | gggatatagc | agtaacacta | atggtgtagg gggttctatc | 240 |
| cctggaattc | tcccaacctt | tgcagcaatt | ggtaatcgaa | gttctgtgcc aggccttggg | 300 |
| gtgtccccca | ttttgggaaa | tgcaggccca | aggatgacga | actcagttgg aaatatagtt | 360 |
| ggtgggggca | acattggcag | aagcattagc | tccggtgcag | gattgtctgt gcctggtctt | 420 |
| gcttcacggc | taaatatgaa | cgccaactct | ggctctggaa | atttaaatgt tcaaggacct | 480 |
| aataggctaa | tgagtggtgt | tcttcagcaa | gcctctccgc | aggttctttc tatgttaggg | 540 |
| aattcctacc | cagctggtgg | cccgctgtct | caaaaccacg | tccaagcaat tggcaatttt | 600 |
| aactctatgg | gattgttgaa | tgacgtaaat | tcaaatgatg | gatctccttt tgatatcaat | 660 |
| gatttccctc | agctaagcag | ccggcccagt | tcggctggag | gacctcaagg acaattgggt | 720 |
| tccttacgga | agcaagggct | cagtcctatt | gttcaacaaa | atcaggaatt cagcattcaa | 780 |
| aatgaagatt | ttcctgcttt | acctggattt | aaaggtggga | atgctgatta tgctatggat | 840 |
| cctcaccaga | aagagcaact | ccatgataat | actctttcga | tgatgcagca gcaacacttc | 900 |
| tcaatgggaa | gatctgctgg | ttttaacttg | ggggaacat | actcatcgaa tcgtccacag | 960 |
| cagcagctgc | aacatgctcc | atctgttagt | agtggtggtg | tctcctttc aaatataaat | 1020 |
| aaccaggatc | tgctgagttt | acatggttca | gatgtcttcc | aatcatcgca ctccagttac | 1080 |
| cagcaacagg | gtggtggacc | tcctggtatt | gggttacgac | tcttaactc ttcaggtact | 1140 |
| gtttctggga | ttggatcata | tgatcagctt | atccagcagt | accaacagca tcagggtcaa | 1200 |
| tcccaatttc | ggttgcagca | aatgtctact | ttaggtcagc | cattcaggga tcagagctta | 1260 |
| aagtccatgc | aatcccaagt | tgctcctgac | ccgtttggta | tgcttggttt gctaagtgta | 1320 |
| atacggatga | gcgatccgga | tttgacttct | cttgcacttg | gaattgatct aacaacactt | 1380 |
| ggattaaatt | tgaactctgc | tgaaaatttg | tataagacat | ttggttcccc gtggtctgat | 1440 |
| gagcctgcta | aggggatcc | agagtttaca | gtaccccaat | gttattatgc gaagcaaccg | 1500 |
| ccacctttaa | atcaagcgta | cttctcaaag | tttcagctag | atactttgtt ctacattttt | 1560 |
| tacagcatgc | caaaagatga | agcacagcta | tatgctgcaa | atgaactgta caaccgtggc | 1620 |
| tggttctatc | acagagaaca | tcggttgtgg | tttatgcggg | ttgccaacat ggagcctctc | 1680 |
| gtcaagacga | atgcatatga | gagagggtct | tacattttgtt | ttgatccaaa cacatgggag | 1740 |
| acaatccaca | aggataattt | tgtgctccac | tgtgaaatgt | tggaaaaaag acctgttctg | 1800 | cctcaacact aa                                                                                      1812

<210> SEQ ID NO 27
<211> LENGTH: 622
<212> TYPE: PRT
<213> ORGANISM: Nicotiana benthamiana

<400> SEQUENCE: 27

| Met | Ser | Gly | Leu | Leu | Asn | Ser | Asn | Leu | Asn | Asn | Ser | Ala | Ser | Asn | Leu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Gln Asp Ser Thr Gly Arg Pro Phe Thr Gly Ser Phe Ser Gly Gln Ser
            20                  25                  30

Gly Ser Val Pro Gly Gly Phe His Ser Gly Leu His Asn Met His
        35                  40                  45

Gly Ser Leu Asn Met Pro Asn Met Pro Gly Ser Phe Gln Arg Asn
    50                  55                  60

Ala Ala Met Ser Gly Leu Pro Ser Ser Val Gln Gln Pro Gly Gly
65                  70                  75                  80

Ser Met Pro Gly Arg Phe Ala Ser Asn Asn Leu Pro Val Gly Met Ser
                85                  90                  95

Gln Ile Pro His Gly His Ser Gly Val Gly Ser Arg Gly Leu Asn Val
                100                 105                 110

Gly Gly Gly Pro Ala Phe Ser Ser Ser Leu Asn Ile Gly Gly Thr Ile
                115                 120                 125

Gln Gly Leu Ser Ser Asn Leu Gly Ala Gly Gly Ser Arg Asn Ser Val
            130                 135                 140

Pro Gly Met Ser Val Ser Pro Ser Leu Gly Asn Leu Gly Pro Arg Ile
145                 150                 155                 160

Thr Gly Ser Val Gly Asn Ile Val Gly Gly Ser Asn Ile Gly Arg Asn
                165                 170                 175

Ile Ser Ser Gly Gly Leu Ser Val Pro Ser Ile Ala Ser Arg Met Asn
                180                 185                 190

Leu Ser Gly Asn Val Gly Ser Gly Gly Leu Asn Val Gln Gly Ser Ser
            195                 200                 205

Arg Met Met Asn Gly Ile Leu Gln Gln Gly Ser Pro Gln Met Leu Asn
210                 215                 220

Met Met Gly Ser Leu Tyr Pro Thr Ser Gly Gly Ser Leu Ser Gln Asn
225                 230                 235                 240

Gln Ile Gln Gly Gly Asn Asn Ser Leu Gly Ser Met Gly Met Leu His
                245                 250                 255

Asp Ala Ser Asp Gly Ala Pro Phe Asp Met Ser Asp Phe Pro Gln Leu
                260                 265                 270

Thr Gly Arg Pro Ser Ser Ala Gly Gly Pro Gln Gly Gln Tyr Gly Ser
            275                 280                 285

Leu Arg Lys Gln Gly Val Gly Val Asn Thr Ile Val Gln Gln Asn Gln
290                 295                 300

Glu Phe Ser Ile Gln Asn Glu Asp Phe Pro Ala Leu Pro Gly Tyr Lys
305                 310                 315                 320

Gly Asn Thr Thr Asp Tyr Ala Met Glu Leu His His Lys Glu Gln Leu
                325                 330                 335

His Asp Asn Val Pro Val Met Gln Ala Gln Gln Tyr Pro Met Ser Arg
                340                 345                 350

Ser Val Gly Phe Asn Leu Gly Ser Asn Tyr Pro Pro Asn Arg Gln Gln
            355                 360                 365

His Gln Gln Gly Ala Asn Ser Val Gln Asn Ala Gly Pro Pro Asn Ile

```
            370                 375                 380
Gly Leu Arg Pro Leu Asn Ser Pro Asn Gln Thr Ser Ser Leu Gly Ser
385                 390                 395                 400

Tyr Glu Gln Leu Ile Gln Gln Tyr Gln Pro Gln Ala Gln Asn Pro
                405                 410                 415

Phe Arg Leu Gln Gln Val Ser Ser Ala Thr Gln Ser Tyr Arg Asp Gln
                420                 425                 430

Ser Leu Lys Ser Ile Gln Gly Gly Gln Thr Pro Ser Asp Pro Tyr Gly
                435                 440                 445

Leu Met Gly Leu Leu Gly Val Ile Arg Met Asn Asp Val Asp Leu Ser
450                 455                 460

Ser Leu Ala Leu Gly Ile Asp Leu Thr Thr Leu Gly Leu Asn Leu Asn
465                 470                 475                 480

Ser Pro Asp Asn Leu Tyr Lys Thr Phe Gly Ser Pro Trp Ser Asn Glu
                485                 490                 495

Pro Ala Lys Gly Glu Pro Glu Phe His Thr Pro Ala Cys Tyr Ser Ala
                500                 505                 510

Glu Gln Pro Pro Leu Gln Pro Ile His Phe Gln Lys Phe Gln Thr
                515                 520                 525

Pro Thr Leu Phe Tyr Ile Phe Tyr Ser Met Pro Arg Asp Glu Ala Gln
530                 535                 540

Leu Cys Ala Ala Ser Glu Leu Tyr Thr Arg Gly Trp Phe Tyr His Lys
545                 550                 555                 560

Glu Val Arg Val Trp Leu Thr Arg Ile Pro Asn Val Glu Pro Leu Val
                565                 570                 575

Lys Thr Pro His Tyr Glu Arg Gly Ser Tyr Gly Cys Phe Asp Pro Asn
                580                 585                 590

Asn Trp Glu Thr Ile Arg Lys Asp Asn Phe Val Leu His Tyr Asp Gln
                595                 600                 605

Ile Glu Lys Lys Pro Ala Ile Pro Ser Ser Gln Asn Val Arg
610                 615                 620

<210> SEQ ID NO 28
<211> LENGTH: 512
<212> TYPE: PRT
<213> ORGANISM: Nicotiana benthamiana

<400> SEQUENCE: 28

Met Ser His Gly Ser Ser His Gly His Ser Gly Leu Thr Asn Arg Gly
1               5                   10                  15

Gly Leu Gly Val Ser Pro Ile Leu Gly Asn Val Gly Ser Arg Met Thr
                20                  25                  30

Ser Ser Met Gly Asn Met Val Gly Gly Thr Met Gly Arg Thr Leu
            35                  40                  45

Ser Ser Gly Gly Gly Leu Ser Ile Pro Ser Leu Gly Ser Arg Leu Asn
    50                  55                  60

Leu Ala Val Asn Ser Gly Ser Gly Asn Ile Gly Gln Asn Arg Met Met
65                  70                  75                  80

Gly Gly Val Leu Pro Gln Gly Ser Pro Gln Val Leu Ser Met Leu Gly
                85                  90                  95

Asn Ser Tyr Pro Ser Ala Gly Gly Leu Ser Gln Asn His Val Gln Ala
                100                 105                 110

Met Asn Ser Leu Ser Ser Met Gly Leu Leu Asn Asp Met Asn Ser Asn
            115                 120                 125

Asp Thr Ser Pro Phe Asp Ile Asn Asn Asp Phe Pro Gln Leu Thr Ser
```

```
            130                 135                 140
Arg Pro Ser Ser Ala Gly Ser Gln Gly Gln Leu Gly Ser Arg Leu Lys
145                 150                 155                 160

Gln Gly Leu Gly Ile Ser Pro Ile Val Gln Gln Asn Gln Glu Phe Ser
                165                 170                 175

Ile Gln Asn Glu Asp Phe Pro Ala Leu Pro Gly Tyr Lys Gly Ser Ser
            180                 185                 190

Ala Asp Tyr Pro Met Asp Leu His His Lys Glu Gln Leu His Glu Asn
        195                 200                 205

Ser Val Leu Met Met Gln Ser Gln Gln Leu Ser Met Gly Arg Ser Gly
    210                 215                 220

Gly Phe Asn Leu Gly Gly Ala Tyr Thr Ser His Arg Pro Gln Gln Gln
225                 230                 235                 240

Gln Gln His Ala Gln Ala Val Ser Ser Ser Gly Val Ser Leu His Gly
                245                 250                 255

Ser Asp Ile Phe Ser Ser Ser Pro Pro Tyr His Ser Gln Thr Gly
            260                 265                 270

Gly Ala Pro Gly Ile Gly Leu Arg Ser Met Asn Ser Ala Asn Ser Ile
        275                 280                 285

Thr Gly Met Gly Tyr Asp Gln Gln Leu Ile Gln Gln Tyr Gln His Gln
    290                 295                 300

Gln Asn Ser Ala Gln Tyr Arg Leu Gln Gln Met Ser Ala Ala Ser Gln
305                 310                 315                 320

Pro Phe Arg Asp Val Gly Leu Lys Ser Met Gln Ser Thr Gln Ser Asn
                325                 330                 335

Pro Asp Arg Phe Gly Leu Leu Gly Leu Leu Ser Val Ile Lys Met Ser
            340                 345                 350

Asp Pro Asp Leu Thr Ser Leu Ala Leu Gly Ile Asp Leu Thr Thr Leu
        355                 360                 365

Gly Leu Asn Leu Asn Ser Thr Glu Asn Leu His Lys Thr Phe Gly Ser
    370                 375                 380

Pro Trp Ser Asn Glu Pro Ser Lys Val Asp Pro Glu Phe Ser Val Pro
385                 390                 395                 400

Gln Cys Tyr Tyr Ala Lys Asn Pro Pro Leu His Gln Gly Leu Phe
                405                 410                 415

Ala Lys Leu Leu Val Glu Thr Leu Phe Tyr Val Phe Tyr Ser Met Pro
            420                 425                 430

Lys Asp Glu Ala Gln Leu Tyr Ala Ala Asn Glu Leu Tyr Asn Arg Gly
        435                 440                 445

Trp Phe Tyr His Lys Glu His Arg Leu Trp Phe Ile Arg Ile Gly Glu
    450                 455                 460

Pro Leu Val Lys Thr Asn Ala Tyr Glu Arg Gly Ser Tyr His Cys Phe
465                 470                 475                 480

Asp Pro Asn Ser Phe Glu Ile Val Gln Lys Glu Asn Phe Val Leu Tyr
                485                 490                 495

Tyr Glu Met Leu Glu Lys Arg Pro Ser Ile Ser Gln Asp Ser Gln His
            500                 505                 510

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence:  Synthetic
      primer
```

```
<400> SEQUENCE: 29
ggaaagctgg aaactggttg at                                            22

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gcagaggaaa agcaaatgaa aaa                                           23

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
cactaatctt tgcgccattc ac                                            22

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
cgcgagctgg atatccttag g                                             21

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gcggattcaa tggcttcaa                                                19

<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cacttgcaga aaccatggct aa                                            22

<210> SEQ ID NO 35
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
```

```
cctaacattc acaatcttct tcttcct                                            27
```

<210> SEQ ID NO 36
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36

```
caagagagtg gatttggttg attaatc                                            27
```

<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37

```
gttttcgttg ctagtttgtg tttga                                              25
```

<210> SEQ ID NO 38
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38

```
ccaaatacat agaaactaag atccaaaagc                                         30
```

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39

```
tgcgatcaag aaattccaga aa                                                 22
```

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40

```
caatgctgcc ctaattacaa caca                                               24
```

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41

```
ggttggatta ggttttgcgt tt                                                 22
```

-continued

```
<210> SEQ ID NO 42
<211> LENGTH: 25
<212> TYPE: DNA
<213> ORGANISM: Artificial Sequence
<220> FEATURE:
<223> OTHER INFORMATION: Description of Artificial Sequence:  Synthetic
      primer

<400> SEQUENCE: 42
tttgctaagg aaggagagat tttga                                          25

<210> SEQ ID NO 43
<211> LENGTH: 22
<212> TYPE: DNA
<213> ORGANISM: Artificial Sequence
<220> FEATURE:
<223> OTHER INFORMATION: Description of Artificial Sequence:  Synthetic
      primer

<400> SEQUENCE: 43
tcatcaacaa aaccaccaag ga                                             22

<210> SEQ ID NO 44
<211> LENGTH: 28
<212> TYPE: DNA
<213> ORGANISM: Artificial Sequence
<220> FEATURE:
<223> OTHER INFORMATION: Description of Artificial Sequence:  Synthetic
      primer

<400> SEQUENCE: 44
tgagtccaag actacagaaa tacaaaca                                       28

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence:  Synthetic
      primer

<400> SEQUENCE: 45
cggagctcaa ttctcggaat t                                              21

<210> SEQ ID NO 46
<211> LENGTH: 22
<212> TYPE: DNA
<213> ORGANISM: Artificial Sequence
<220> FEATURE:
<223> OTHER INFORMATION: Description of Artificial Sequence:  Synthetic
      primer

<400> SEQUENCE: 46
aggaagctcg agtgccaagt ac                                             22
```